US007951996B2

(12) United States Patent
Komatsuda et al.

(10) Patent No.: US 7,951,996 B2
(45) Date of Patent: May 31, 2011

(54) BARLEY ROW TYPE GENE AND USE THEREOF

(75) Inventors: Takao Komatsuda, Ibaraki (JP); Masahiro Yano, Ibaraki (JP); Takashi Matsumoto, Ibaraki (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 85 days.

(21) Appl. No.: 12/086,663

(22) PCT Filed: Dec. 14, 2006

(86) PCT No.: PCT/JP2006/324911
§ 371 (c)(1),
(2), (4) Date: Oct. 10, 2008

(87) PCT Pub. No.: WO2007/069677
PCT Pub. Date: Jun. 21, 2007

(65) Prior Publication Data
US 2009/0119798 A1 May 7, 2009

(30) Foreign Application Priority Data
Dec. 14, 2005 (JP) ................................ 2005-359826

(51) Int. Cl.
*C12N 15/29* (2006.01)
*C12N 15/82* (2006.01)
*C12N 5/04* (2006.01)
*A01H 5/00* (2006.01)

(52) U.S. Cl. ........ 800/300; 800/298; 800/278; 800/279; 435/320.1; 435/419; 536/23.1; 536/23.6

(58) Field of Classification Search ........................ None
See application file for complete search history.

(56) References Cited

U.S. PATENT DOCUMENTS

2006/0236422 A1 10/2006 Komatsuda et al.

FOREIGN PATENT DOCUMENTS

JP 2004-313062 11/2004
WO WO 2004/092366 10/2004

OTHER PUBLICATIONS

Wang et al (2005, Planta 221:831-843).*
Chuck et al (1996, The Plant Cell 8:1277-1289).*
Bowie et al, Science 247:1306-1310, 1990.*
McConnell et al, Nature 411 (6838):709-713, 2001.*
Komatsuda et al (2004, Hereditas 141:68-73).*
Zhang et al (2003, NCBI Accession No. CB875128).*
Anderson et al (2003, NCBI Accession No. CN013069).*
Koo et al., Integration of Cytogenetic and Genetic Linkage Maps Unveils the Physical Architecture of Tomato Chromosome 2, Genetics, Jul. 2008, pp. 1211-1220, vol. 179.
Pourkheirandish et al., Analysis of the barley chromosome 2 region containing the six-rowed spike gene vrs1 reveals a breakdown of rice-barley micro collinearity by a transposition, Theor Appl Genet, 2007, pp. 1357-1365, vol. 114.
Rostoks et al., Genomic sequencing reveals gene content, genomic organization, and recombination relationships in barley, Funct Integr Genomics, 2002, pp. 51-59, vol. 2.
UniProt Accession No. CB875128, Apr. 24, 2003.
Komatsuda et al., Development of STS markers closely linked to the vrs1 locus in barley, Hordeum valgare, Genome, 1998, pp. 680-685, vol. 41.
Komatsuda et al., High resolution map around the vrs1 locus controlling two- and six-rowed spike in barley, Hordeum vulgare, Genome, 1999, pp. 248-253, vol. 42.
Liu et al., EMBL Accession No. ADX62946, Apr. 21, 2005.
Supplementary European Search Report, EP 06 83 4665, dated Feb. 26, 2009.
DDBJ/EMBL/GenBank Accession No. AP 004276: Jul. 22, 2004 uploaded, Mar. 7, 2007 retrieved. <http://www.ncli.nlm.nih.gov/entrez/viewer.fcgi?db=nucleotide&val=33146816>.
He et al. AFLP targeting of 1-cM region conferring the vrs1 gene for six-rowed spike in barley, Hordeum vulgare L, Genome, Dec. 2004, pp. 1122-1129, vol. 47, No. 6.
Komatsuda et al., Comparative high resolution map of the six-rowed spike locus 1 (vrs1) in several populations of barley, Hordeum vulgare L, Hereditas, 2004, pp. 68-73, vol. 141, No. 1.
Michalek et al., Sequence analysis and gene identification in a set of mapped RFLP markers in barley (Hordeum vulgare), Genome, Oct. 1999, pp. 849-853.
Sasaki et al., Cell Technology Separate Volume Shokubutsu Saibo Kogaku Series 14 Shokubutsu no Genome Kenkyu Protocol, Feb. 2001, pp. 89-94, 1st Edition (Search Report to show relevance).
PCT International Search Report for Application No. PCT/JP2006/324911, dated Mar. 20, 2007, 2 pages (Consise explanation of relevance for Sasaki et al. and WO 2004/092366).

* cited by examiner

*Primary Examiner* — Stuart F. Baum
(74) *Attorney, Agent, or Firm* — TraskBritt

(57) ABSTRACT

The present invention provides the chromosomal location and structure of a gene involved in the determination of row type and panicle morphology of barley. The present inventors have found that the row type and panicle morphology of barley can be altered by introducing the Vrs1 gene provided by the present invention into barley and regulating its expression. Furthermore, the present inventors found the possibility of enhancing the resistance of barley to *Fusarium* head blight. Thus, barley having phenotypes suitable for the intended purpose can be created by efficiently altering the row type and panicle morphology of barley.

14 Claims, 16 Drawing Sheets

FIG. 3-1

| Code | Name | Origin | Mutagen | CF317052 | E30 | 351N10-T7(203-392) | STS2 | E42 | 111L15f1F | 699N11-T7(U179-L402) | 185K11-T7(U07/L213) | 572D24-fc-R(U01/L407) | E18 | end3 | BC12348 | BC1206 | BC05376 | GAN007 | BC14030 |
|---|---|---|---|---|---|---|---|---|---|---|---|---|---|---|---|---|---|---|---|
| 9 | Bonus | | | + | + | + | + | + | + | + | + | + | + | + | + | + | + | + | + |
| 10 | Foma | | | + | + | + | + | + | + | + | + | + | + | + | + | + | + | + | + |
| 11 | Kristina | | | + | + | + | + | + | + | + | + | + | + | + | + | + | + | + | + |
| 12 | Int-d.11 | Foma | Ethylene imine | + | + | + | + | + | + | + | + | + | + | + | + | + | + | + | + |
| 13 | Int-d.12 | Foma | Ethylene imine | + | + | + | + | + | + | + | + | + | + | + | + | + | + | + | + |
| 14 | Int-d.22 | Foma | Methyl methanesulfonate | + | + | + | + | + | + | + | + | + | + | + | + | + | + | + | + |
| 15 | Int-d.24 | Foma | Buthyl methanesulfonate | + | + | + | + | + | + | + | + | + | + | + | + | + | + | + | + |
| 16 | Int-d.28 | Foma | Iso-Propyl methanesulfonate | + | + | + | + | + | + | + | + | + | + | + | + | + | + | + | + |
| 17 | Int-d.36 | Foma | Ethyl methanesulfonate | + | + | + | + | + | + | + | + | + | + | + | + | + | + | + | + |
| 18 | Int-d.40 | Kristina | Ethyl methanesulfonate | + | + | + | + | + | + | + | + | + | + | + | + | + | + | + | + |
| 19 | Int-d.41 | Kristina | Ethyl hydroxy ethanesulfonate | + | + | + | + | + | + | + | + | + | + | + | + | + | + | + | + |
| 20 | Int-d.50 | Kristina | Gamma-rays | + | + | + | + | + | + | + | + | + | + | + | + | + | + | + | + |
| 21 | Int-d.57 | Kristina | Iso-Propyl methanesulfonate | + | + | + | + | + | + | + | + | + | + | + | + | + | + | + | + |
| 22 | Int-d.67 | Kristina | Ethyl methanesulfonate | + | + | + | + | + | + | + | + | + | + | + | + | + | + | + | + |
| 23 | Int-d.68 | Kristina | Ethyl methanesulfonate | + | + | + | + | + | + | + | + | + | + | + | + | + | + | + | + |
| 24 | Int-d.69 | Kristina | Ethyl methanesulfonate | + | + | + | + | + | + | + | + | + | + | + | + | + | + | + | + |
| 25 | Int-d.73 | Bonus | Ethyl methanesulfonate | + | + | + | + | + | + | + | + | + | + | + | + | + | + | + | + |
| 27 | Int-d.82 | Bonus | Ethyl methanesulfonate | + | + | + | + | + | + | + | + | + | + | + | + | + | + | + | + |
| 28 | hex-v.03 | Bonus | Neutrons | + | − | − | − | − | − | + | + | + | + | + | + | + | + | + | + |
| 29 | hex-v.04 | Bonus | X-rays | + | + | + | + | + | + | + | + | + | + | + | + | + | + | + | + |
| 34 | hex-v.10 | Bonus | X-rayed pollen | + | − | − | − | − | − | + | + | + | + | + | + | + | + | + | + |
| 35 | hex-v.11 | Bonus | X-rayed pollen | + | − | − | − | − | − | + | + | + | + | + | + | + | + | + | + |
| 36 | hex-v.12 | Bonus | Neutrons | + | + | + | + | + | + | + | + | + | + | + | + | + | + | + | + |
| 37 | hex-v.13 | Foma | X-rays | + | + | + | + | + | + | + | + | + | + | + | + | + | + | + | + |
| 38 | hex-v.14 | Foma | Glycidol | + | + | + | + | + | + | + | + | + | + | + | + | + | + | + | + |

FIG. 3-2

| Code | Name | Origin | Mutagen | CF317052 | E30 | 351N10-T7(203-392) | STS2 | E42 | 111L15f1F | 699N11-T7(U179-L402) | 185K11-T7(U07/L213) | 572D24-fc-R(U01/L407) | E18 | end3 | BC12348 | BC1206 | BC05376 | GAN007 | BC14030 |
|---|---|---|---|---|---|---|---|---|---|---|---|---|---|---|---|---|---|---|---|
| 39 | hex-v.15 | Foma | Gamma-rays | + | + | + | + | + | + | + | + | + | + | + | + | + | + | + | + |
| 41 | hex-v.17 | Foma | Ethyl methanesulfonate | + | + | + | + | + | + | + | + | + | + | + | + | + | + | + | + |
| 42 | hex-v.18 | Bonus | X-rays | + | + | − | − | − | − | − | − | − | − | + | + | + | + | + | + |
| 43 | hex-v.19 | Foma | Methyl methanesulfonate | + | + | + | + | + | + | + | + | + | + | + | + | + | + | + | + |
| 44 | hex-v.21 | Foma | Ethyl methanesulfonate | + | + | + | + | + | + | + | + | + | + | + | + | + | + | + | + |
| 45 | hex-v.22 | Foma | Neutrons + Ethyl methanesulfonate | + | + | + | + | + | + | + | + | + | + | + | + | + | + | + | + |
| 46 | hex-v.23 | Foma | Ethylene imine | + | + | + | + | + | + | + | + | + | + | + | + | + | + | + | + |
| 47 | hex-v.24 | Foma | Propanedisulfonic acid diethyl ester | + | + | + | + | + | + | + | + | + | + | + | + | + | + | + | + |
| 48 | hex-v.25 | Foma | Ethylene imine | + | + | + | + | + | + | + | + | + | + | + | + | + | + | + | + |
| 49 | hex-v.26 | Foma | Ethyl methanesulfonate | + | + | + | + | + | + | + | + | + | + | + | + | + | + | + | + |
| 50 | hex-v.27 | Foma | N-ethyl-N-nitrosourea | + | + | + | + | + | + | + | + | + | + | + | + | + | + | + | + |
| 51 | hex-v.28 | Foma | Ethylene imine | + | + | + | + | + | + | + | + | + | + | + | + | + | + | + | + |
| 52 | hex-v.29 | Foma | Ethylene imine | + | + | + | + | + | + | + | + | + | + | + | + | + | + | + | + |
| 53 | hex-v.30 | Foma | Gamma-rays | + | + | + | + | + | + | + | + | + | + | + | + | + | + | + | + |
| 54 | hex-v.31 | Foma | Ethylene imine | + | + | + | + | + | + | + | + | + | + | + | + | + | + | + | + |
| 56 | hex-v.35 | Foma | Gamma-rays | + | − | − | − | − | − | + | + | + | + | + | + | + | + | + | + |
| 57 | hex-v.36 | Kristina | Ethyl methanesulfonate | + | + | + | + | + | + | + | + | + | + | + | + | + | + | + | + |
| 58 | hex-v.38 | Kristina | Iso-Propyl methanesulfonate | + | + | + | + | + | + | + | + | + | + | + | + | + | + | + | + |
| 59 | hex-v.39 | Kristina | Iso-Propyl methanesulfonate | + | + | + | + | + | + | + | + | + | + | + | + | + | + | + | + |
| 60 | hex-v.41 | Kristina | Neutrons | + | − | − | − | − | − | − | − | − | − | − | − | − | + | + | + |
| 61 | hex-v.42 | Kristina | Neutrons | + | + | + | + | + | + | + | + | + | + | + | + | + | + | + | + |
| 62 | hex-v.43 | Kristina | Ethyl methanesulfonate | + | + | + | + | + | + | + | + | + | + | + | + | + | + | + | + |
| 63 | hex-v.44 | Bonus | Iso-Propyl methanesulfonate | + | + | + | + | + | + | + | + | + | + | + | + | + | + | + | + |
| 64 | hex-v.45 | Bonus | Iso-Propyl methanesulfonate | + | + | + | + | + | + | + | + | + | + | + | + | + | + | + | + |
| 68 | hex-v.49 | Bonus | Sodium azide | + | + | + | + | + | + | + | + | + | + | + | + | + | + | + | + |

FIG. 4-1

| Mutagen | Origin | Bonus | Exon 1 | | | | Intron 1 | | | | Exon 2 | | | | | | | |
|---|---|---|---|---|---|---|---|---|---|---|---|---|---|---|---|---|---|---|
| | | | GAT | Asp | TCC | Ser | G | 1415 | A | 1293 | CAG | Gln | GAT | Asp | GCG | Ala | GGA | Gly |
| | | | | 8 | | 10 | | | | | | 24 | | 26 | | 40 | | 55 |
| | | | | | | | | | | | | | | | | | | |
| Neutrons | Bonus | hex-v.3 | (a) | | | | | | | | | | | | | | | |
| X-rayed pollen | Bonus | hex-v.10 | (a) | | | | | | | | | | | | | | | |
| X-rayed pollen | Bonus | hex-v.11 | (a) | | | | | | | | | | | | | | | |
| X-rays | Bonus | hex-v.18 | (a) | | | | | | | | | | | | | | | |
| Gamma-rays | Foma | hex-v.35 | (a) | | | | | | | | | | | | | | | |
| Neutrons | Kristina | hex-v.41 | (a) | | | | | | | | | | | | | | | |
| Gamma-rays | Foma | hex-v.15 | (b) | | | | | | | | | | | | | | | |
| X-rays | Bonus | hex-v.4 | | | TC- | FS | | | | | | | | | | | | |
| Sodium azide | Bonus | hex-v.49 | | | | | A | (c) | | | | | | | | | | |
| iso-Propyl methanesulfonate | Kristina | hex-v.38 | | | | | | | C | (d) | | | | | | | | |
| Ethyl methanesulfonate | Foma | hex-v.17 | | | | | | | | | TAG | Stop | | | | | | |
| iso-Propyl methanesulfonate | Bonus | hex-v.44 | | | | | | | | | | | | | | | TGA | Stop |
| iso-Propyl methanesulfonate | Bonus | hex-v.45 | | | | | | | | | | | | | | | TGA | Stop |
| Neutrons | Bonus | hex-v.12 | | | | | | | | | | | | | | | | |
| X-rays | Foma | hex-v.13 | | | | | | | | | | | | | | | | |
| Glycidol | Foma | hex-v.14 | | | | | | | | | | | | | | | | |
| Ethylene imine | Foma | Int-d.12 | | | | | | | | | | | | | | | | |
| iso-Propyl methanesulfonate | Foma | Int-d.28 | | | | | | | | | | | | | | | | |

FIG. 4-2

| Mutagen | Origin | Bonus | Exon 1 | | | | Intron 1 | | | | Exon 2 | | | | | | | |
|---|---|---|---|---|---|---|---|---|---|---|---|---|---|---|---|---|---|---|
| | | | GAT | Asp | TCC | Ser | G | 1415 | A | 1293 | CAG | Gln | GAT | Asp | GCG | Ala | GGA | Gly |
| | | | | 8 | | 10 | | | | | | 24 | | 26 | | 40 | | 55 |
| | | | | | | | | | | | | | | | | | | |
| iso-Propyl methanesulfonate | Kristina | hex-v.39 | | | | | | | | | | | | | | | | |
| Gamma-rays | Kristina | Int-d.50 | | | | | | | | | | | | | | | | |
| Ethyl methanesulfonate | Kristina | hex-v.36 | | | | | | | | | | | | | | | | |
| Ethylene imine | Foma | hex-v.25 | | | | | | | | | | | | | | | | |
| Ethyl methanesulfonate | Foma | hex-v.26 | | | | | | | | | | | | | | | | |
| Ethylene imine | Foma | hex-v.28 | | | | | | | | | | | | | | | | |
| Ethyl methanesulfonate | Kristina | Int-d.68 | | | | | | | | | | | | | | | | |
| Ethylene imine | Foma | hex-v.29 | | | | | | | | | | | | | | | | |
| Ethyl methanesulfonate | Kristina | Int-d.67 | | | | | | | | | | | | | | | | |
| Ethyl hydroxy ethanesulfonate | Kristina | Int-d.41 | | | | | | | | | | | | | | | | |
| Neutrons | Kristina | hex-v.42 | | | | | | | | | | | | | | | | |
| Ethyl methanesulfonate | Kristina | hex-v.43 | | | | | | | | | | | | | | | | |
| Methyl methanesulfonate | Foma | Int-d.22 | | | | | | | | | | | | | | | | |
| Buthyl methanesulfonate | Foma | Int-d.24 | | | | | | | | | | | | | | | | |
| Neutrons + Ethyl methanesulfonate | Foma | hex-v.22 | | | | | | | | | | | | | | | | |
| Ethylene imine | Foma | hex-v.23 | | | | | | | | | | | | | | | | |
| Propanedisulfonic acid diethyl ester | Foma | hex-v.24 | | | | | | | | | | | | | | | | |
| iso-Propyl methanesulfonate | Kristina | Int-d.57 | | | | | | | | | | | | | | | | |
| Ethyl methanesulfonate | Bonus | Int-d.73 | | | | | | | | | | | | | | | | |

FIG. 4-3

| Mutagen | Origin | Bonus | Exon 1 | | | | Intron 1 | | | | Exon 2 | | | | | | | |
|---|---|---|---|---|---|---|---|---|---|---|---|---|---|---|---|---|---|---|
| | | | GAT | Asp | TCC | Ser | G | 1415 | A | 1293 | CAG | Gln | GAT | Asp | GCG | Ala | GGA | Gly |
| | | | | 8 | | 10 | | | | | | 24 | | 26 | | 40 | | 55 |
| | | | | | | | | | | | | | | | | | | |
| Ethyl methanesulfonate | Foma | hex-v.21 | | | | | | | | | | | | | | | | |
| Methyl methanesulfonate | Foma | hex-v.19 | | | | | | | | | | | | | | | | |
| Ethyl methanesulfonate | Bonus | Int-d.82 | | | | | | | | | | | | | | | | |
| Ethyl methanesulfonate | Kristina | Int-d.69 | | | | | | | | | | | | | | | | |
| Ethylene imine | Foma | Int-d.11 | | | | | | | | | | | | | | | | |
| Ethyl methanesulfonate | Foma | Int-d.36 | | | | | | | | | | | | | | | | |
| Ethyl methanesulfonate | Kristina | Int-d.40 | | | | | | | | | | | | | | | | |
| N-ethyl-N-nitrosourea | Foma | hex-v.27 | | | | | | | | | | | | | | | | |
| Gamma-rays | Foma | hex-v.30 | | | | | | | | | | | | | | | | |
| Ethylene imine | Foma | hex-v.31 | | | | | | | | | | | | | | | | |
| | | Natsudaikon | | | | | | | | | | | | | | | | |
| | | Morex | GGT | Gly | | | | | | | | | GAG | Glu | | | | |
| | | AZ | GGT | Gly | | | | | | | | | GAG | Glu | | | | |
| | | Soren | GGT | Gly | | | | | | | | | GAG | Glu | | | | |
| | | Caveda | GGT | Gly | | | | | | | | | GAG | Glu | GCTG | FS | | |
| | | Dissa | GGT | Gly | | | | | | | | | GAG | Glu | GCTG | FS | | |
| | | Hayakiso | GGT | Gly | | | | | | | | | GAG | Glu | | | | |
| | | Arlington | GGT | Gly | | | | | | | | | GAG | Glu | | | | |
| | | PI284755 | GGT | Gly | | | | | | | | | GAG | Glu | | | | |
| | | OUH743 | GGT | Gly | | | | | | | | | GAG | Glu | | | | |
| | | OUH602 | GGT | Gly | | | | | | | | | GAG | Glu | | | | |
| | | debre | GGT | Gly | | | | | | | | | GAG | Glu | | | | |

FIG. 4-4

| Bonus | Homeodomain | | | | | | | | | | | | | | | | | | | | | | | | | |
|---|---|---|---|---|---|---|---|---|---|---|---|---|---|---|---|---|---|---|---|---|---|---|---|---|---|---|
| | TTC | Phe 75 | CGC | Arg 85 | CTG | leu 89 | GCC | Ala 90 | CTC | Leu 93 | CTG | Leu 95 | GCC | Ala 101 | TGG | Trp 103 | CAG | Gln 105 | AAC | Asn 106 | CGC | Arg 107 | CGC | Arg 110 | AAG | Lys 114 |
| | | 24 | | 34 | | 38 | | 39 | | 42 | | 44 | | 50 | | 52 | | 54 | | 55 | | 56 | | 59 | | 63 |
| hex-v.3 | | | | | | | | | | | | | | | | | | | | | | | | | | |
| hex-v.10 | | | | | | | | | | | | | | | | | | | | | | | | | | |
| hex-v.11 | | | | | | | | | | | | | | | | | | | | | | | | | | |
| hex-v.18 | | | | | | | | | | | | | | | | | | | | | | | | | | |
| hex-v.35 | | | | | | | | | | | | | | | | | | | | | | | | | | |
| hex-v.41 | | | | | | | | | | | | | | | | | | | | | | | | | | |
| hex-v.15 | | | | | | | | | | | | | | | | | | | | | | | | | | |
| hex-v.4 | | | | | | | | | | | | | | | | | | | | | | | | | | |
| hex-v.49 | | | | | | | | | | | | | | | | | | | | | | | | | | |
| hex-v.38 | | | | | | | | | | | | | | | | | | | | | | | | | | |
| hex-v.17 | | | | | | | | | | | | | | | | | | | | | | | | | | |
| hex-v.44 | | | | | | | | | | | | | | | | | | | | | | | | | | |
| hex-v.45 | | | | | | | | | | | | | | | | | | | | | | | | | | |
| hex-v.12 | ATC | Ile | | | | | | | | | | | | | | | | | | | | | | | | |
| hex-v.13 | ATC | Ile | | | | | | | | | | | | | | | | | | | | | | | | |
| hex-v.14 | ATC | Ile | | | | | | | | | | | | | | | | | | | | | | | | |
| Int-d.12 | | | CAC | His | | | | | | | | | | | | | | | | | | | | | | |
| Int-d.28 | | | CAC | His | | | | | | | | | | | | | | | | | | | | | | |

FIG. 4-5

| Bonus | Homeodomain | | | | | | | | | | | | | | | | | | | | | | | | | |
|---|---|---|---|---|---|---|---|---|---|---|---|---|---|---|---|---|---|---|---|---|---|---|---|---|---|---|
| | TTC | Phe | CGC | Arg | CTG | leu | GCC | Ala | CTC | Leu | CTG | Leu | GCC | Ala | TGG | Trp | CAG | Gln | AAC | Asn | CGC | Arg | CGC | Arg | AAG | Lys |
| | | 75 | | 85 | | 89 | | 90 | | 93 | | 95 | | 101 | | 103 | | 105 | | 106 | | 107 | | 110 | | 114 |
| | | 24 | | 34 | | 38 | | 39 | | 42 | | 44 | | 50 | | 52 | | 54 | | 55 | | 56 | | 59 | | 63 |
| hex-v.39 | | | | | CAG | Gln | | | | | | | | | | | | | | | | | | | | |
| Int-d.50 | | | | | CAG | Gln | | | | | | | | | | | | | | | | | | | | |
| hex-v.36 | | | | | | | GTC | Val | | | | | | | | | | | | | | | | | | |
| hex-v.25 | | | | | | | | | CAC | His | | | | | | | | | | | | | | | | |
| hex-v.26 | | | | | | | | | CAC | His | | | | | | | | | | | | | | | | |
| hex-v.28 | | | | | | | | | | | CAG | Gln | | | | | | | | | | | | | | |
| Int-d.68 | | | | | | | | | | | CAG | Gln | | | | | | | | | | | | | | |
| hex-v.29 | | | | | | | | | | | | | | | AGG | Arg | | | | | | | | | | |
| Int-d.67 | | | | | | | | | | | | | | | | | TAG | Stop | | | | | | | | |
| Int-d.41 | | | | | | | | | | | | | | | | | | | TAC | Tyr | | | | | | |
| hex-v.42 | | | | | | | | | | | | | | | | | | | | | CTC | Leu | | | | |
| hex-v.43 | | | | | | | | | | | | | | | | | | | | | CTC | Leu | | | | |
| Int-d.22 | | | | | | | | | | | | | | | | | | | | | | | CAC | His | | |
| Int-d.24 | | | | | | | | | | | | | | | | | | | | | | | CAC | His | | |
| hex-v.22 | | | | | | | | | | | | | | | | | | | | | | | | | TAG | Stop |
| hex-v.23 | | | | | | | | | | | | | | | | | | | | | | | | | TAG | Stop |
| hex-v.24 | | | | | | | | | | | | | | | | | | | | | | | | | TAG | Stop |
| Int-d.57 | | | | | | | | | | | | | | | | | | | | | | | | | | |
| Int-d.73 | | | | | | | | | | | | | | | | | | | | | | | | | | |
| hex-v.21 | | | | | | | | | | | | | | | | | | | | | | | | | | |

FIG. 4-6

| Bonus | Homeodomain | | | | | | | | | | | | | | | | | | | | | | | | | |
|---|---|---|---|---|---|---|---|---|---|---|---|---|---|---|---|---|---|---|---|---|---|---|---|---|---|---|
| | TTC | Phe | CGC | Arg | CTG | leu | GCC | Ala | CTC | Leu | CTG | Leu | GCC | Ala | TGG | Trp | CAG | Gln | AAC | Asn | CGC | Arg | CGC | Arg | AAG | Lys |
| | | 75 | | 85 | | 89 | | 90 | | 93 | | 95 | | 101 | | 103 | | 105 | | 106 | | 107 | | 110 | | 114 |
| | | 24 | | 34 | | 38 | | 39 | | 42 | | 44 | | 50 | | 52 | | 54 | | 55 | | 56 | | 59 | | 63 |
| hex-v.19 | | | | | | | | | | | | | | | | | | | | | | | | | | |
| Int-d.82 | | | | | | | | | | | | | | | | | | | | | | | | | | |
| Int-d.69 | | | | | | | | | | | | | | | | | | | | | | | | | | |
| Int-d.11 | | | | | | | | | | | | | | | | | | | | | | | | | | |
| Int-d.36 | | | | | | | | | | | | | | | | | | | | | | | | | | |
| Int-d.40 | | | | | | | | | | | | | | | | | | | | | | | | | | |
| hex-v.27 | | | | | | | | | | | | | | | | | | | | | | | | | | |
| hex-v.30 | | | | | | | | | | | | | | | | | | | | | | | | | | |
| hex-v.31 | | | | | | | | | | | | | | | | | | | | | | | | | | |
| Natsudaikon | TTG | Leu | | | | | | | | | | | | | | | | | | | | | | | | |
| Morex | | | | | | | | | | | | | | | | | | | | | | | | | | |
| AZ | | | | | | | | | | | | | | | | | | | | | | | | | | |
| Soren | | | | | | | | | | | | | | | | | | | | | | | | | | |
| Caveda | | | | | | | | | | | | | | | | | | | | | | | | | | |
| Dissa | | | | | | | | | | | | | | | | | | | | | | | | | | |
| Hayakiso | | | | | | | | | | | | | | | | | | | | | | | | | | |
| Arlington | | | | | | | | | | | | | | | | | | | | | | | | | | |
| PI284755 | | | | | | | | | | | | | | | | | | | | | | | | | | |
| OUH743 | | | | | | | | | | | | | GTC | Val | | | | | | | | | | | | |
| OUH602 | | | | | | | | | | | | | | | | | | | | | | | | | | |
| debre | | | | | | | | | | | | | | | | | | | | | | | | | | |

FIG. 4-7

| Bonus | Leucin zipper | | | | | | | | Intron 2 | |
|---|---|---|---|---|---|---|---|---|---|---|
| | GCC | Ala | CAC | His | AAA | Lys | GAG | Glu | G | 837 |
| | | 130 | | 133 | | 134 | | 140 | | |
| | | | | | | | | | | |
| hex-v.3 | | | | | | | | | | |
| hex-v.10 | | | | | | | | | | |
| hex-v.11 | | | | | | | | | | |
| hex-v.18 | | | | | | | | | | |
| hex-v.35 | | | | | | | | | | |
| hex-v.41 | | | | | | | | | | |
| hex-v.15 | | | | | | | | | | |
| hex-v.4 | | | | | | | | | | |
| hex-v.49 | | | | | | | | | | |
| hex-v.38 | | | | | | | | | | |
| hex-v.17 | | | | | | | | | | |
| hex-v.44 | | | | | | | | | | |
| hex-v.45 | | | | | | | | | | |
| hex-v.12 | | | | | | | | | | |
| hex-v.13 | | | | | | | | | | |
| hex-v.14 | | | | | | | | | | |
| Int-d.12 | | | | | | | | | | |
| Int-d.28 | | | | | | | | | | |
| hex-v.39 | | | | | | | | | | |
| Int-d.50 | | | | | | | | | | |
| hex-v.36 | | | | | | | | | | |
| hex-v.25 | | | | | | | | | | |
| hex-v.26 | | | | | | | | | | |
| hex-v.28 | | | | | | | | | | |
| Int-d.68 | | | | | | | | | | |
| hex-v.29 | | | | | | | | | | |
| Int-d.67 | | | | | | | | | | |
| Int-d.41 | | | | | | | | | | |

FIG. 4-8

| Bonus | Leucin zipper | | | | | | | | Intron 2 | |
|---|---|---|---|---|---|---|---|---|---|---|
| | GCC | Ala | CAC | His | AAA | Lys | GAG | Glu | G | 837 |
| | | 130 | | 133 | | 134 | | 140 | | |
| | | | | | | | | | | |
| hex-v.42 | | | | | | | | | | |
| hex-v.43 | | | | | | | | | | |
| Int-d.22 | | | | | | | | | | |
| Int-d.24 | | | | | | | | | | |
| hex-v.22 | | | | | | | | | | |
| hex-v.23 | | | | | | | | | | |
| hex-v.24 | | | | | | | | | | |
| Int-d.57 | | | CCC | Pro | | | | | | |
| Int-d.73 | | | CCC | Pro | | | | | | |
| hex-v.21 | | | | | TAA | Stop | | | | |
| hex-v.19 | | | | | | | TAG | Stop | | |
| Int-d.82 | | | | | | | | | A | (e) |
| Int-d.69 | | | | | | | | | | |
| Int-d.11 | | | | | | | | | | |
| Int-d.36 | | | | | | | | | | |
| Int-d.40 | | | | | | | | | | |
| hex-v.27 | | | | | | | | | | |
| hex-v.30 | | | | | | | | | | |
| hex-v.31 | | | | | | | | | | |
| Natsudaikon | | | | | | | | | | |
| Morex | | | | | | | | | | |
| AZ | | | | | | | | | | |
| Soren | | | | | | | | | | |
| Caveda | | | | | | | | | | |
| Dissa | | | | | | | | | | |
| Hayakiso | | | | | | | | | | |
| Arlington | | | | | | | | | | |
| PI284755 | | | | | | | | | | |
| OUH743 | | | | | | | | | | |
| OUH602 | GCT | Ala | | | | | | | | |
| debre | | | | | | | | | | |

FIG. 4-9

| Bonus | Exon 3 | | | | | | | | | | | | | | | | | | | | | |
|---|---|---|---|---|---|---|---|---|---|---|---|---|---|---|---|---|---|---|---|---|---|---|
| | AGA | Arg | GCG | Ala | GAG | Glu | AGC | Ser | TCT | Ser | GGC | Gly | AGC | Ser | TGC | Cys | CAG | Gln | CAG | Gln | CAGACGTGCTG | |
| | | 147 | | 150 | | 152 | | 164 | | 168 | | 176 | | 184 | | 194 | | 196 | | 197 | | |
| | | | | | | | | | | | | | | | | | | | | | | |
| hex-v.3 | | | | | | | | | | | | | | | | | | | | | | |
| hex-v.10 | | | | | | | | | | | | | | | | | | | | | | |
| hex-v.11 | | | | | | | | | | | | | | | | | | | | | | |
| hex-v.18 | | | | | | | | | | | | | | | | | | | | | | |
| hex-v.35 | | | | | | | | | | | | | | | | | | | | | | |
| hex-v.41 | | | | | | | | | | | | | | | | | | | | | | |
| hex-v.15 | | | | | | | | | | | | | | | | | | | | | | |
| hex-v.4 | | | | | | | | | | | | | | | | | | | | | | |
| hex-v.49 | | | | | | | | | | | | | | | | | | | | | | |
| hex-v.38 | | | | | | | | | | | | | | | | | | | | | | |
| hex-v.17 | | | | | | | | | | | | | | | | | | | | | | |
| hex-v.44 | | | | | | | | | | | | | | | | | | | | | | |
| hex-v.45 | | | | | | | | | | | | | | | | | | | | | | |
| hex-v.12 | | | | | | | | | | | | | | | | | | | | | | |
| hex-v.13 | | | | | | | | | | | | | | | | | | | | | | |
| hex-v.14 | | | | | | | | | | | | | | | | | | | | | | |
| Int-d.12 | | | | | | | | | | | | | | | | | | | | | | |
| Int-d.28 | | | | | | | | | | | | | | | | | | | | | | |
| hex-v.39 | | | | | | | | | | | | | | | | | | | | | | |

FIG. 4-10

| Bonus | Exon 3 | | | | | | | | | | | | | | | | | | | | | |
|---|---|---|---|---|---|---|---|---|---|---|---|---|---|---|---|---|---|---|---|---|---|---|
| | AGA | Arg | GCG | Ala | GAG | Glu | AGC | Ser | TCT | Ser | GGC | Gly | AGC | Ser | TGC | Cys | CAG | Gln | CAG | Gln | CAGACGTGCTG | |
| | | 147 | | 150 | | 152 | | 164 | | 168 | | 176 | | 184 | | 194 | | 196 | | 197 | | |
| | | | | | | | | | | | | | | | | | | | | | | |
| Int-d.50 | | | | | | | | | | | | | | | | | | | | | | |
| hex-v.36 | | | | | | | | | | | | | | | | | | | | | | |
| hex-v.25 | | | | | | | | | | | | | | | | | | | | | | |
| hex-v.26 | | | | | | | | | | | | | | | | | | | | | | |
| hex-v.28 | | | | | | | | | | | | | | | | | | | | | | |
| Int-d.68 | | | | | | | | | | | | | | | | | | | | | | |
| hex-v.29 | | | | | | | | | | | | | | | | | | | | | | |
| Int-d.67 | | | | | | | | | | | | | | | | | | | | | | |
| Int-d.41 | | | | | | | | | | | | | | | | | | | | | | |
| hex-v.42 | | | | | | | | | | | | | | | | | | | | | | |
| hex-v.43 | | | | | | | | | | | | | | | | | | | | | | |
| Int-d.22 | | | | | | | | | | | | | | | | | | | | | | |
| Int-d.24 | | | | | | | | | | | | | | | | | | | | | | |
| hex-v.22 | | | | | | | | | | | | | | | | | | | | | | |
| hex-v.23 | | | | | | | | | | | | | | | | | | | | | | |
| hex-v.24 | | | | | | | | | | | | | | | | | | | | | | |
| Int-d.57 | | | | | | | | | | | | | | | | | | | | | | |
| Int-d.73 | | | | | | | | | | | | | | | | | | | | | | |
| hex-v.21 | | | | | | | | | | | | | | | | | | | | | | |
| hex-v.19 | | | | | | | | | | | | | | | | | | | | | | |
| Int-d.82 | | | | | | | | | | | | | | | | | | | | | | |

FIG. 4-11

| Bonus | Exon 3 | | | | | | | | | | | | | | | | | | | | | |
|---|---|---|---|---|---|---|---|---|---|---|---|---|---|---|---|---|---|---|---|---|---|
| | AGA | Arg | GCG | Ala | GAG | Glu | AGC | Ser | TCT | Ser | GGC | Gly | AGC | Ser | TGC | Cys | CAG | Gln | CAG | Gln | CAGACGTGCTG | |
| | | 147 | | 150 | | 152 | | 164 | | 168 | | 176 | | 184 | | 194 | | 196 | | 197 | | |
| | | | | | | | | | | | | | | | | | | | | | | |
| Int-d.69 | TGA | Stop | | | | | | | | | | | | | | | | | | | | |
| Int-d.11 | | | | | | | | | | | | | | | AGC | Ser | | | | | | |
| Int-d.36 | | | | | | | | | | | | | | | | | TAG | Stop | | | | |
| Int-d.40 | | | | | | | | | | | | | | | | | | | TAG | Stop | | |
| hex-v.27 | | | | | | | | | | | | | | | | | | | | | Deletion | FS |
| hex-v.30 | | | | | | | | | | | | | | | | | | | | | Deletion | FS |
| hex-v.31 | | | | | | | | | | | | | | | | | | | | | Deletion | FS |
| Natsudaikon | | | | | | | | | | | | | | | | | | | | | | |
| Morex | | | | | GA- | FS | | | | | | | | | | | | | | | | |
| AZ | | | | | GA- | FS | | | | | | | | | | | | | | | | |
| Soren | | | | | GA- | FS | | | | | | | | | | | | | | | | |
| Caveda | | | | | | | | | | | | | | | | | | | | | | |
| Dissa | | | | | | | | | | | | | | | | | | | | | | |
| Hayakiso | | | | | | | | | | | | | | | | | | | | | | |
| Arlington | | | | | | | | | | | | | | | | | | | | | | |
| PI284755 | | | | | | | | | TCC | Ser | | | | | | | | | | | | |
| OUH743 | | | | | | | | | | | | | | | | | | | | | | |
| OUH602 | | | GCA | Ala | | | ACC | Thr | | | GAC | Asp | | | | | | | | | | |
| debre | | | | | | | | | | | | | GGC | Gly | | | | | | | | |

SEQUENCE LISTING

```
<160> NUMBER OF SEQ ID NOS: 77

<210> SEQ ID NO 1
<211> LENGTH: 2147
<212> TYPE: DNA
<213> ORGANISM: Hordeum vulgare

<400> SEQUENCE: 1

gtcataactc ggcaaacata gattagacag aattttctga gttcttatct agaggaactc     60

gatgaacttg aggcattgtc gaggttcttc ctttcaccga gtactttttt gcgtgtacta    120

ggcaaatata tgaagtttgt gagtttcgga tcaccaccga gtgcaagttt ggaccaaact    180

tgacaaatac ataagtttgg cgagctccga atgaaatgaa ctctgcaaaa gaatagaact    240

cggcgcaaaa ccagattcta atagtgtgtg aatttttggg ctgttttgta taaatatgat    300

gaaacttagt aaaatttcac tcaggtcaat gctaatgtgg agagtaaata aaaaatgaag    360

ggagtacttg gctgcatcat atgtttgccc ccgatcacct tcacatctcc ccgtccggac    420

ggcctggatc ggaaagcact cagccggagc cccgccggcg cttgccgttg ggtacctctg    480

ccacctattt atattacccc taggtctctc cctggagaca cgcactcccc tccttcaact    540

agtgctttgc ggcccgtggt cctcctctcg atccagttcc tgagcacacc aacaggcaac    600

agaacaacct accgtgtctc ccctccaatc tcctcacgat cccttctttc cctcagatcc    660

gaaccgaaag catggacaag catcagctct ttgattcatc caacgtggac acgactttct    720

tcgcggccaa tggtacacac gacgccgcgc gcgcccggtc tttgcgcatg cgatgatgca    780

gctgcagtag cttcagtttc accggccagg acacgcatgt gatgacgttt tttccattct    840

gtgtttgtat gtgcaggcac ggcgcagggg gataccagca agcagagggc gcggcgcagg    900

cggcggaggt cggcgaggtg cggcggaggg gatggtgacg gtggggagat ggacggagga    960

ggggaccccca agaagcggcg gctcaccgac gagcaggccg agattctgga gctgagcttc   1020

cgggaggacc gcaagctgga gacagcccgc aaggtgtatc tggccgccga gctcgggctg   1080

gaccccaagc aggtcgccgt gtggttccag aaccgccgcg cgcgccacaa gaacaagacg   1140

ctcgaggagg agttcgcgag gctcaagcac gcccacgacg ccgccatcct ccacaaatgc   1200

cacctcgaga acgaggtatg cttgctcgca tacactcaca ctggcttaca tatggcgctg   1260

cacatctgca gttcctctcc gttcttgaac atgcttactg acaaacatat ggccagctgc   1320

tgaggctgaa ggagagactg ggagcgactg agcaggaggt gcggcgcctc aggtcggcag   1380

ctgggagcca cggggcatct gtggatggcg gacacgccgc tggcgccgtt ggcgtgtgcg   1440

gcgggagccc gagctcgtcc ttctcgacgg gaacctgcca gcagcagccg ggtttcagcg   1500

gggcagacgt gctggggcgg gacgatgacc tgatgatgtg cgtccccgag tggtttttag   1560

catgaattag agtttatgct ggctaagccg atagcagcgt ggtcgagtgt tttttagcat   1620
```

-continued

```
gaaatcagat ctccatctcc cataaaatag ccgagatagc tgctgccgcc gccaaatcct   1680

ctatagggct tcaagatcgg cagaaacctc tagaaatcat ctccccccctc cggaaaagtc   1740

gcctctattt gtctccattg cccgcgatgc agcatccggt atagctgcta agacaggccg   1800

cccctaaatc gtttctccag cgattttaat ctttggtttt tagcctgtat atatgggctg   1860

tgatttgaag ttgagacgag ctggacatca actgcacgct gatcgattac tattctagtt   1920

tggcatagtg ttaattaagt ttggatgatc tctaggcgtg cgttaagtat gtagatagtg   1980

ttgattaatg gcaaaagctt gcaagttaag tgtagtattg gcagctctct tgaagatcaa   2040

atatgatgtg tgttatcatt tgatgatata tattttactt cagccgtaaa tagtcttctt   2100

agggaagcac tgtccatgta tgtgctggta gttggcaatc atctttc                2147


<210> SEQ ID NO 2
<211> LENGTH: 1227
<212> TYPE: DNA
<213> ORGANISM: Hordeum vulgare
<220> FEATURE:
<221> NAME/KEY: CDS
<222> LOCATION: (153)..(818)

<400> SEQUENCE: 2

acgcactccc ctccttcaac tagtgctttg cggcccgtgg tcctcctctc gatccagttc     60

ctgagcacac caacaggcaa cagaacaacc taccgtgtct cccctccaat ctcctcacga    120

tcccttcttt ccctcagatc cgaaccgaaa gc atg gac aag cat cag ctc ttt      173
                                    Met Asp Lys His Gln Leu Phe
                                     1               5

gat tca tcc aac gtg gac acg act ttc ttc gcg gcc aat ggc acg gcg      221
Asp Ser Ser Asn Val Asp Thr Thr Phe Phe Ala Ala Asn Gly Thr Ala
        10                  15                  20

cag ggg gat acc agc aag cag agg gcg cgg cgc agg cgg cgg agg tcg      269
Gln Gly Asp Thr Ser Lys Gln Arg Ala Arg Arg Arg Arg Arg Arg Ser
    25                  30                  35

gcg agg tgc ggc gga ggg gat ggt gac ggt ggg gag atg gac gga gga      317
Ala Arg Cys Gly Gly Gly Asp Gly Asp Gly Gly Glu Met Asp Gly Gly
40                  45                  50                  55

ggg gac ccc aag aag cgg cgg ctc acc gac gag cag gcc gag att ctg      365
Gly Asp Pro Lys Lys Arg Arg Leu Thr Asp Glu Gln Ala Glu Ile Leu
                60                  65                  70

gag ctg agc ttc cgg gag gac cgc aag ctg gag aca gcc cgc aag gtg      413
Glu Leu Ser Phe Arg Glu Asp Arg Lys Leu Glu Thr Ala Arg Lys Val
            75                  80                  85

tat ctg gcc gcc gag ctc ggg ctg gac ccc aag cag gtc gcc gtg tgg      461
Tyr Leu Ala Ala Glu Leu Gly Leu Asp Pro Lys Gln Val Ala Val Trp
        90                  95                  100

ttc cag aac cgc cgc gcg cgc cac aag aac aag acg ctc gag gag gag      509
Phe Gln Asn Arg Arg Ala Arg His Lys Asn Lys Thr Leu Glu Glu Glu
    105                 110                 115

ttc gcg agg ctc aag cac gcc cac gac gcc gcc atc ctc cac aaa tgc      557
Phe Ala Arg Leu Lys His Ala His Asp Ala Ala Ile Leu His Lys Cys
120                 125                 130                 135

cac ctc gag aac gag ctg ctg agg ctg aag gag aga ctg gga gcg act      605
His Leu Glu Asn Glu Leu Leu Arg Leu Lys Glu Arg Leu Gly Ala Thr
                140                 145                 150

gag cag gag gtg cgg cgc ctc agg tcg gca gct ggg agc cac ggg gca      653
Glu Gln Glu Val Arg Arg Leu Arg Ser Ala Ala Gly Ser His Gly Ala
            155                 160                 165

tct gtg gat ggc gga cac gcc gct ggc gcc gtt ggc gtg tgc ggc ggg      701
Ser Val Asp Gly Gly His Ala Ala Gly Ala Val Gly Val Cys Gly Gly
```

-continued

```
        170                 175                 180

agc ccg agc tcg tcc ttc tcg acg gga acc tgc cag cag cag ccg ggt      749
Ser Pro Ser Ser Ser Phe Ser Thr Gly Thr Cys Gln Gln Gln Pro Gly
    185                 190                 195

ttc agc ggg gca gac gtg ctg ggg cgg gac gat gac ctg atg atg tgc      797
Phe Ser Gly Ala Asp Val Leu Gly Arg Asp Asp Asp Leu Met Met Cys
200                 205                 210                 215

gtc ccc gag tgg ttt tta gca tgaattagag tttatgctgg ctaagccgat         848
Val Pro Glu Trp Phe Leu Ala
                220

agcagcgtgg tcgagtgttt tttagcatga aatcagatct ccatctccca taaaatagcc    908

gagatagctg ctgccgccgc caaatcctct atagggcttc aagatcggca gaaacctcta    968

gaaatcatct cccccctccg gaaaagtcgc ctctatttgt ctccattgcc cgcgatgcag   1028

catccggtat agctgctaag acaggccgcc cctaaatcgt ttctccagcg attttaatct   1088

ttggttttta gcctgtatat atgggctgtg atttgaagtt gagacgagct ggacatcaac   1148

tgcacgctga tcgattacta ttctagtttg gcatagtgtt aattaagttt ggatgatctc   1208

taggcgtgcg ttaagtatg                                                1227


<210> SEQ ID NO 3
<211> LENGTH: 222
<212> TYPE: PRT
<213> ORGANISM: Hordeum vulgare

<400> SEQUENCE: 3

Met Asp Lys His Gln Leu Phe Asp Ser Ser Asn Val Asp Thr Thr Phe
1               5                   10                  15

Phe Ala Ala Asn Gly Thr Ala Gln Gly Asp Thr Ser Lys Gln Arg Ala
            20                  25                  30

Arg Arg Arg Arg Arg Arg Ser Ala Arg Cys Gly Gly Gly Asp Gly Asp
        35                  40                  45

Gly Gly Glu Met Asp Gly Gly Gly Asp Pro Lys Lys Arg Arg Leu Thr
    50                  55                  60

Asp Glu Gln Ala Glu Ile Leu Glu Leu Ser Phe Arg Glu Asp Arg Lys
65                  70                  75                  80

Leu Glu Thr Ala Arg Lys Val Tyr Leu Ala Ala Glu Leu Gly Leu Asp
                85                  90                  95

Pro Lys Gln Val Ala Val Trp Phe Gln Asn Arg Arg Ala Arg His Lys
            100                 105                 110

Asn Lys Thr Leu Glu Glu Glu Phe Ala Arg Leu Lys His Ala His Asp
        115                 120                 125

Ala Ala Ile Leu His Lys Cys His Leu Glu Asn Glu Leu Leu Arg Leu
    130                 135                 140

Lys Glu Arg Leu Gly Ala Thr Glu Gln Glu Val Arg Arg Leu Arg Ser
145                 150                 155                 160

Ala Ala Gly Ser His Gly Ala Ser Val Asp Gly Gly His Ala Ala Gly
                165                 170                 175

Ala Val Gly Val Cys Gly Gly Ser Pro Ser Ser Ser Phe Ser Thr Gly
            180                 185                 190

Thr Cys Gln Gln Gln Pro Gly Phe Ser Gly Ala Asp Val Leu Gly Arg
        195                 200                 205

Asp Asp Asp Leu Met Met Cys Val Pro Glu Trp Phe Leu Ala
    210                 215                 220


<210> SEQ ID NO 4
```

<211> LENGTH: 427
<212> TYPE: DNA
<213> ORGANISM: Hordeum vulgare

<400> SEQUENCE: 4
gagatcggac ggccgccgtc gggaaccttc tcacccaata taatccctcc cctcctccca 60
cccctgcccc caatccatcg acctccgcca gccgattcca atccgtcggt ctccacatcc 120
cgatcggtcg caacccaagc ggaagcagcc agccggccca atcgcggcga tggcggccga 180
cgaggccaag gccaggggca acgcggcgtt ctcggcgggc cgcttcgagg aggcggcggg 240
ccacttcggg gacgccatcg cgctcgcccc cgacaaccac gtcctcttct ccaaccgctc 300
ggcggcctac gcctcgctcg gccgctacaa ggaggcgctc gccgacgccg accgcaccgt 360
cgcgctcagg cccgactggg ccaagggcta ctcccgcctc ggcgccgcgc gcctcgggtt 420
gggggac 427

<210> SEQ ID NO 5
<211> LENGTH: 2381
<212> TYPE: DNA
<213> ORGANISM: Hordeum vulgare

<400> SEQUENCE: 5
gcccgcgccc gcgcaggccg cgcctctcgg tcgtcgccat ggccggcaat gatcgccaag 60
tgcctttgga ggattaccgc aatattggta ttatggccca tatagatgcc ggcaaaacaa 120
caacaacaga gcgcattctc tattacactg gaaggaacta caaaattggt gaggttcatg 180
agggaacagc cactatggac tggatggagc aagaacagga gagaggaata accattacat 240
ctgcagcaac aactgccgtc tgggacaaac atagaatcaa cattattgat actcctgggc 300
acgtcgactt cactcttgag gttgaacgtg ctctcagggt tttggatggt gctatatgtc 360
tctttgacag tgttgctggg gtagaaccac aatctgaaac tgtgtggcgc caagcagata 420
agtacggagt tccaagaata tgttttgtaa acaaaatgga tcgccttgga gctaacttct 480
ttagaactag ggacatgata gtggcaaact tgggtgcaaa gcctttggtg atacagttgc 540
caattggttc agaggacaat ttccaaggag ttgttgatct aatcagaatg aaggctattg 600
tctggacagg agaggaactt ggtgcagaat tttcatacca agacatacct gctgatcttg 660
aggagttggc tcaagactat agacttcaga tgatggaaac tattgttgaa ttagatgatg 720
aagctatgga gggatatcta gaaggaaatg aaccagatga ggcaactgtg aagaaattaa 780
tcagaaaagg aacaataggt gccagctttg tccccatttt atgtggttcg gccttcaaaa 840
acaagggtgt ccagccattg cttgatgctg ttgttgatta cttgccatca ccactagacc 900
tgccaccaat gaagggtact gacccagacg acccggaagt ggttcttgaa agacttccta 960
gtgacgatga accattttct gggttagctt tcaagatcat gactgatcca tacgtggggt 1020
cactaacgtt tgtccgcata tactcaggga agctgatcgc tggctcatac gttctcaatg 1080
caaacaaaga taagaaggaa agaattggaa ggcttctaga gatgcatgca aacagtaagg 1140
aggatataac agttgcagtg acaggcgata tagtagctct tgctggtctg aaagatacaa 1200
ttaccggtga aacactctgt gacccagata accttgtggt gcttgaacgc atggaatttc 1260
ccgatcctgt cattaaggtt gctattgaac caaagaccaa agctgatgct gataaaatgg 1320
caaatggatt aataaagctt gctcaggaag atccatcatt ccacttctct agagacgagg 1380
aaactaacca gacagttatt gaaggaatgg gagaattaca ccttgacatc attgtagaca 1440
gattaaagag agagttcaag gttgaggcaa atgttggagc tccacaagtc aactaccgtg 1500

-continued

```
aaagtatttc caaaattgca gagactcagt atgtccacaa aaagcagtcc ggtggttcag   1560

ggcagtttgc agatattatt gtgcggtttg aacctatgga ggctggaagt gggtatgaat   1620

tcaagagtga aattaaggga ggggcagtgc caaaagaata cgtacccggt gtgatgaagg   1680

gaattgaaga aagcttaccc aacggtgtcc ttgctggtta cccagttgtg gatttacgag   1740

cagtgctggt tgatggctcc taccacgatg ttgattcaag tgtccttgcc ttccaaattg   1800

cagccagggg ggccttccgt gaaggattga gaaaagctgg cccacgactc ctggaaccta   1860

tcatgaaggt tgaagtgatt acccctgagg agcatttggg tgatgttatt ggtgacttga   1920

actctagaag agggcaagtt aacagcttcg gagataagcc aggtggactt aaggtggttg   1980

atgctttcgt gccgttggcc gagatgttcc agtatgtcag cagtctgagg ggaatgtcca   2040

aggggcgcgc gtcgtacaca atgcagcttg ccaagttcga cgttgtccca cagcatatcc   2100

agaaccaact ttctgcggca aaacaagagg aagctgctgc ttaaatcttc ggcattcgta   2160

gataatatat atgaggacgg cagagcaggt gagtatagga ggacatcaag gtgtatgtag   2220

ctttgtagta tcaaacccag tgggtgatat tatttgccat tgtttttgga cctgataatg   2280

tccataattt tgcaagctgg tataatttca taatgacctt gtcaagttct cacaaatgag   2340

aaaacagttt gttataagtt ttgcttacat gcttcagtcc a                       2381
```

<210> SEQ ID NO 6
<211> LENGTH: 1068
<212> TYPE: DNA
<213> ORGANISM: Hordeum vulgare

<400> SEQUENCE: 6

```
gggtacctgc agtcccctct gagggggggag tctgcaccgg tgaccatacc aggcgtgaga     60

aggagccccg tgcaccgtca gagcatgctg gacccggtta aaggtttaat gctgccaccg    120

ccatccccga ggagaggaga caagggagca gcaggttcac aagaatcgcc gtcagatata    180

agccggtcat tcgggaggcc agaaggactt aggatggggg atccatatgg cagctcatca    240

ccaggatcca agggtaagga cagtcgggat gaatctggca gattctctgc actctcttct    300

tgtgattcac cacggcaaga tgatctggat gaggcagatt atccttttgc tgtggatgat    360

gtcgatccac caatctccag acctgggagc agtgatggaa aggaggctgg agatcaggca    420

ggctcgtcgt cccataaatc acaagatgcg gcagtcggct ctctggttca cttgctgaga    480

accgcacgcc cgctgcgaga ttctagctat tcgtctcaaa cgtcaggtgc tgagtctaac    540

acagtagcct cgactagttc tgtcatgtct cgcaggacat ctgatgcact cgaggagctg    600

cagtctttca aagcaatcag ggagagactg ctgtccggga gtagagcgaa agagcgagac    660

tcgccggaga agccatagca ccattctttc cttgtttctc ttaacttcac ggtggaaggt    720

cagatccgta cgacagaaca ggccatgctg tgagcccagc aatgttttgt tggggcgttt    780

gtgtatataa ctgatgaatt gatatgctct tggtcgaaga taagatacag acctcgattg    840

atttcagcga gggcgtatct ctcgtcattc ttgaacccta ggactcgccg ctgtttatac    900

gctcttgtat acctgggaag taagatcagt acaacacgta ggtgtgagcc tttggctgaa    960

cgtagtgctc ttgcgctgtg tgcgtgtgta aattatatgt aactgtactg aagatcagta   1020

aacatcaatg ttaaaaaaaa agaaaaaaaa caaaaaaaaa aaaaaaaa                1068
```

<210> SEQ ID NO 7
<211> LENGTH: 548
<212> TYPE: DNA
<213> ORGANISM: Hordeum vulgare -continued

<400> SEQUENCE: 7

```
ttttttttt ttttttgta aagactgata gcaatctatg ttgaatgttt ctttcagaaa     60
ttgcacgtat gtaaacttgt tctgtactac tatgtctttg gaaacagacg aacacacctc    120
gtatcaaact tacaggatct tacatgtttg atctcccagc gcagtagaca gggttttcca    180
acgcactaca atatcataca gaaacacatt gaagggccta taagctacaa ctaacaacgc    240
tcctataatt ctatacccac caaggcgagg tgaggcgggg ggtgggggag gacaagggaa    300
caatgaaaac cttttgtgtt catttgcatc tcataatcag tccagggaag aacggccata    360
tctccagcta ttgtgggatc gtcggctgaa ctgctgcggc gcaaagctta gcccaaacat    420
ctccctcagc gcctttcctg gctccaggag gccgatcaat cgggcaacaa gggaagcgct    480
ctccctcaca tgctcgaggg ttttggtttc ggtccacagg cgacgagcca cctgaagcct    540
tctcctct                                                             548
```

<210> SEQ ID NO 8
<211> LENGTH: 604
<212> TYPE: DNA
<213> ORGANISM: Hordeum vulgare

<400> SEQUENCE: 8

```
ctcctgtacc ctggagcaca tctggagact gtcagaaaac cttttgccaa tcttgtcgaa     60
gatctagggt cttcaacacg aaacccgtcc agctctagag gaattgtcag aagcaggagc    120
tgtaggtctc tgatgggttc tactctcctt gaagacctgg agaaggagga ttgcacacca    180
ccaagcagaa gattcatgga cttccccggg agacctgaag gggtcaaag aaggggctct    240
gcgctgaact ttgatgcaga gagtgaaact ctgtcacggg cagggtcaat gctttctgaa    300
atcactacta cgaggggtgg acccaaggca aacggttcta ttgcaggtga cacggaattt    360
actggcatag gtgaatttgt tgctgaactg aaagaaatgg ctcagtatca gaagcaactc    420
ggtggtcagt atgttaatgg agaaatagca gaaggaaccg tcaggagcgt tggactagat    480
ccgatcatgg atgccttgca atcaccttcg cgatggccac tggaattcga gagaaaacag    540
caagagatca ttgacctttg gcatgcatgc tatgcttcac tggttcatag aacctacttt    600
ttct                                                                 604
```

<210> SEQ ID NO 9
<211> LENGTH: 840
<212> TYPE: DNA
<213> ORGANISM: Hordeum vulgare
<220> FEATURE:
<221> NAME/KEY: misc_feature
<222> LOCATION: (757)..(757)
<223> OTHER INFORMATION: n is a, c, g, or t
<220> FEATURE:
<221> NAME/KEY: misc_feature
<222> LOCATION: (770)..(770)
<223> OTHER INFORMATION: n is a, c, g, or t
<220> FEATURE:
<221> NAME/KEY: misc_feature
<222> LOCATION: (775)..(775)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (809)..(809)
<223> OTHER INFORMATION: n is a, c, g, or t
<220> FEATURE:
<221> NAME/KEY: misc_feature
<222> LOCATION: (825)..(825)

<223> OTHER INFORMATION: n is a, c, g, or t
<220> FEATURE:
<221> NAME/KEY: misc_feature
<222> LOCATION: (838)..(838)
<223> OTHER INFORMATION: n is a, c, g, or t

<400> SEQUENCE: 9
gaattcggca cgagaaggac agcaatcatt tgcacaatga gcccagcccg aagctacatg 60
gaacaatcaa gaaataccct gctatttgca agttgcgcga aggaagtagt tacaaacgca 120
caggttaatg tagtcatgtc tgataaagcc ctagttaagc atttacaaag agaacttgcc 180
aggctggaga gtgaactgcg atgtccagct acctattcca gtctagaagc attggtgaag 240
gaaaaagata accacatccg aaagatggag aaagaaatta aggagttgaa ggtacagcgt 300
gatctggctc agtctaggct gcaggatttg ctccaggttg ttggagataa ccatgtttca 360
aagcgccccc tggcttctgg gaggaacttt accttcgatg tgccccaccc ttgtgaagat 420
cagagatcaa caaccgaatc atcagaagta gtcgacaatg tccaaaattg taggttccaa 480
ggtcgccgtg cagcacaaaa ggaagttggg tctcaacagt cagaaaataa tgtgcagttt 540
gctaccccat tgagttattc agtcagcagt cccccgttca gtgggatgcc cccaaccacc 600
agcagagatg atgcttctca gatatcaaat gagggattca gatgatgttt tgcaaagaag 660
tacggtggta tagagaccca atggaaaccg gaagggaaaa catgggtttg ggactcggtc 720
agccatcagg aagcaatatc ttgcaagaat cgaatgnggg gtagccagtn tgccntgggg 780
aaagggatga ttcttggacc aagnatgang tatccttcct gggcnacccc ttgggaanca 840

<210> SEQ ID NO 10
<211> LENGTH: 627
<212> TYPE: DNA
<213> ORGANISM: Hordeum vulgare

<400> SEQUENCE: 10
cggcacgagg cacagtatca gacatttatg attacattgg ccggcacgag gagagagcat 60
ttgtgttgaa attctcagcg atagaaatat ataacgaagt tgtacgggat cttcttagtt 120
cagaaaacac ttctcttaga ctttgggatg acgcagagaa ggggacttat gtagagaacc 180
ttaaagaagt gatactgagg gactggaacc acctcaagga acttatttct gtgtgtgaag 240
ctcaaaggag aactggagag acatacttaa acgaaaacag ctccagatcg catcaaatcc 300
ttaaattgac tatcgaaagt tctgctcgtg aattcttggg caaggacaag tcaacgacac 360
ttgcggctag tgtgaacttt gtcgatttgg caggaagtga gcgtgcatct caggcactgt 420
cagctggtgc taggctgaag gaaggttgcc atattaatag aagtttactt accctaggaa 480
ctgtcatccg taaactaagc aaggtaagaa atggacacat accatatcgg gattcaaagc 540
tcacacgcat attacagcct tctctgggag gtaacgcaag gacagcattc atttgcacaa 600
tgagcccagc ccgaagctac atggaac 627

<210> SEQ ID NO 11
<211> LENGTH: 961
<212> TYPE: DNA
<213> ORGANISM: Hordeum vulgare

<400> SEQUENCE: 11
tccctctgta aggttctcta tatatgttcc cttctgtaga agtaaacagc agtggaccaa 60
aatcagtgca gtgggacagt aggatacctt ttcttttctc taaaatatat agctatttgt 120
tgttctcacc tctgcatcat cccaaagtct aagtgatgtg ttttctgcac taagaagatc 180

```
ccttacaact tcgttatata tttcaattgc tgaaaatttc aatacaaatg ctctctcttc    240
atgctgcaag aaaaaatgtc catgtgtata agtttgcaag cagaaatggt gccattttga    300
agacatgtta tgaattaaac cttaggaacg attatttggt aaccttgcca atgtaatcat    360
agatatctgc tgctgtatgt tccgttattc cagtcatggt gtatgttttt ccactacttg    420
tttgaccata tgcaaaaaca cttgctgtta catacagata aagggggaaa gaaaacacat    480
ttcagtgact tcatggagta ctttgattta aaaaaaatag agtaagatag aaagtaggtg    540
ttgagttaca gttaatgcca ctaactacag agagagcaac tgctttggcc ccttcctcat    600
atacttcttt ggtattacag tcagaacgaa ataccctatc tgcaaaagaa cagagttgtg    660
tcaaagaagt tacacacaac aacatagctg gaaaggaatg gactttgtag attgtagtgt    720
atacttgtgg aaagagcaaa gtaaagcgcc actgactatc tgtactctag caagaaaaaa    780
atctgtccac taaaatgaaa tcgtactgtt aaattcgagg ggagtagttt ctttatgata    840
aaatagtttc ttaggggacc atcttgctac accaaaagag tcacttcagg ttgttcatac    900
cattactcca aaaatccact tagccaatgt gttttttaac atttccctcc taaaatacaa    960
c                                                                    961
```

<210> SEQ ID NO 12
<211> LENGTH: 648
<212> TYPE: DNA
<213> ORGANISM: Hordeum vulgare
<220> FEATURE:
<221> NAME/KEY: misc_feature
<222> LOCATION: (453)..(453)
<223> OTHER INFORMATION: n is a, c, g, or t

<400> SEQUENCE: 12

```
aatcgcatga ttcttctgca tctcctgaaa ctagcatggg ttctgaggcg cctgaccctg     60
ccgttgctgc atccgtgcct ctcgtccgcc tgaaccacgt ctcctttcag tgcacgtcgg    120
tggaaaagtc cgtcgacttc taccgccgag tgcttggctt cgagctcatc aagcggccgg    180
agtccctgaa cttcaatgga gcttggctat acaagtacgg gatgggaata catctgctgc    240
agcggggcga cgacgccgac ggttgcagca tcccgacaag accgctgccg gcgatcaacc    300
cgatgggaaa ccacgtttcc ttccagtgct cagacatggc ggtcatgaag gcgaggctac    360
gagccatgga ccgggagttc gtcgtgagga aagtgtggga cggggagacg ggtggtggac    420
cagctcttct tccacgaccc cgacggcaat atngatcgag gtctgcaact gcgagaacct    480
ccccgtgata cccctcatcg ttgcatcgac gcccgggctt cctgagctgc tgccgccggc    540
gatgcagacc aatgtccatg gctagctcga gctacgttct tatgtctctc ctttgacata    600
aatacatgat taaatttcat tcgtttgaat tggttcattc gtacgtta                 648
```

<210> SEQ ID NO 13
<211> LENGTH: 700
<212> TYPE: DNA
<213> ORGANISM: Hordeum vulgare

<400> SEQUENCE: 13

```
ttttctcccg acgacggcgt ctccctctcc cccaatgcgt gaatatcacc ggaaccatac     60
atgtggtggt aacatatcag ttgaccgata acggttactt aagtgcgtac acaaaataga    120
gacatatata taaatgtagg tttttgatca ggtgcgtcga tgacgtttca cattgagctt    180
cttccctttc ttgttcattg ccgagtaatt gagcccttcc ttgtgacttt tccggagcca    240
tggagtacga tctttcttat gtaatgtagt cttgattctt cttttcacgt atgcttcatc    300
```

```
atcatcgtca tcttccctca tcgggttgcc gtattggtca tagtcttcct ctttggcgac      360

tccatccatt ccgacgatgc tccttttaga tctcctcacg acaacactgc tgggattggc      420

cgggtcggtt atgaagaagc attgtctcac atgcttagcg tgtacccatg gctcattttt      480

ggcgatgatg ttaacgttca cgggagtgct cttcgcgtcg ggtatataca tggtggtgaa      540

atacttgttt tctcttacga cgtccttggc ccatttgaat cggaacatcg tcgcatcagt      600

attggaatca cagattttgc catctgctcc ttctttgcca tctgctggct gatggcaaag      660

accctctttg ccatcagcta ccaaaaacca gacggcaaag                            700
```

<210> SEQ ID NO 14
<211> LENGTH: 615
<212> TYPE: DNA
<213> ORGANISM: Hordeum vulgare

<400> SEQUENCE: 14

```
aatggataac acacatcata tttgatcttc aagagagctg ccaatactac acttaacttg       60

caagcttttg ccattaatca acactatcta catacttaac gcacgcctag agatcatcca      120

aacttaatta acactatgcc aaactagaat agtaatcgat cagcgtgcag ttgatgtcca      180

gctcgtctca acttcaaatc acagcccata tatacaggct aaaaaccaaa gattaaaatc      240

gctggagaaa cgatttaggg gcggcctgtc ttagcagcta taccggatgc tgcatcgcgg      300

gcaatggaga caaatagagg cgacttttcc ggagggggga gatgatttct agaggtttct      360

gccgatcttg aagccctata gaggatttgg cggcggcagc agctatctcg gctattttat      420

gggagatgga gatctgattt catgctaaaa aacactcgac cacgctgcta tcggcttagc      480

cagcataaac tctaattcat gctaaaaacc actcggggac gcacatcatc aggtcatcgt      540

cccgccccag cacgtctgcc ccgctgaaac ccggctgctg ctggcaggtt cccgtcgaga      600

aggacgagct cgggc                                                       615
```

<210> SEQ ID NO 15
<211> LENGTH: 316
<212> TYPE: DNA
<213> ORGANISM: Hordeum vulgare
<220> FEATURE:
<221> NAME/KEY: misc_feature
<223> OTHER INFORMATION: Azumamugi Forward
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (283)..(283)
<223> OTHER INFORMATION: n is a, c, g, or t
<220> FEATURE:
<221> NAME/KEY: misc_feature
<222> LOCATION: (308)..(308)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t

<400> SEQUENCE: 15

```
aatnnttaac gcacgcctag agatcatcca aacttaatta acactatgcc aaactagaat       60

agtaatcgat cagcgtgcag ttgatgtcca gctcgtctca acttcaaatc acagcccata      120

tatacaggct aaaaaccaaa gattaaaatc gctggagaaa cgatttaggg gcggcctgtc      180

ttagcagcta taccggatgc tgcatcgcgg gcaatggaga caaatagagg cgacttttcc      240

ggagggggga gatgatttct agaggtttct gccgatcttg aaccctata gaggatttgg       300
```

cggcggcngc anctat 316

<210> SEQ ID NO 16
<211> LENGTH: 255
<212> TYPE: DNA
<213> ORGANISM: Hordeum vulgare
<220> FEATURE:
<221> NAME/KEY: misc_feature
<223> OTHER INFORMATION: Azumamugi Reverse
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (233)..(233)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (254)..(255)
<223> OTHER INFORMATION: n is a, c, g, or t

<400> SEQUENCE: 16
gacnnagaga cctgatgatg tgcgtccccg agtggttttt agcatgaatt agatttatgc 60
tggctaagct gatagcagcg tggtcgagtg ttttttagca tgaaatcaga tctccatcct 120
cccataaaat agccgagata ctgctgccgc cgccaaatcc tctatagggc ttcaagatcg 180
gcagaaacct ctagaaatca tctccccct ccggaaaagt cgcctctntt tgnctccctt 240
gcccagatgc ancnn 255

<210> SEQ ID NO 17
<211> LENGTH: 434
<212> TYPE: DNA
<213> ORGANISM: Hordeum vulgare
<220> FEATURE:
<221> NAME/KEY: misc_feature
<223> OTHER INFORMATION: Kanto Nakate Gold Forward

<400> SEQUENCE: 17
tccttacttg cagcttttgc cattaatcaa cccttatcta catacttaac gcacgcctag 60
agatcatcca aacttaatta acactatgcc aaactagaat agtaatcgat cagcgtgcag 120
ttgatgtcca gctcgtctca acttcaaatc acagcccata tatacaggct aaaaaccaaa 180
gattaaaatc gctggagaaa cgatttaggg gcggcctgtc ttagcagcta taccggatgc 240
tgcatcgcgg gcaatggaga caaatagagg cgacttttcc ggaggggga gatgatttct 300 agaggtttct gccgatcttg aagccctata gaggatttgg cggcggcagc agctatctcg 360
gctattttat gggagatgga gatctgattt catgctaaaa aacactcgac cacgctgcta 420
tgcgcttagc cagc 434

<210> SEQ ID NO 18
<211> LENGTH: 401
<212> TYPE: DNA
<213> ORGANISM: Hordeum vulgare
<220> FEATURE:
<221> NAME/KEY: misc_feature
<223> OTHER INFORMATION: Kanto Nakate Gold Reverse
<220> FEATURE:

<221> NAME/KEY: misc_feature
<222> LOCATION: (7)..(7)
<223> OTHER INFORMATION: n is a, c, g, or t

<400> SEQUENCE: 18
ccggcgngaa cgatgacctg atgatgtgcg tccccgagtg gtttttagca tgaattagat 60
ttatgctggc taagccgata gcagcgtggt cgagtgtttt ttagcatgaa atcagatctc 120
catcctccca taaaatagcc gagatactgc tgccgccgcc aaatcctcta tagggcttca 180
agatcggcag aaacctctag aaatcatctc ccccctccgg aaaagtcgcc tctatttgtc 240
tcctctattt gtctcccatt gcccgcgatg cagcatccgg tatagctgct aagacaggcc 300
gcccctaaat cgtttctcca gcgattttaa tctttggttt ttagcctgta tatatgggct 360
gtgatttgaa gttgagacga gctggacatc aactgcacgc t 401

<210> SEQ ID NO 19
<211> LENGTH: 650
<212> TYPE: DNA
<213> ORGANISM: Hordeum vulgare

<400> SEQUENCE: 19
aaacaattca ccaccatacc agccagtact tttttgtgat tccctagcca ctatttattt 60
atatttgata ggacaaaata attatagtgc tcagtagcat gtgaagaacc cattgcatgt 120
atgggtctgg tatggaaata ttgatgcatg ggtgcaaccg ctcaataacc cacagttcgc 180
actagcaaac caacgtgtgc ttgtatggtt agatgggcag tagtatcccc atcccactag 240
cgttcaagcc ctggtgcttg caatattcct gggtttattt caggatttac gatgatatgc 300
tttcagtggg aggagacatt cccatcgatg atgagacgcc tacggtgact ttgtaaatct 360
caagatgaaa tgtcagctca atctttcgga tgtgctcaca gggatggggt atacgtgtgt 420
gcgttcatag gggtgactgt atgcgcctgt atatgagcgc atgcgtctac tatgttaaag 480
aatcacggtt ccatcgctac tagatgctac ctaacgaaaa aatgagtgtc gcaaattcat 540
aataaatcaa tgactctagt aggtttgtca tcgaaattac cacgcaatca tagaatttgt 600
tagcttggtg gggctcaacg gccaaggtga ctgagtgacg ttaatcgtca 650

<210> SEQ ID NO 20
<211> LENGTH: 569
<212> TYPE: DNA
<213> ORGANISM: Hordeum vulgare
<220> FEATURE:
<221> NAME/KEY: misc_feature
<223> OTHER INFORMATION: Azumamugi Forward
<220> FEATURE:
<221> NAME/KEY: misc_feature
<222> LOCATION: (561)..(561)
<223> OTHER INFORMATION: n is a, c, g, or t

<400> SEQUENCE: 20
aaaataatta tagtgctcag tagcatgtga agaacccatt gcatgtatgg gtctggtatg 60
gaaatattga tgcatgggtg caaccgctca ataacccaca gttcgcacta gcaaaccaac 120
gtgtgcttgt atggttagat gggcagtagt atccccatcc cactagcgtt caagccctgg 180
tgcttgcaat attcctgggt ttatttcagg atttacgatg atatgctttc agtgggagga 240
gacattccca tcgatgatga gacgcctacg gtgactttgt aaatctcaag atgaaatgtc 300
agctcaatct ttcggatgtg ctcacaggga tggggtatac gtgtgtgcgt tcataggggt 360
gactgtatgc gcctgtatat gagcgcatgc gtctactatg ttaaagaatc acggttccat 420
cgctactaga tgctacctaa cgaaaaaatg agtgtcgcaa attcataata aatcaatgac 480
tctagtaggt ttgtcatcga aattaccacg caatcataga atttgttagc ttggtggggc 540
tcaacggcca aggtgactga ntgacgtta 569

<210> SEQ ID NO 21
<211> LENGTH: 602
<212> TYPE: DNA
<213> ORGANISM: Hordeum vulgare
<220> FEATURE:
<221> NAME/KEY: misc_feature
<223> OTHER INFORMATION: Azumamugi Reverse
<220> FEATURE:
<221> NAME/KEY: misc_feature
<222> LOCATION: (15)..(15)
<223> OTHER INFORMATION: n is a, c, g, or t

<400> SEQUENCE: 21
tacaattcta ttgantgcgt ggtaatttcg atgacaaacc tactagagtc attgatttat 60
tatgaatttg cgacactcat tttttcgtta ggtagcatct agtagcgatg gaaccgtgat 120
tctttaacat agtagacgca tgcgctcata tacaggcgca tacagtcacc cctatgaacg 180
cacacacgta taccccatcc ctgtgagcac atccgaaaga ttgagctgac atttcatctt 240
gagatttaca aagtcaccgt aggcgtctca tcatcgatgg gaatgtctcc tcccactgaa 300
agcatatcat cgtaaatcct gaaataaacc caggaatatt gcaagcacca gggcttgaac 360
gctagtggga tggggatact actgcccatc taaccataca agcacacgtt ggtttgctag 420
tgcgaactgt gggttattga gcggttgcac ccatgcatca atatttccat accagaccca 480
tacatgcaat gggttcttca catgctactg agcactataa ttattttgtc ctatcaaata 540
taaataaata gtggctaggg aatcacaaaa aagtactggc tggtatggtg gtgaattgtt 600
aa 602

<210> SEQ ID NO 22
<211> LENGTH: 570
<212> TYPE: DNA
<213> ORGANISM: Hordeum vulgare
<220> FEATURE:
<221> NAME/KEY: misc_feature
<223> OTHER INFORMATION: Kanto Nakate Gold Forward

<400> SEQUENCE: 22
aaaataatta tagtgctcag tagcatgtga agaacccatt gcatgtatgg gtctggtatg 60
gaaatattga tgcatgggtg caaccgctca ataacccaca gttcgcacta gcaaaccaac 120
gtgtgcttgt atggttagat gggcagtagt atccccatcc cactagcatt caagccctgg 180
tgcttgcaat attcctgggt ttatttcagg atttacgatg atatgctttc agtgggagga 240
gacattccca tcgatgatga gacgcctacg gtgactttgt aaatctcaag atgaaatgtc 300
agctcaatct ttcggatgtg ctcacaggga tggggtatac gtgtgtgcgt tcataggggt 360
gactgtatgc gcctgtatat gagcgcatgc gtctactatg ttaaagaatc acggttccat 420
cgctactaga tgctacctaa cgaaaaaatg agtgtcgcaa attcataata aatcaatgac 480
tctagtaggt ttgtcatcga aattaccacg caatcataga atttgttagc ttggtggggc 540
tcaacggcca aggtgactga gtgacgttaa 570

<210> SEQ ID NO 23
<211> LENGTH: 601
<212> TYPE: DNA
<213> ORGANISM: Hordeum vulgare
<220> FEATURE:
<221> NAME/KEY: misc_feature
<223> OTHER INFORMATION: Kanto Nakate Gold Reverse
<220> FEATURE:
<221> NAME/KEY: misc_feature
<222> LOCATION: (13)..(14)
<223> OTHER INFORMATION: n is a, c, g, or t

<400> SEQUENCE: 23

```
ctacaattct atnntgcgtg gtaatttcga tgacaaacct actagagtca ttgatttatt        60
atgaatttgc gacactcatt ttttcgttag gtagcatcta gtagcgatgg aaccgtgatt       120
ctttaacata gtagacgcat gcgctcatat acaggcgcat acagtcaccc ctatgaacgc       180
acacacgtat accccatccc tgtgagcaca tccgaaagat tgagctgaca tttcatcttg       240
agatttacaa agtcaccgta ggcgtctcat catcgatggg aacgtctcct cccactgaaa       300
gcatatcatc gtaaatcctg aaataaaccc aggaatattg caagcaccag ggcttgaacg       360
ctagtgggat ggggatacta ctgcccatct aaccatacaa gcacacgttg gtttgctagt       420
gcgaactgtg ggttattgag cggttgcacc catgcatcaa tatttccata ccagacccat       480
acatgcaatg ggttcttcac atgctactga gcactataat tattttgtcc tatcaaatat       540
aaataaatag tggctaggga atcacaaaaa agtactggct ggtatggtgg tgaattgtta       600
a                                                                      601
```

<210> SEQ ID NO 24
<211> LENGTH: 1297
<212> TYPE: DNA
<213> ORGANISM: Hordeum vulgare

<400> SEQUENCE: 24

```
catttgaggg gtcgaatttg cctactccgg ctgtgctcta accgcttcgg acagtcgcct        60
ccggcccaaa gccccgaacc cccgcgatgc catccctctc ctcccccttc gccgccggcg       120
actgctccgc cgataagttc gaccccgact acctctactt tctccgccac cttcgcaccg       180
agggcagctc ctatgtcctc gagctcccgc ccggcggtgc ctcccctgtc cccgtcatca       240
ggtacgagtc ccccatctcc atctccgacg gcgaatgtgt ctcggaccct tccccgggcg       300
gcgcaagcac caaccgccga gcggaagaga gggactcgtc cgtggaggcg cccccctcgt       360
ggatcgactc catcgtcgac atggacgagg attaccgcct tttcctgcac cacacgcgcg       420
tggtgaataa ccgcctgaag ctccagatgg ggggcgtcgt tgtggactat gagccggacc       480
cggacgccgc gcaatctgga ggtagcagcg gggtcgagga gcaatcggag aaagaggcgc       540
ccgttgcttc ctcgggggga gaggagcagg cggtcgactc agatgagccg gttgtaatta       600
tgccggagcc gaacgcctac gactggcgtg cggatccagc ccctcgtaaa aggatgcagg       660
gccaggaaga tattgggcac aaggatgctc agcctcgcac tgcttcgtca catagatcag       720
gtgttatatg gcctccacat atcaaccata ggccagattc agacttcaag cgaagattga       780
tggatgctct tcagaaacca tttagccgga aagaatatat taagctgttt gacatggctt       840
ctattcgtac tcccttagtg aagttgcgac aggtgcgcaa tgatgcaaaa ttctacccta       900
ccgaggagat gggcaattca tattttgatc attacccaga tcttgtcgaa caagttacaa       960
acaatacctt ttccaagggt ttagctttga tgcgtggatt tttcttctgg ttgcagaata      1020
gtgcacacga ggaccaattc agaccatgga cagatgatct gaaagatcaa gatgttattc      1080
cgttgatgga cttagattac gcatttcctt agttcattca ctcatcttct cttttgtgga      1140
aataattccc taagggtgaa accattctca gtacagaata tttgattttt atcattttat      1200
atattgagtg tgcgaataag tactggagca gtcaacttgt gttgctcttt ctcttgggag      1260
```

aataaatgta tatattgcat aaaaaaaaaa aaaaaaa 1297

<210> SEQ ID NO 25
<211> LENGTH: 668
<212> TYPE: DNA
<213> ORGANISM: Hordeum vulgare

<400> SEQUENCE: 25
tatgaactca ccggtgagca attcaacgtt tcaaacaaca acacagagct cgcttagggc 60
gccagtttgg tgttctgaaa tgtcagatgt acatcatcct cgcaaaaact ggctcacggg 120
gcgaaaattc aatctataca catgaatact gtggaagtct gaaagcacac tgttcaacta 180
ttaaaatcaa acacctataa cctatgttcc tcctcaaaac ccctagaaaa tatgcgggac 240
tttgctcgcc agaacacgct cgcgcctttc gacgtaagca tgtgggaacc atcctgcttt 300
tcccttgcat tcaccttcgg cccagccgtt gcttgatatc tttcggacga taacgatgtc 360
accaactgat aagtttagct caaactcact ctcagccttg aaggaatcga gggcctctcc 420
caggaacaaa tcgacagagt tgactgcctg atcagcaaaa gtggaggcaa acatgccatt 480
aacttcgtca tatgatggtg gtggcggtga cgtataactt tctgctgcag gggtggagg 540 cgcttcaatt ttttggcgct cagataccat ttcttcttcc aaatggtcaa ggatctccag 600
gactttctga tgataagttc tctcggcctc aaccattgct atgaggcgtt gtaatgttaa 660
tctttgct 668

<210> SEQ ID NO 26
<211> LENGTH: 1362
<212> TYPE: DNA
<213> ORGANISM: Hordeum vulgare

<400> SEQUENCE: 26
cgtgcacagg tctgtctttg gagccgctga tcggggccat agcggcgggg aacgccgtgg 60
cgctgaagcc gtcggagctg gcgccggcga cggccaggtt cctggaggag aacataggcg 120
agtacctgga cgccacggcg gtgaaggtca tccagggcgg ccccgcggtg ggcgagcagc 180
tcatggagca cagatgggac aaggtcctct tcaccgggtg cccgcgcgtg gcgcgcgtgg 240
tgatggcggc ggcggcgaag cacctgacgc cggtggcgct ggagctgggc gggaagtgcc 300
cctgcatctt cgacgccgtt gccggcagga ggaacctcca gtcctcggtg aaccgcgtga 360
tcttcgccaa gtggtcgtcc tgcgccggcc aggcctgcat cgccatcgac tacgtgctcg 420
tcgaggagcg attcgcgccc accctgatca agttgctcaa gtcgacgctc aagaggttca 480
tcgccgactc ggaccagatg gcgcggatcg tcaacgcgcg gcatttccag cggctgagta 540
acctcctcaa ggacccggcg gtggcggcat ccatcctgca cggcggcaac ttagacgcca 600
agaacctgtc catcgatccc acgatactgc tgaacccgcc gctggactcg gcgatcatga 660
ccgaggagat cttcggccct ctgctcccca tcatcacggt gaagaagatc gaggacagca 720
tcgcgttcgt gagggcgcgg ccgaagccgc tggcggtgta cgccttcacc gacagcgcgc 780
cgctgaagcg ccggatcgta gaggagacgt cgtcggggag cgtcaccttc aacgacgccg 840
tcgtgcaatt cgggatcgac tcgctgccgt tcggcggcgt ggggcagagc gggttcgggc 900
agtaccacgg caagtactcc ttcgagatgt tcagccacaa gaaggcggtg ctgcggcggg 960
ggttcctggt ggaggccatg ctgaggtacc cgccctggga cgagcagaag atcgccatga 1020
tgcgccacct ctaccgctac gactacgtcc gcttcatctt caccttcctc ggcctgtgga 1080
aatgatggcg cggctggatg ggtttgcccc caggaaatta attaattatt atttatttgg 1140

-continued

```
tgaatgagtg gatgaacagg tacatgaata agcataccac gttagtttgt aaggggtgtg   1200

tagcgggctt gcactcggta cttgctagtg tgccaataat acaagaatgt tctgttttca   1260

tcctgtctac tccaaggtac tatagtctta agaggtgtgg ttagacctca ctcgactgat   1320

caagtcacat aatatagaaa aaggaaagga aaaaaacagc gg                      1362
```

<210> SEQ ID NO 27
<211> LENGTH: 555
<212> TYPE: DNA
<213> ORGANISM: Hordeum vulgare

<400> SEQUENCE: 27

```
gtttttttcc tttcettttt ctatattatg tgacttgatc cagtcgagtg aggtctaacc     60

acacctctta agactatagt accttggagt agacaggatg aaaacagaac attcttgtat    120

tattggcaca ctagcaagta ccgagtgcaa gcccgctaca caccccttac aaactaacgt    180

ggtatgctta ttcatgtacc tgttcatcca ctcattcacc aaataaataa taattaatta    240

atttcctggg ggcaaaccca tccagccgcg ccaccatttc cacaggccga ggaaggtgaa    300

gatgaagcgg acgtagtcgt agcggtagag gtggcgcatc atggcgatct tctgctcgtc    360

ccagggcggg tacctcagca tggcctccac caggaacccc cgccgcagca ccgccttctt    420

gtggctgaac atctcgaagg agtacttgcc gtggtactgc ccgaacccgc tctgccccac    480

gccgccgaac ggcagcgagt cgatcccgaa ttgcacgacg gcgtcgttga aggtgacgct    540

ccccgacgac gtctc                                                     555
```

<210> SEQ ID NO 28
<211> LENGTH: 311
<212> TYPE: DNA
<213> ORGANISM: Hordeum vulgare

<400> SEQUENCE: 28

```
acaactgaac taccactacc attgccatac cactggtgct acaatatact agtatatgtg     60

ccatgacatc acaaaaattt ctacctaatc ccaaggctta aactaatctg agtactcaca    120

ctgcggagac attcgttctt ctacctgccc taacttactg taatcactat tcacaaatca    180

caatcaacag caccagccat gagccaggca ggctagaaca tgatcctgcg gtccaatctg    240

gatccgacgg ccgagatcaa cgcggtggtc ttctcctgga gcacgtgcac cacgtccgcc    300

agcggccgcc a                                                         311
```

<210> SEQ ID NO 29
<211> LENGTH: 1377
<212> TYPE: DNA
<213> ORGANISM: Hordeum vulgare

<400> SEQUENCE: 29

```
gggagagcgg agggggcgcg tcgtcgtcac ggtggcccaa gacggaggtg cacgcgctta     60

tccagctgcg catggacatg gacaatcgct accaggagaa cggacccaag ggcccgctgt    120

gggaggagat ctccgccggg atgcggcggc tgggctacag ccgcaactcc aaacgatgca    180

aggagaagtg ggagaacatc aacaagtact tcaagaaggt gaaggagagc aacaagaggc    240

ggccggagga ctccaagaca tgcccgtact tccaccagct cgaggccatc taccgcaaga    300

aacacaacgg cggcggcggc agcggcgcgg ccgccaacaa cgccgccgta tctgtctcag    360

tccctgccgt cgcggagcat cagaacctga accggcacga gatcgagatc gagatcgagg    420

ggaagaagat caacgacaac gacaagagga acaacggagg agtcggagcc gcgcaggtgc    480
```

-continued

```
cgacaagcaa cgggcagaca acgccgacga cggccacgtt cgacgtcgat ctgggcgtaa    540

aaaagccaga agacactgtg agggagctga acgagcagcc gcaacgggag ttgacgacgg    600

acgagaccga cagcgacgac atgggcgatg actacactga cgacggcgag gacggcgagg    660

acgacggcaa aatgcagtac aggatacagt tccagaggcc aaacccggtc ggcgccaaca    720

atgcacctcc accggcaacc accgcgacga cagcagcgcc gacatcgact ccgtcgagct    780

ccttcctcgc catggttcaa taaaggctca gcaccattgc tcatccatca gtatacttcc    840

agttccagag aagctataac ctcgaaacat caccatcacc gagtcaccgc tcgaacatgc    900

atcacctcct cgagtcgatc atcgccatca catcacacca tcaccgacga cggcgactgt    960

tctttttcac cttgtaattc ctctcgtgcc attccattat ttattgattc gttctgtgta   1020

ataagagagc ctctcttctg tcccccaaac cggccaagga ggcagagggg gtggccggta   1080

gagcaagcaa gtccctgcgt aacataggtg ttcatcctcg tgttaaggcc aaagaattgt   1140

acatcgatgt aagagtcccc tgatgtctgt ttttttctct tcttcttttt tcggcggtat   1200

acaggtttgt atacgggtat acaagagtta catacatttc aagcaacttg gatcagaggt   1260

ccaaagattg ttttagctgg tgtcgccccc ttgtttagcg gtgattagta taagtgtttt   1320

ttcttgataa atttcgaaat aagtgacttt atattttact aaaaaaaaaa aaaaaaa      1377


<210> SEQ ID NO 30
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 30

ctgcccccaa tccatcgacc t                                                21


<210> SEQ ID NO 31
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 31

agcggttgga gaagaggacg t                                                21


<210> SEQ ID NO 32
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 32

tatggactgg atggagcaag a                                                21


<210> SEQ ID NO 33
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 33

tagagaagtg gaatgatgga t                                                21


<210> SEQ ID NO 34
```

<211> LENGTH: 21
<212> TYPE: DNA
<213> ORGANISM: Artificial
<220> FEATURE:
<223> OTHER INFORMATION: An artificially synthesized primer sequence

<400> SEQUENCE: 34
tcagatataa gccggtcatt c 21

<210> SEQ ID NO 35
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 35
acaagagcgt ataaacagcg g 21

<210> SEQ ID NO 36
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 36
tttggaaaca gacgaacaca c 21

<210> SEQ ID NO 37
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 37
gcttcccttg ttgcccgatt g 21

<210> SEQ ID NO 38
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 38
gaaacccgtc cagctctaga g 21

<210> SEQ ID NO 39
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 39
atgccaaagg tcaatgatct c 21

<210> SEQ ID NO 40
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 40
ccgaagctac atggaacaat c 21

<210> SEQ ID NO 41
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 41
ggggactgct gactgaataa c 21

<210> SEQ ID NO 42
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 42
ggcacgagga gagagcattt g 21

<210> SEQ ID NO 43
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 43
gaaggctgta atatgcgtgt g 21

<210> SEQ ID NO 44
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 44
catcatccca aagtctaagt g 21

<210> SEQ ID NO 45
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 45
tagggtattt cgttctgact g 21

<210> SEQ ID NO 46
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 46
gtccgcctga accacgtctc c 21

<210> SEQ ID NO 47
<211> LENGTH: 21
<212> TYPE: DNA
<213> ORGANISM: Artificial
<220> FEATURE:

<223> OTHER INFORMATION: An artificially synthesized primer sequence

<400> SEQUENCE: 47
gtcggggtcg tggaagaaga g 21

<210> SEQ ID NO 48
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 48
ctcccccaat gcgtgaatat c 21

<210> SEQ ID NO 49
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 49
ctgtgattcc aatactgatg c 21

<210> SEQ ID NO 50
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 50
cttcaagaga gctgccaata c 21

<210> SEQ ID NO 51
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 51
tctcgacggg aacctgccag c 21

<210> SEQ ID NO 52
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 52
aacaattcac caccatacca g 21

<210> SEQ ID NO 53
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 53
aacgtcactc agtcaccttg g 21

<210> SEQ ID NO 54

<211> LENGTH: 21
<212> TYPE: DNA
<213> ORGANISM: Artificial
<220> FEATURE:
<223> OTHER INFORMATION: An artificially synthesized primer sequence

<400> SEQUENCE: 54
cccgactacc tctactttct c 21

<210> SEQ ID NO 55
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 55
catggtctga attggtcctc g 21

<210> SEQ ID NO 56
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 56
catcatcctc gcaaaaactg g 21

<210> SEQ ID NO 57
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 57
gccgagagaa cttatcatca g 21

<210> SEQ ID NO 58
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 58
gatcaagttg ctcaagtcga c 21

<210> SEQ ID NO 59
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 59
gctacacacc ccttacaaac t 21

<210> SEQ ID NO 60
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 60

-continued cttggagtag acaggatgaa a 21

<210> SEQ ID NO 61
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 61
gggatcgact cgctgccgtt c 21

<210> SEQ ID NO 62
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 62
atgacatcac aaaaatttct a 21

<210> SEQ ID NO 63
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 63
gaccgcagga tcatgttcta g 21

<210> SEQ ID NO 64
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 64
caatcgctac caggagaacg 20

<210> SEQ ID NO 65
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 65
atcaggggac tcttacatcg 20

<210> SEQ ID NO 66
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 66
gaaagatgat tgccaactac c 21

<210> SEQ ID NO 67
<211> LENGTH: 21
<212> TYPE: DNA
<213> ORGANISM: Artificial
<220> FEATURE:

<223> OTHER INFORMATION: An artificially synthesized primer sequence

<400> SEQUENCE: 67
gtcataactc ggcaaacata g 21

<210> SEQ ID NO 68
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 68
gaaagatgat tgccaactac c 21

<210> SEQ ID NO 69
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 69
atagggcttc aagatcggca g 21

<210> SEQ ID NO 70
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 70
atagaggcga cttttccgga g 21

<210> SEQ ID NO 71
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 71
acaagaacaa gacgctcgag g 21

<210> SEQ ID NO 72
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 72
ccagtgtgag tgtatgcgag c 21

<210> SEQ ID NO 73
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 73
tcacgatccc ttctttccct c 21

<210> SEQ ID NO 74

-continued

```
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 74

ccggtgaaac tgaagctact g                                         21


<210> SEQ ID NO 75
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 75

tccgaatgaa atgaactctg c                                         21


<210> SEQ ID NO 76
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 76

ccacattagc attgacctga g                                         21


<210> SEQ ID NO 77
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 77

gtcataactc ggcaaacata g                                         21
```

BARLEY ROW TYPE GENE AND USE THEREOF

TECHNICAL FIELD

The present invention relates to the barley row-type gene Vrs1 and mutants thereof, and methods for altering the row type and panicle morphology of barley using these genes.

BACKGROUND ART

Rice, wheat, barley, corn, and such, which are important cereals worldwide, are crops whose seeds (embryo and endosperm) are used as food. Of such crops, barley has two-rowed and six-rowed varieties (FIG. 1). Barley forms three one-flowered spikelets per rachis; and barley varieties that have all three spikelets produce seeds are collectively called six-rowed barley, while varieties in which only the central spikelets produce seeds are generally called two-rowed barley. The difference between six-row and two-row types (hereinafter referred to as "row type") directly influences the yield, because it has a great impact on determining the number, shape, and size of grains. The row type is also an important phenotype that affects the modes of use for barley, such as malt production, brewing, pearling, and feed. Furthermore, genetic studies have revealed that the row type is closely related to resistance to *Fusarium* head blight.

It has been revealed that the six-row type is a phenotype governed by a single recessive gene, vrs1, while Vrs1, the dominant gene for two-rowed barley, suppresses the development of lateral spikelets (FIG. 1). However, their gene products remain unknown. Furthermore, although the genomic structure (specifically, arrangement of homologous genes) is highly conserved among different cereal species, no genes homologous to the row-type gene are known. Even if such genes exist, their functions are unknown.

Prior art documents related to the present invention include:

Non-patent Document 1: Congfen He, et al. Genome 47:1122-1129 (2004)

Non-patent Document 2: Komatsuda T. and Tanno K. Comparative high resolution map of the six-rowed spike locus 1 (vrs1) in several populations of barley. *Hordeum vulgare* L. Hereditas 141:68-73 (2004)

Patent Document 1: Japanese Patent Application Kokai Publication No. (JP-A) 2004-313062 (unexamined, published Japanese patent application)

DISCLOSURE OF THE INVENTION

Problems to be Solved by the Invention

The present invention was accomplished under the above circumstances. An objective of the present invention is to isolate and identify barley row-type genes and to provide methods for altering the row type and panicle morphology of barley using these genes.

Means for Solving the Problem

The present invention provides genes involved in determining barley's row type. It is known that the six-row type is a phenotype that is governed by a single recessive gene, vrs1, while Vrs1, the dominant gene for two-rowed barley, suppresses the development of lateral spikelets. However, their gene products have not been elucidated. The present inventors have endeavored to elucidate the region it exists in and to isolate it as a single gene.

The present inventors first created a linkage map for the row-type gene vrs1. Then, the present inventors prepared a BAC alignment covering the row-type gene region by screening a BAC library using PCR markers linked to the target gene and by performing chromosome walking using PCR markers. As a result, the present inventors discovered that it is highly probable that the vrs1 row-type gene is linked to markers within the region of AFLP1 to MO53F18-T7.

Then, using mutants of the two-rowed varieties, the present inventors examined deletions in candidate regions for the gene governing the row type. The nucleotide sequence of a candidate region for the gene governing the row type was compared between the original varieties and the mutants. As a result, many nucleotide substitutions that result in a non-synonymous amino acid substitution or stop codon formation were found in the mutants, while no mutations were found in the nucleotide sequences of the original varieties. This finding demonstrates that the candidate region corresponds to the gene of interest. Thus, the present invention relates to genes involved in determining the row type of barley. Specifically, the present invention provides the following inventions:

[1] a DNA of any one of (a) to (e) below:

(a) a DNA encoding a protein comprising the amino acid sequence of SEQ ID NO: 3;

(b) a DNA comprising the coding region of the nucleotide sequence of SEQ ID NO: 1 or 2;

(c) a DNA encoding a protein comprising an amino acid sequence with an artificial substitution, deletion, addition and/or insertion of one or more amino acids in the amino acid sequence of SEQ ID NO: 3;

(d) a barley-derived DNA that hybridizes under stringent conditions to a DNA comprising the nucleotide sequence of SEQ ID NO: 1 or 2; and (e) a barley-derived DNA that hybridizes under stringent conditions to a DNA comprising the nucleotide sequence of SEQ ID NO: 1 or 2, and which encodes a protein functionally equivalent to a protein comprising the amino acid sequence of SEQ ID NO: 3;

[2] a DNA of any one of (a) to (d) below:

(a) a DNA that expresses an RNA complementary to a transcript of the DNA of [1];

(b) a DNA that expresses an RNA having ribozyme activity of specifically cleaving a transcript of the DNA of [1];

(c) a DNA that expresses an RNA that inhibits expression of the DNA of [1] by a co-suppression effect; and (d) a DNA that expresses an RNA having RNAi activity of specifically cleaving a transcript of the DNA of [1];

[3] a vector comprising the DNA of [1] or [2];

[4] a transformed cell harboring the DNA of [1] or [2] in an expressible manner;

[5] a transformed barley cell into which the DNA of [1] or [2] has been introduced;

[6] a transformed barley plant comprising the transformed barley cell of [5];

[7] a transformed barley plant which is a progeny or clone of the transformed barley plant of [6];

[8] a breeding material of the transformed barley plant of [6] or [7];

[9] a method for producing the transformed barley plant of [6] or [7], which comprises the step of introducing the DNA of [1] or [2] into a barley cell and then regenerating a barley plant from the barley cell;

[10] a method for altering the row type or panicle morphology of a barley plant, which comprises the step of expressing the DNA of any one of (a), (b), and (e) of [1] in a cell of a barley plant that is not two-rowed;

[11] a method for altering the row type or panicle morphology of a barley plant, which comprises the step of expressing the DNA of (c) or (d) of [1] in a two-rowed barley plant cell;

[12] a method for altering the row type or panicle morphology of a barley plant, which comprises the step of expressing the DNA of [2] in a two-rowed barley plant cell;

[13] a method for conferring a barley plant with resistance to *Fusarium* head blight, which comprises the step of expressing the DNA of [1] or [2] in a barley cell;

[14] an agent for enhancing resistance of a barley plant to *Fusarium* head blight, which comprises any one of the DNAs of [1] and [2], and the vector of [3];

[15] a DNA comprising a partial sequence of the DNA of [1];

[16] a DNA comprising the nucleotide sequence of any one of SEQ ID NOs: 4 to 29;

[17] a primer set for amplifying the whole or a portion of the DNA of [1];

[18] a primer set of at least any one of (a) to (r) below:

(a) a DNA comprising the nucleotide sequence of SEQ ID NO: 30 and a DNA comprising the nucleotide sequence of SEQ ID NO: 31;

(b) a DNA comprising the nucleotide sequence of SEQ ID NO: 32 and a DNA comprising the nucleotide sequence of SEQ ID NO: 33;

(c) a DNA comprising the nucleotide sequence of SEQ ID NO: 34 and a DNA comprising the nucleotide sequence of SEQ ID NO: 35;

(d) a DNA comprising the nucleotide sequence of SEQ ID NO: 36 and a DNA comprising the nucleotide sequence of SEQ ID NO: 37;

(e) a DNA comprising the nucleotide sequence of SEQ ID NO: 38 and a DNA comprising the nucleotide sequence of SEQ ID NO: 39;

(f) a DNA comprising the nucleotide sequence of SEQ ID NO: 40 and a DNA comprising the nucleotide sequence of SEQ ID NO: 41;

(g) a DNA comprising the nucleotide sequence of SEQ ID NO: 42 and a DNA comprising the nucleotide sequence of SEQ ID NO: 43;

(h) a DNA comprising the nucleotide sequence of SEQ ID NO: 44 and a DNA comprising the nucleotide sequence of SEQ ID NO: 45;

(i) a DNA comprising the nucleotide sequence of SEQ ID NO: 46 and a DNA comprising the nucleotide sequence of SEQ ID NO: 47;

(j) a DNA comprising the nucleotide sequence of SEQ ID NO: 48 and a DNA comprising the nucleotide sequence of SEQ ID NO: 49;

(k) a DNA comprising the nucleotide sequence of SEQ ID NO: 50 and a DNA comprising the nucleotide sequence of SEQ ID NO: 51;

(l) a DNA comprising the nucleotide sequence of SEQ ID NO: 52 and a DNA comprising the nucleotide sequence of SEQ ID NO: 53;

(m) a DNA comprising the nucleotide sequence of SEQ ID NO: 54 and a DNA comprising the nucleotide sequence of SEQ ID NO: 55;

(n) a DNA comprising the nucleotide sequence of SEQ ID NO: 56 and a DNA comprising the nucleotide sequence of SEQ ID NO: 57;

(o) a DNA comprising the nucleotide sequence of SEQ ID NO: 58 and a DNA comprising the nucleotide sequence of SEQ ID NO: 59;

(p) a DNA comprising the nucleotide sequence of SEQ ID NO: 60 and a DNA comprising the nucleotide sequence of SEQ ID NO: 61;

(q) a DNA comprising the nucleotide sequence of SEQ ID NO: 62 and a DNA comprising the nucleotide sequence of SEQ ID NO: 63; and (r) a DNA comprising the nucleotide sequence of SEQ ID NO: 64 and a DNA comprising the nucleotide sequence of SEQ ID NO: 65;

[19] a DNA comprising at least consecutive 15 nucleotides complementary to the DNA of [1] or a complementary sequence thereof;

[20] a method comprising the steps of:

(a) preparing a DNA sample from a barley plant;

(b) amplifying the DNA region of [1] from the DNA sample; and (c) comparing the molecular weight or nucleotide sequence of the amplified DNA fragment with that of the DNA of any one of (a), (b), and (e) of [1];

which is a method for determining a barley plant is two-rowed when the molecular weight or nucleotide sequence is consistent with that of the DNA of any one of (a), (b), and (e) of [1];

[21] a method comprising the steps of:

(a) preparing a DNA sample from a barley plant;

(b) amplifying the DNA region of [1] from the DNA sample;

(c) fractionating the amplified double-stranded DNA on a non-denaturing gel; and (d) comparing the mobility of the fractionated double-stranded DNA on the gel with that of the DNA of any one of (a), (b), and (e) of [1];

which is a method for determining a barley plant is two-rowed when the gel mobility of its DNA is consistent with that of the DNA of any one of (a), (b), and (e) of [1];

[22] a method comprising the steps of:

(a) preparing a DNA sample from a barley plant;

(b) amplifying the DNA region of [1] from the DNA sample;

(c) dissociating the amplified DNA into single-stranded DNAs;

(d) fractionating the dissociated single-stranded DNAs on a non-denaturing gel; and (e) comparing the mobility of the fractionated single-stranded DNA on the gel with that of the DNA of any one of (a), (b), and (e) of [1];

which is a method for determining a barley plant is two-rowed when the gel mobility of its DNA is consistent with that of the DNA of any one of (a), (b), and (e) of [1];

[23] a method comprising the steps of:

(a) preparing a DNA sample from a barley plant;

(b) amplifying the DNA region of [1] from the DNA sample;

(c) fractionating the amplified DNA on a gel with a gradually increasing concentration of a DNA denaturant; and (d) comparing the mobility of the fractionated DNA on the gel with that of the DNA of any one of (a), (b), and (e) of [1];

which is a method for determining a barley plant is two-rowed when the gel mobility of its DNA is consistent with that of the DNA of any one of (a), (b), and (e) of [1];

[24] a method for selecting a two-rowed barley plant, which comprises the steps of:

(a) producing a barley plant by crossing a two-rowed barley plant with a barley plant that is not two-rowed or whose row type is unknown; and (b) judging whether the barley plant produced in step (a) is two-rowed by the method of any one of [20] to [23];

[25] a method of screening for a test compound, which comprises the steps of:

(a) contacting a test compound with a transcript of the DNA of [1];

(b) detecting the binding between a test compound and the transcript of the DNA of [1]; and (c) selecting a test compound that binds to the transcript of the DNA of [1];

[26] a method of screening for a test compound, which comprises the steps of:

(a) contacting a test compound with a cell collected from a barley plant;

(b) determining the expression level of a transcript of the DNA of [1]; and (c) selecting a test compound that alters the expression level of the transcript as compared to when the test compound is not contacted;

[27] a method of screening for a test compound, which comprises the steps of:

(a) providing a cell or cell extract comprising a DNA in which a reporter gene is operably linked downstream of a promoter region of the DNA of [1];

(b) contacting a test compound with the cell or cell extract;

(c) determining the expression level of the reporter gene in the cell or cell extract; and (d) selecting a test compound that alters the expression level of the reporter gene as compared to when the test compound is not contacted;

[28] a method comprising the steps of:

(a) contacting the protein encoded by the DNA of [1] with a DNA comprising the reporter gene operably linked to the genomic fragment in a cell or cell extract; and (b) determining whether the reporter gene is expressed; which is a method for determining whether a test genomic fragment comprises a target sequence in a protein encoded by the DNA of [1], wherein the test genomic fragment is determined to comprise a target sequence in a protein encoded by the DNA of [1] when the protein encoded by the DNA of [1] allows expression of a reporter gene operably linked to the test genomic fragment;

[29] a method comprising the steps of:

(a) contacting the protein encoded by the DNA of [1] with a DNA comprising the test genomic fragment in a cell or cell extract; and (b) determining whether a gene is expressed from the test genomic fragment;

which is a method for determining whether a test genomic fragment comprises a gene whose expression is regulated by a protein encoded by the DNA of [1], wherein the test genomic fragment is determined to comprise a gene whose expression is regulated by a protein encoded by the DNA of [1] when the protein encoded by the DNA of [α] allows expression of a gene within the test genomic fragment; and

[30] a kit for use in the screening method of any one of [25] to [29].

BRIEF DESCRIPTION OF THE DRAWINGS

FIG. 3-1 shows the result of PCR analysis of mutants (detection of deletions).

FIG. 3-2 shows a continuation of FIG. 3-1.

FIG. 4-1 shows phenotype-genotype correlation using mutants. (a) Complete deletion; (b) deletion 616-823 with a segmental 26-bp duplication and inversion; (c) one nucleotide after exon 1; (d) two nucleotides before start of exon 2; (e) six nucleotides before start of exon 3; FS, frame shift. The diagrams should be read as follows. For example, the diagrams show that Arg has been replaced with Leu at position 107 in the hex-v.42 mutant; in this case, nucleotides have been substituted from "cgc" to "ctc"; and also this substitution occurs in the homeodomain of exon 2. The same applies to the other mutants.

FIG. 4-2 shows a continuation of FIG. 4-1.

FIG. 4-3 shows a continuation of FIG. 4-2.

FIG. 4-4 shows a continuation of FIG. 4-3.

FIG. 4-5 shows a continuation of FIG. 4-4.

FIG. 4-6 shows a continuation of FIG. 4-5.

FIG. 4-7 shows a continuation of FIG. 4-6.

FIG. 4-8 shows a continuation of FIG. 4-7.

FIG. 4-9 shows a continuation of FIG. 4-8.

FIG. 4-10 shows a continuation of FIG. 4-9.

FIG. 4-11 shows a continuation of FIG. 4-10.

FIG. 5 is a photograph showing the result of the vrs1 gene expression analysis. The gene was expressed in young panicles but not in leaves. The transcript was detected in each of two-rowed varieties (K and B) and a six-rowed variety (A); however, a reading-frame shift had occurred in the six-rowed variety. H represents a six-rowed mutant created from the two-rowed variety (B). In this mutant, the transcript was not detected at all due to a large deletion in a region containing the gene. The two-rowed varieties had the functional Vrs1 gene. No mutations were found at the amino acid sequence level between the two-rowed varieties.

BEST MODE FOR CARRYING OUT THE INVENTION

The present invention provides a Vrs1 gene that confers barley with the two-row phenotype, mutant Vrs1 genes that confer barley with the two-row phenotype, mutant Vrs1 genes that confer barley with the six-row phenotype, and mutant Vrs1 genes that confer barley with a phenotype intermediate between the two-row and six-row types (Table 1).

TABLE 1

| Gene name used in this description | Name of plant having the gene indicated on the left | Phenotype of the plant indicated on the left |
|---|---|---|
| Vrs1 gene | Bonus, Foma, Kristina | Two-row type |
| Mutant Vrs1 genes involved in the two-row phenotype | Debre Zeit, OUH602 | |

TABLE 1-continued

| Gene name used in this description | Name of plant having the gene indicated on the left | Phenotype of the plant indicated on the left |
|---|---|---|
| Mutant Vrs1 genes involved in the six-row phenotype | Thirty-two hex-v mutant lines shown in Tables 2 and 3, Natsudaikon Mugi, Morex, AZ, Soren Oomugi 19329, Caveda Dissa, Hayakiso 2, Arlington Awnless | Six-row type |
| Mutant Vrs1 genes involved in a phenotype intermediate between the two-row and six-row types | Fifteen Int-d mutant lines shown in Tables 2 and 3, PI284755, OUH743 | Intermediate type between the two-row and six-row types |

The Vrs1 gene of the present invention includes:

(a) a DNA encoding a protein comprising the amino acid sequence of SEQ ID NO: 3; and (b) a DNA comprising the coding region of the nucleotide sequence of SEQ ID NO: 1 or 2.

Furthermore, the mutant Vrs1 genes that confer barley with the two-row phenotype (hereinafter sometimes referred to as "two row-type mutant Vrs1 genes") include:

(e) barley-derived DNAs that hybridize under stringent conditions to a DNA comprising the nucleotide sequence of SEQ ID NO: 1 or 2, and encode proteins functionally equivalent to a protein comprising the amino acid sequence of SEQ ID NO: 3.

Figure 1:
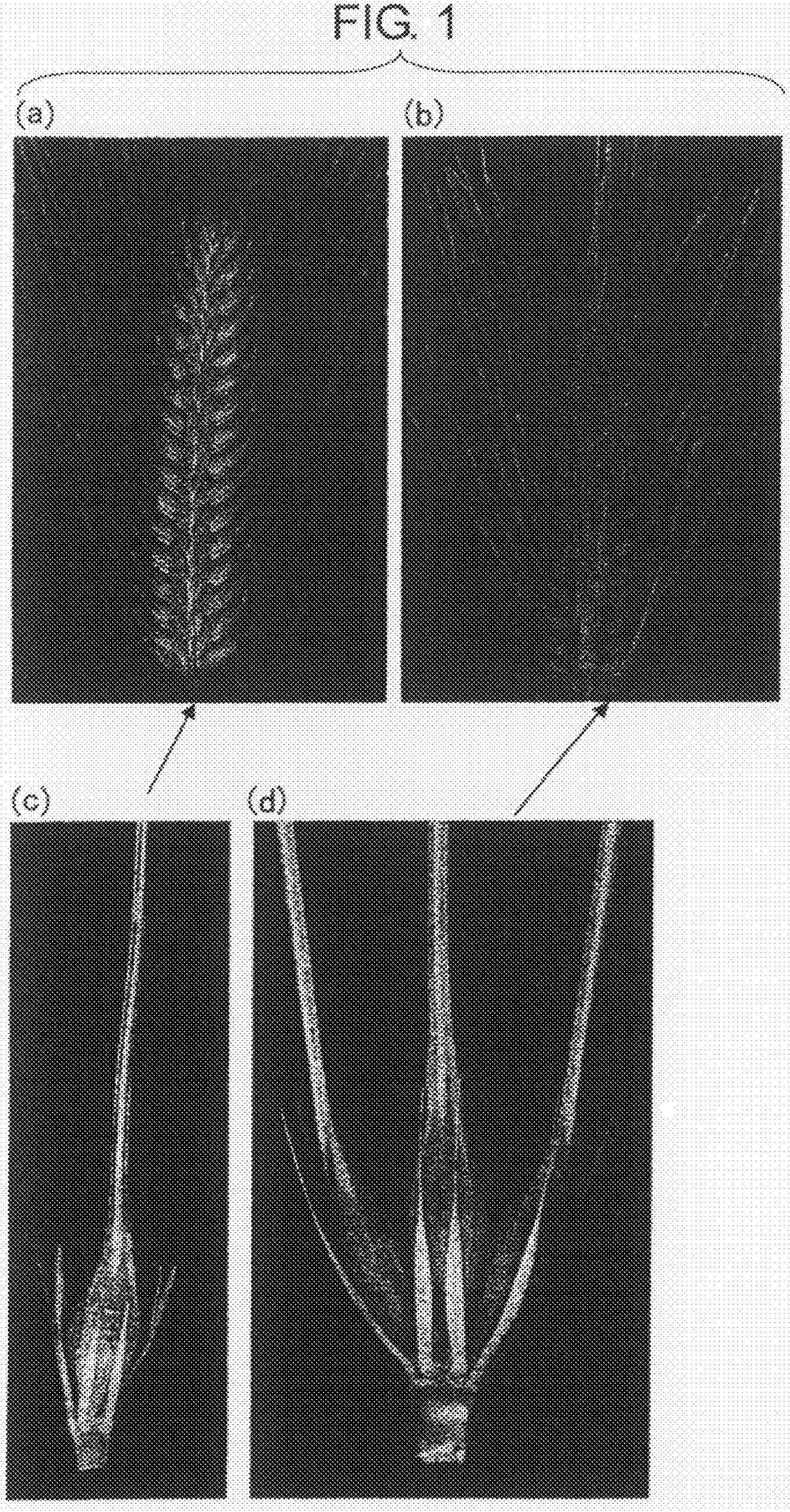
FIG. 1 shows photographs of panicles of two-rowed (a) and six-rowed (b) barley. Panicles are three-dimensional in six-rowed barley, while they are two-dimensional in two-rowed barley. Photographs (c) and (d) show three spikelets of two-rowed and six-rowed barley, respectively. Palea, lemma, stamen, and pistil are differentiated but poorly developed in lateral spikelets of two-rowed barley. In particular, pistil is infertile because it completely degenerates. In panicles of six-rowed barley, all three spikelets are fertile.
Figure 2:
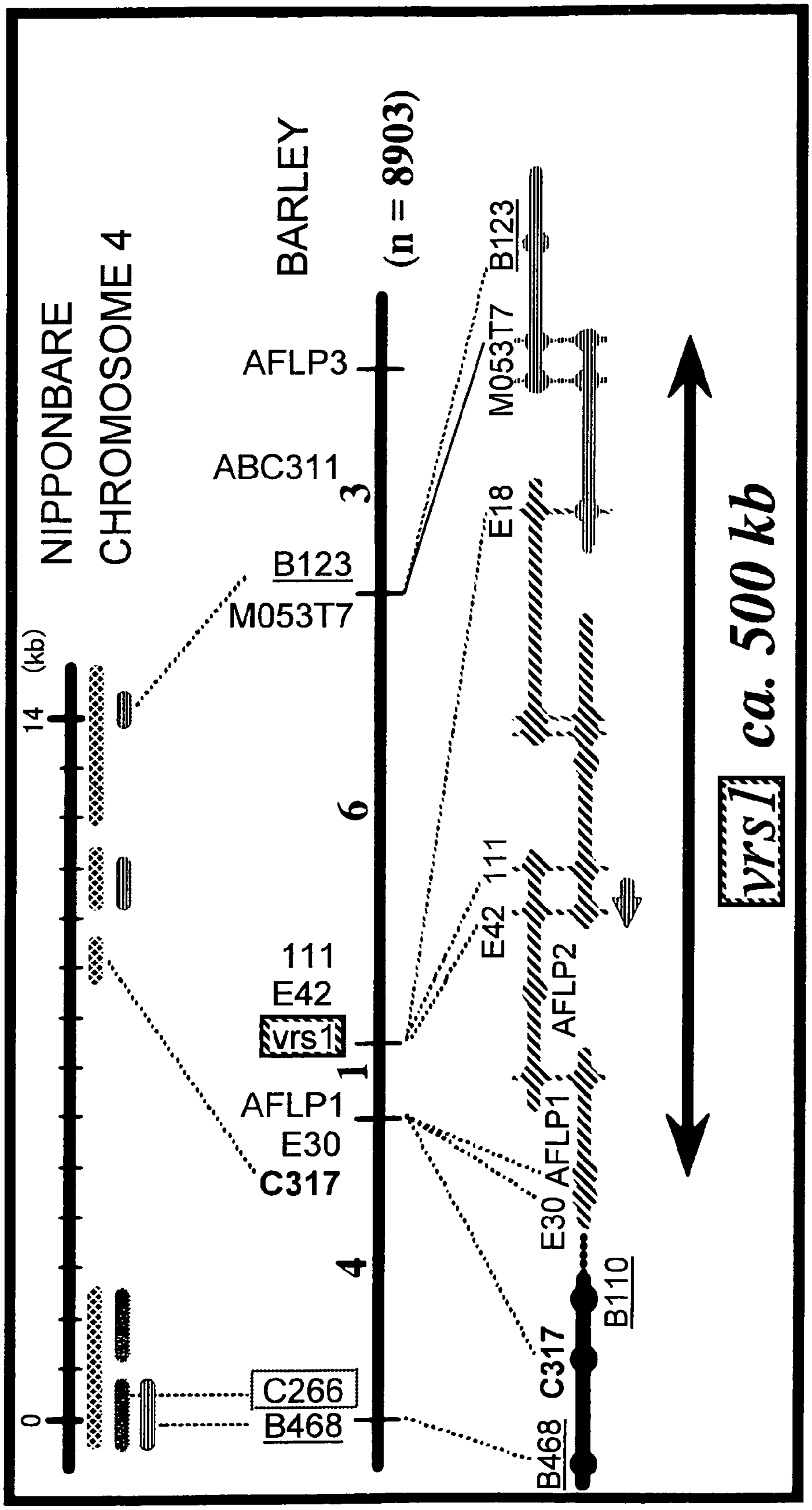
FIG. 2 shows the construction of a barley BAC contig containing the row-type gene vrs1. The molecular linkage maps are highly homologous between rice (upper) and barley (middle). The barley BAC contig is shown at the bottom. The presence of a candidate vrs1 gene was predicated (the short arrow in the center of the bottom map).

Herein, the two-row phenotype (hereinafter sometimes simply referred to as "two-row type") refers to a panicle phenotype in which lateral spikelets do not develop. Specific examples are the varieties Bonus, Foma, and Kristina (each comprises the nucleotide sequence of SEQ ID NO: 1), shown in FIG. 3-1.

In the present invention, a gene may result in the two-row phenotype even when it has a nucleotide sequence that is not perfectly identical to the nucleotide sequence of SEQ ID NO: 1 or 2, as long as the sequence difference does not significantly alter the function of the gene. Barley varieties exhibiting such a phenotype include, for example, Debre Zeit and OUH602 indicated in Table 3 and FIG. 4. The row type-determining gene of Debre Zeit has nucleotide mutations, A to G at position 694, T to G at position 873, and A to G at position 1446, in the nucleotide sequence of SEQ ID NO: 1. Thus, in the present invention, genes involved in the two-row phenotype also include barley-derived DNAs that hybridize under stringent conditions to a DNA comprising the nucleotide sequence of SEQ ID NO: 1 or 2, and encode proteins functionally equivalent to a protein comprising the amino acid sequence of SEQ ID NO: 3. In the present invention, the phrase "functionally equivalent" refers not only to having the same function as Vrs1 but also to having functions similar to those of the Vrs1 gene.

Furthermore, the present invention provides mutant Vrs1 genes that confer barley with the six-row phenotype (hereinafter sometimes referred to as "six row-type mutant Vrs1 genes"). Such mutants include:

(c) DNAs encoding proteins comprising an amino acid sequence with an artificial substitution, deletion, addition, and/or insertion of one or more amino acids in the amino acid sequence of SEQ ID NO: 3; and (d) barley-derived DNAs that hybridize under stringent conditions to a DNA comprising the nucleotide sequence of SEQ ID NO: 1 or 2.

The mutant Vrs1 genes that confer barley with the six-row phenotype include, for example, genes comprising a nucleotide sequence with a deletion of nucleotides at positions 1 to 2147 in the nucleotide sequence of SEQ ID NO: 1, such as hex-v.3, hex-v.10, hex-v.11, hex-v.18, hex-v.35, and hex-v.41, shown in Table 2 and FIG. 4. Furthermore, the 32 hex-v mutant lines and the Natsudaikon Mugi, Morex, A Z, Soren Oomugi 19329, Caveda, Dissa, Hayakiso 2, and Arlington Awnless varieties shown in FIG. 4 also have the six-row phenotype. Phenotypes such as awn elongation, thickening of palea and lemma, and seed production all tend to develop well in barley that has a mutation starting with hex-v. In these mutants, respective DNA mutations result in alterations in the amino acid sequences, and thus the phenotype is switched to be six-rowed. Herein, the six-row phenotype (hereinafter sometimes simply referred to as "six-row type") refers to a panicle phenotype in which the degree of lateral spikelet development is comparable to that of the central spikelet.

Furthermore, the present invention provides mutant Vrs1 genes that confer barley with a phenotype intermediate between the two-row and six-row types (hereinafter sometimes referred to as "intermediate-type mutant Vrs1 genes"). Such mutants include:

(c) DNAs encoding proteins comprising an amino acid sequence with an artificial substitution, deletion, addition, and/or insertion of one or more amino acids in the amino acid sequence of SEQ ID NO: 3; and (d) barley-derived DNAs that hybridize under stringent conditions to a DNA comprising the nucleotide sequence of SEQ ID NO: 1 or 2.

The mutant Vrs1 genes that confer barley with a phenotype intermediate between the two-row and six-row types include 15 Int-d mutant lines shown in Table 2 and FIG. 4. The mutants starting with Int-d tend to develop poorly with regard to phenotypes such as awn elongation, thickening of palea and lemma, and seed production. The naturally-occurring lines PI284755 and OUH74 listed in FIG. 4 are also included in the mutant Vrs1 that confers barley with a phenotype intermediate between the two-row and six-row types. In these mutants, respective DNA mutations result in alterations in the amino acid sequences, and thus change the row type. Herein, the phenotype intermediate between the two-row and six-row types (hereinafter sometimes simply referred to as the "intermediate type") refers to a phenotype in which panicles are of the intermediate type between the two-row and six-row types and the lateral spikelets develop partially.

More specifically, such a phenotype intermediate between the two-row and six-row types include the following phenotypes. Awns of lateral lemma elongate in mutants created from two-rowed barley (mutants having a phenotype intermediate between the two-row and six-row types), whereas no awns of lateral spikelets elongate in two-rowed barley. The degree of elongation ranges from almost no elongation, with a very short pointed tip like a prickle, to considerable elongation comparable to that of the central spikelets, so that the panicle appearance is comparable to normal six-rowed varieties; and this indicates continuous mutations. Furthermore, palea and lemma of spikelets are thickened in mutants created from two-rowed barley (mutants having a phenotype intermediate between the two-row and six-row types), while those of lateral spikelets are not thickened and are thus smaller than those of the central spikelets in two-rowed barley. The degree of thickening ranges from very slight thickening, close to that of the two-row type, to great thickening comparable to that of normal six-rowed varieties; and this indicates continuous mutations. The lateral spikelets of the two-rowed varieties show no seed fertility, while lateral spikelets of mutants created from two-rowed barley, which are mutants having a phenotype intermediate between the two-row and six-row types, range from those showing no seed fertility to those of which several tens percent produce seeds; and this indicates continuous mutations. Thus, representative phenotypes that are influenced by mutations include awn elongation, thickening of palea and lemma, and seed production in lateral spikelets. However, phenotypes that are influenced by mutations are not limited to them, because the row-type genes of the present invention regulate the size of tiny organs in lateral spikelets overall.

Herein, two row-type mutant Vrs1 genes, six row-type mutant Vrs1 genes, and mutant Vrs1 genes of an intermediate type between the two-row and six-row types are collectively called "mutant Vrs1 genes".

TABLE 2

| Mutant # | Original cv. | Mutagen | Event at DNA | Effect on protein |
|---|---|---|---|---|
| hex-v.03 | Bonus | Neutrons | 1-2147 del. | Null |
| hex-v.10 | Bonus | X-rayed pollen | 1-2147 del. | Null |
| hex-v.11 | Bonus | X-rayed pollen | 1-2147 del. | Null |
| hex-v.18 | Bonus | X-rays | 1-2147 del. | Null |
| hex-v.35 | Foma | Gamma-rays | 1-2147 del. | Null |
| hex-v.41 | Kristina | Neutrons | 1-2147 del. | Null |
| hex-v.15 | Foma | Gamma-rays | 616-823 del. with 26pb dupl. and inv. | |
| hex-v.04 | Bonus | X-rays | 701 C to — | Asn11 to Thr then FS |
| hex-v.49 | Bonus | Sodium azide | 733 G to A | Splicing site |
| hex-v.38 | Kristina | Iso-Propyl methanesulfonate | 855 A to C | Splicing site |
| hex-v.17 | Foma | Ethyl methanesulfonate | 865 C to T | Gln24 to Stop |
| hex-v.44 | Bonus | Iso-Propyl methanesulfonate | 958 G to T | Gly55 to Stop |
| hex-v.45 | Bonus | Iso-Propyl methanesulfonate | 958 G to T | Gly55 to Stop |
| hex-v.12 | Bonus | Neutrons | 1018 T to A | Phe75 to Ile |
| hex-v.13 | Foma | X-rays | 1018 T to A | Phe75 to Ile |
| hex-v.14 | Foma | Glycidol | l018 T to A | Phe75 to Ile |
| Int-d.12 | Foma | Ethylene imine | 1049 G to A | Arg85 to His |
| Int-d.28 | Foma | Iso-Propyl methanesulfonate | 1049 G to A | Arg85 to His |
| hex-v.39 | Kristina | Iso-Propyl methanesulfonate | 1061 T to A | Leu89 to Gln |
| Int-d.50 | Kristina | Gamma-rays | 1061 T to A | Leu89 to Gln |
| hex-v.36 | Kristina | Ethyl methanesulfonate | 1064 C to T | Ala90 to Val |
| hex-v.25 | Foma | Ethylene imine | 1073 T to A | Leu93 to His |
| hex-v.26 | Foma | Ethyl methanesulfonate | 1073 T to A | Leu93 to His |
| hex-v.28 | Foma | Ethylene imine | 1079 T to A | Leu95 to Gln |
| Int-d.68 | Kristina | Ethyl methanesulfonate | 1079 T to A | Leu95 to Gln |
| hex-v.29 | Foma | Ethylene imine | 1102 T to A | Trp103 to Arg |
| Int-d.67 | Kristina | Ethyl methanesulfonate | 1108 C to T | Gln105 to Stop |
| Int-d.41 | Kristina | Ethyl hydroxy ethanesulfonate | 1111 A to T | Asn106 to Tyr |
| hex-v.42 | Kristina | Neutrons | 1115 G to T | Arg107 to Leu |
| hex-v.43 | Kristina | Ethyl methanesulfonate | 1115 G to T | Arg107 to Leu |
| Int-d.22 | Foma | Methyl methanesulfonate | 1124 G to A | Arg110 to His |
| Int-d.24 | Foma | Buthyl methanesulfonate | 1124 G to A | Arg110 to His |
| hex-v.22 | Foma | Neutrons + Ethyl methanesulfonate | 1135 A to T | Lys114 to Stop |
| hex-v.23 | Foma | Ethylene imine | 1135 A to T | Lys114 to Stop |
| hex-v.24 | Foma | Propanedisulfonic acid diethyl ester | 1135 A to T | Lys114 to Stop |
| Int-d.57 | Kristina | Iso-Propyl methanesulfonate | 1193 A to C | His133 to Pro |
| Int-d.73 | Bonus | Ethyl methanesulfonate | 1193 A to C | His133 to Pro |
| hex-v.21 | Foma | Ethyl methanesulfonate | 1195 A to T | Lys134 to Stop |
| hex-v.19 | Foma | Methyl methanesulfonate | 1213 G to T | Glu140 to Stop |
| Int-d.82 | Bonus | Ethyl methanesulfonate | 1311 G to A | Splicing site putative |
| Int-d.69 | Kristina | Ethyl methanesulfonate | 1335 A to T | Arg147 to Stop |
| Int-d.11 | Foma | Ethylene imine | 1476 T to A | Cys194 to Ser |
| Int-d.36 | Foma | Ethyl methanesulfonate | 1482 C to T | Gln196 to Stop |
| Int-d.40 | Kristina | Ethyl methanesulfonate | 1485 C to T | Gln 197 to Stop |
| hex-v.27 | Foma | N-ethyl-N-nitrosourea | 1504-1514 del. | Ala203 to Gly then FS |
| hex-v.30 | Foma | Gamma-rays | 1504-1514 del. | Ala203 to Gly then FS |
| hex-v.31 | Foma | Ethylene imine | 1504-1514 del. | Ala203 to Gly then FS |

TABLE 3

| Mutagen | Event at DNA | Effect on protein | 2nd event at DNA | 2nd effect on protein | 3rd event at DNA | 3rd effect on protein | 4th event at DNA | 4th effect on protein |
|---|---|---|---|---|---|---|---|---|
| Natsudaikon Mugi | 1020 C to G | Phe75 to Leu | | | | | | |
| Morex | 694 A to G | Asp8 to Gly | 873 T to G | Asp26 to Glu | 1352 G to — | Glu152 to Asp then FS | | |
| AZ | 694 A to G | Asp8 to Gly | 873 T to G | Asp26 to Glu | 1352 G to — | Glu152 to Asp then FS | | |
| Soren oomugi 19329 | 694 A to G | Asp8 to Gly | 873 T to G | Asp26 to Glu | 1352 G to — | Glu152 to Asp then FS | | |

TABLE 3-continued

| Mutagen | Event at DNA | Effect on protein | 2nd event at DNA | 2nd effect on protein | 3rd event at DNA | 3rd effect on protein | 4th event at DNA | 4th effect on protein |
|---|---|---|---|---|---|---|---|---|
| Caveda | 694 A to G | Asp8 to Gly | 873 T to G | Asp26 to Glu | 914-915 T ins. | Arg41 to Glu then FS | | |
| Dissa | 694 A to G | Asp8 to Gly | 873 T to G | Asp26 to Glu | 914-915 T ins. | Arg41 to Glu then FS | | |
| Hayakiso 2 | 694 A to G | Asp8 to Gly | 873 T to G | Asp26 to Glu | | | | |
| Arlington | 694 A to G | Asp8 to Gly | 873 T to G | Asp26 to Glu | | | | |
| PI284755 | 694 A to G | Asp8 to Gly | 873 T to G | Asp26 to Glu | | | | |
| OUH743 | 694 A to G | Asp8 to Gly | 873 T to G | Asp26 to Glu | 1097 C to T | Ala101 to Val | | |
| OUH602 | 694 A to G | Asp8 to Gly | 873 T to G | Asp26 to Glu | 1386 G to C | Ser164 to Thr | 1423 G to A | Gly176 to Asp |
| Debre Zeit 29 | 694 A to G | Asp8 to Gly | 873 T to G | Asp26 to Glu | 1446 A to G | Ser184 to Gly | | |

For example, "1049 G to A" in the row of "Mutant Int-d.12" and the column of "Event at DNA" of Table 2 means that "in the Int-d.12 mutant, G at nucleotide position 1049 in the nucleotide sequence of SEQ ID NO: 1 has been replaced with A". The nucleotide at position 1049 in the nucleotide sequence of SEQ ID NO: 1 corresponds to the nucleotide at position 406 in the nucleotide sequence of SEQ ID NO: 2. The nucleotide mutation results in substitution of His for Arg at position 85 in the amino acid sequence of SEQ ID NO: 3. Likewise, for example, "1115 G to T" in the row of "Mutant hex-v.42" and the column of "Event at DNA" of Table 2 means that "in the mutant hex-v.42, G at position 1115 in the nucleotide sequence of SEQ ID NO: 1 has been replaced with T". The nucleotide at position 1115 in the nucleotide sequence of SEQ ID NO: 1 corresponds to the nucleotide at position 472 in the nucleotide sequence of SEQ ID NO: 2. The nucleotide mutation results in substitution of Leu for Arg at position 107 in the amino acid sequence of SEQ ID NO: 3. Like Table 2, Table 3 shows the mutation site for each mutant in the nucleotide sequence of SEQ ID NO: 1 and the corresponding amino acid substitution. Those skilled in the art can create desired mutants by appropriately referring to these tables. The mutant Vrs1 genes of the present invention are mutants resulting from various sequence alterations such as nucleotide deletions, frameshifts, and appearance of a stop codon in the Vrs1 gene.

Barley is being distributed on the market as a plant for floral arrangement. Thus, barley altered to be two-rowed, six-rowed, or of an intermediate type between the two-row and six-row types can be used in floral arrangement, and is useful as an ornamental plant. In particular, barley altered to be an intermediate type between the two-row and six-row types is valuable as a variant. Shapes that meet the purpose can be created by altering the balance between the central and lateral rows in panicles using the Vrs1 gene of the present invention or a mutant thereof.

The "Vrs1 gene" of the present invention is not particularly limited, as long as it can encode the "Vrs1 protein". The "Vrs1 gene" comprises not only cDNAs but also genomic DNAs and chemically synthesized DNAs. Furthermore, the Vrs1 gene includes DNAs comprising any nucleotide sequence based on the degeneracy of genetic code as long as it encodes the Vrs1 protein. Likewise, there is no limitation on the type of mutant Vrs1 genes of the present invention, as long as they can encode the protein. The mutants include not only cDNAs but also genomic DNAs and chemically synthesized DNAs.

One skilled in the art can prepare genomic DNAs and cDNAs by using conventional means. Genomic DNAs can be prepared, for example, by extracting genomic DNAs from a plant; constructing a genomic library (a plasmid, phage, cosmid, BAC, PAC or the like can be used as a vector); developing it; and performing colony hybridization or plaque hybridization using a probe prepared based on the Vrs1 gene (for example, the DNA of SEQ ID NO: 1 or 2) or the mutant Vrs1 genes. Alternatively, genomic DNAs can be prepared by preparing primers specific for the Vrs1 gene or the mutant Vrs1 genes and performing PCR by using these primers. cDNAs can be prepared, for example, by synthesizing cDNAs based on mRNAs extracted from a plant; inserting them into vectors such as λZAP to create a cDNA library; developing it; and performing colony hybridization or plaque hybridization as described above. They can also be prepared by performing PCR.

Methods well known to one skilled in the art for isolating the Vrs1 gene or mutants thereof include the hybridization technique (Southern E. M., Journal of Molecular Biology 98, 503, 1975) and the polymerase chain reaction (PCR) technique (Saiki, R. K., et al., Science 230, 1350-1354, 1985; Saiki, R. K. et al., Science 239, 487-491, 1988). Specifically, one skilled in the art can usually isolate the Vrs1 gene or mutant Vrs1 genes from barley, by using as a probe a DNA comprising the nucleotide sequence of SEQ ID NO: 1 or 2, or a part thereof, or by using as primers oligonucleotides which specifically hybridize to a DNA comprising the nucleotide sequence of SEQ ID NO: 1 or 2.

In general, hybridization reaction is carried out under stringent conditions to isolate such DNAs encoding the Vrs1 gene or mutants thereof. Those skilled in the art can appropriately select stringent hybridization conditions to isolate DNAs encoding the Vrs1 gene or mutants thereof. For example, pre-hybridization is carried out at 42° C. overnight in a hybridization solution containing 25% formamide, or 50% formamide for more stringent conditions, and 4×SSC, 50 mM Hepes (pH 7.0), 10×Denhardt's solution, and 20 μg/ml denatured salmon sperm DNA. Then, a labeled probe is added to the solution and hybridization is carried out by incubation at 42° C. overnight. Post-hybridization washes are carried out under the conditions of about "1×SSC, 0.1% SDS, 37° C.", more stringently "0.5×SSC, 0.1% SDS, 42° C.", or even more stringently "0.2×SSC, 0.1% SDS, 65° C.". As the stringency of the post-hybridization washes increases, DNAs with higher homology to the probe sequence are expected to be isolated. However, the above combinations of conditions for SSC, SDS, and temperature are only examples, and those skilled in the art can achieve stringencies equivalent to the above by appropriately combining the above or other factors determining hybridization stringency (for example, probe concentration, probe length, hybridization reaction time, and so forth). Homology of isolated DNAs indicates a sequence identity of at least 50% or more, more preferably 70% or more, still more preferably 90% or more (for example, 95%, 96%, 97%, 98%, 99% or more) over the entire amino acid sequence. Sequence homology can be determined using the programs of BLASTN (nucleic acid level) or BLASTX (amino acid level) (Altschul et al., J. Mol. Biol. 215, 403-410, 1990). The programs are based on the algorithm BLAST by Karlin and Altschul (Proc. Natl. Acad. Sci. USA 87, 2264-2268, 1990; Proc. Natl. Acad. Sci. USA 90, 5873-5877, 1993). When analyzing a nucleotide sequence by BLASTN, parameters are set to, for example, score=100 and wordlength=12. When analyzing an amino acid sequence by BLASTX, parameters are, for example, set to score=50 and wordlength=3. Alternatively, an amino acid sequence can be analyzed using Gapped BLAST program as indicated by Altschul et al. (Nucleic Acids Res. 25, 3389-3402, 1997). When BLAST and Gapped BLAST programs are used, the default parameters of each program are used. The specific procedures of these analysis methods are known.

In the present invention, mutants of the Vrs1 gene can also be obtained through induction of mutations in the Vrs1 gene by irradiating wild-type barley with electromagnetic waves such as neutron, X-ray, or gamma ray.

In the present invention, the barley species is not particularly limited and any species is acceptable as long as it belongs to the genus *Hordeum*. Hybrid or crossbred varieties between cultivar and wild barley are also acceptable. Wild barley includes, but is not limited to, for example, *Hordeum* vukgare ssp. Spontaneum. Cultivars of barley include, but are not limited to, for example, *Hordeum* vukgare ssp. Vulgare.

Furthermore, the present invention provides DNAs used to suppress the expression of the endogenous barley Vrs1 gene or a mutant thereof, which comprise:

(a) DNAs encoding an RNA complementary to the transcript of the Vrs1 gene or a mutant thereof;
(b) DNAs encoding an RNA having a ribozyme activity of specifically cleaving the transcript of the Vrs1 gene or a mutant thereof;
(c) DNAs encoding an RNA that inhibits the expression of the Vrs1 gene or a mutant thereof by co-suppression effect; or
(d) DNAs encoding an RNA having an RNAi activity of specifically cleaving the transcript of the Vrs1 gene or a mutant thereof.

These DNAs can be used to alter the row type or panicle morphology of barley. For example, the two-row phenotype or panicle morphology of barley can be altered by suppressing the expression of the endogenous Vrs1 gene in two-rowed barley. Alteration of the row type or panicle morphology of barley is useful in creating barley with a desired phenotype. Barley with altered row type or panicle morphology can be used, for example, in floral arrangement, and thus it is useful in the field of ornamental plants.

There is no limitation on the type of barley in which the expression of the Vrs1 gene or a mutant thereof is to be suppressed Any barley whose panicle morphology needs to be altered may be used.

As used herein, "suppression of the Vrs1 gene or mutant Vrs1 gene expression" includes suppression of gene transcription and suppression of translation to a protein. Moreover, it includes not only the complete arrest of DNA expression, but also reduction of expression.

One embodiment of "a DNA used to suppress the expression of the Vrs1 gene or a mutant thereof" is a DNA which encodes an antisense RNA complementary to the Vrs1 gene or a mutant thereof. Using the temporal gene expression method, the antisense effect in a plant cell was demonstrated for the first time through the fact that an antisense RNA introduced by electroporation exhibited an antisense effect in a plant (Ecker and Davis, Proc. Natl. Acad. USA 83, 5372, 1986). Thereafter, expression of antisense RNAs in tobacco and petunia has also been reported to reduce target gene expression (Krol et al., Nature 333, 866, 1988). At present, it is established as a means to suppress gene expression in plants.

There are multiple factors involved in the action of antisense nucleic acids in suppressing target gene expression, as indicated as follows: inhibiting transcription initiation by forming triple strands; suppressing transcription by hybridizing with a site where RNA polymerase has formed a local open loop structure; inhibiting transcription by hybridizing with the RNA being synthesized; suppressing splicing by hybridizing with an intron-exon junction; suppressing splicing by hybridizing with the site of spliceosome formation; suppressing transfer from the nucleus to the cytoplasm by hybridizing with an mRNA; suppressing splicing by hybridizing with a poly(A) addition site or capping site; suppressing translation initiation by hybridizing with a translation initiation factor binding site; suppressing translation by hybridizing with a ribosome binding site near the initiation codon; preventing peptide chain elongation by hybridizing with an mRNA translation region or polysome binding site; and suppressing gene expression by hybridizing with a nucleic acid-protein interaction site. Antisense nucleic acids suppress target gene expression by inhibiting transcription, splicing, or translation process (Hirashima and Inoue, "Shin Seikagaku Jikken Kouza (New Biochemistry Experimentation Lectures) 2, Kakusan (Nucleic Acids) IV, Idenshi no Fukusei to Hatsugen (Replication and Expression of Genes)", The Japanese Biochemical Society Ed., Tokyo Kagaku Dojin, pp. 319-347, 1993).

The antisense sequences used in the present invention can suppress the expression of a target gene by any of the above actions. As one embodiment, an antisense sequence designed to be complementary to an untranslated region close to the 5' end of the mRNA of a gene will be effective in inhibiting translation of that gene. However, a sequence complementary to a coding region, or to a 3'-end untranslated region can also be used. In this way, DNAs comprising antisense sequences of a gene's translated regions as well untranslated regions are included in the antisense DNAs that can be used in the present invention. An antisense DNA to be used herein is ligated downstream of an appropriate promoter, and a sequence comprising a transcription termination signal is preferably ligated to the 3' side of the DNA.

Antisense DNAs can be prepared, for example, based on the DNA sequence of SEQ ID NO: 1 or 2 by using the phosphorothioate method (Stein, Nucleic Acids Res. 16, 3209-3221, 1988) and such. DNAs thus prepared can be transformed into a desired plant using known methods. Antisense DNA sequences are preferably sequences complementary to a transcript of an endogenous gene of the plant to be transformed, but need not be perfectly complementary as long as they can effectively inhibit gene expression. The transcribed RNAs are preferably 90% or more (for example, 95%, 96%, 97%, 98%, 99% or more) complementary to the transcripts of the target genes. In order to effectively inhibit target gene expression using an antisense sequence, an antisense DNA should comprise at least 15 nucleotides or more, preferably 100 nucleotides or more, and even more preferably 500 nucleotides or more. Antisense DNAs to be used are generally less than 5 kb, and preferably less than 2.5 kb long.

Suppression of the endogenous Vrs1 gene expression can also be carried out using DNAs encoding ribozymes. "Ribozyme" refers to an RNA molecule having catalytic activity. Some ribozymes have many different activities. Among them, research on ribozymes as RNA-cleaving enzymes has enabled designing ribozymes to cleave RNAs at specific sites. Ribozymes include those of 400 nucleotides or more, such as MIRNA in RNaseP, or the group I intron type ribozymes. In contrast, there are also hammerhead-type or hairpin-type ribozymes that comprise an active domain of about 40 nucleotides (Koizumi, M. and Ohtsuka, E., Protein, Nucleic Acid and Enzyme 35, 2191, 1990).

For example, the self-cleaving domain of a hammerhead type ribozyme cleaves at the 3' side of C15 in G13U14C15. Base pairing between U14 and A9 is important for ribozyme activity. It has been shown that cleavage can occur if A or U instead of C is at the 15th position (Koizumi, M. et al., FEBS Lett. 228, 225, 1988). If the substrate-binding site of the ribozyme is designed to be complementary to the RNA sequences adjacent to the target site, a restriction enzyme-like RNA-cleaving ribozyme can be created that recognizes the sequence UC, UU, or UA within the target RNA (Koizumi et al., FEBS Lett. 239, 285, 1988; Koizumi, M. and Ohtsuka, E., Protein, Nucleic Acid and Enzyme 35, 2191, 1990; Koizumi et al., Nucleic Acids Res. 17, 7059, 1989).

Hairpin type ribozymes are also useful for objectives of the present invention. A hairpin type ribozyme can be found, for example, in the minus strand of tobacco ringspot virus satellite RNA (Buzayan, Nature 323, 349, 1986). It has also been shown that this ribozyme can be designed to target-specifically cleave an RNA (Kikuchi and Sasaki, Nucleic Acids Res. 19, 6751, 1992; Kikuchi, H., Kagaku to Seibutsu (Chemistry and Biology) 30, 112, 1992).

In order to be transcribed in plant cells, a ribozyme designed to cleave a target is linked to a transcription termination sequence or a promoter such as the cauliflower mosaic virus 35S promoter. However, if extra sequences are added to the 5'-or the 3'-end of the transcribed RNA, the ribozyme activity can be lost. In this case, another cis-acting trimming ribozyme can be placed in the 5' or 3' side of the ribozyme portion to precisely trim only the ribozyme portion from the transcribed RNA comprising the ribozyme (Taira et al., Protein Eng. 3, 733, 1990; Dzianott and Bujarski, Proc. Natl. Acad. Sci. USA 86, 4823, 1989; Grosshans and Cech, Nucleic Acids Res. 19, 3875, 1991; Taira et al., Nucleic Acid Res. 19, 5125, 1991).

In addition, these structural units can be arranged in tandem to cleave multiple sites within a target gene, thus achieving greater effects (Yuyama et al., Biochem. Biophys. Res. Commun. 186, 1271, 1992). By using these kinds of ribozymes, the transcripts of the target genes of the present invention can be specifically cleaved, and the gene expression can be suppressed.

Suppression of endogenous gene expression can also be achieved by "co-suppression" resulting from transformation with a DNA comprising a sequence identical or similar to a target gene sequence. The term "co-suppression" refers to the phenomenon in which, when a gene comprising a sequence identical or similar to that of the target endogenous gene is introduced into plants by transformation, expression of both the introduced exogenous gene and the target endogenous gene is suppressed. The detailed mechanism of co-suppression is unknown, but it is frequently observed in plants (Curr. Biol. 7, R793, 1997; Curr. Biol. 6, 810, 1996).

For example, to obtain a plant in which the Vrs1 gene or a mutant thereof is co-suppressed, plants of interest are transformed with a vector DNA constructed to express a DNA comprising a sequence identical or similar to the Vrs1 gene or a mutant thereof, and plants with a characteristic of suppressed Vrs1 or Vrs1 mutant function, are selected from the plants thus obtained. Genes to be used for co-suppression do not have to be completely identical to the target gene; however, they have sequence identity of at least 70% or more, preferably 80% or more, and more preferably 90% or more (for example, 95%, 96%, 97%, 98%, 99% or more).

In addition, suppression of endogenous gene expression in the present invention can also be achieved by transforming a plant with a gene comprising a characteristic that is dominant-negative to the target gene. A "gene comprising a dominant-negative characteristic" refers to a gene that, when expressed, has the function of eliminating or reducing the activity of an original endogenous wild-type gene of the plant.

Another embodiment of "a DNA used to suppress the expression of Vrs1 gene or a mutant thereof" is a DNA which encodes a double-stranded RNA (dsRNA) complementary to a transcript of an endogenous Vrs1 gene or a mutant thereof. By introducing a dsRNA comprising a sequence identical or similar to a target gene sequence into a cell, a phenomenon called RNAi (RNA interference) can be caused, where expression of both the introduced foreign gene and the target endogenous gene are suppressed. When a dsRNA of about 40 to several hundred base pairs is introduced into a cell, an RNase III-like nuclease comprising a helicase domain, called Dicer, cuts out about 21 to 23 base pair portions from the 3'-terminus of the dsRNA in the presence of ATP, thereby producing an siRNA (short interference RNA). This siRNA binds to a specific protein to form a nuclease complex (RISC: RNA-induced silencing complex). This complex recognizes and binds to a sequence identical to the siRNA, and cuts the transcript (mRNA) of the target gene at the central part of the siRNA with the RNaseIII-like enzymatic activity. Apart from this pathway, an antisense strand of siRNA binds to an mRNA to act as a primer of an RNA-dependent RNA polymerase (RsRP), thereby synthesizing a dsRNA. Another pathway is also considered in which this dsRNA serves again as a substrate of Dicer, produces a new siRNA, and amplifies its effect.

RNAi was first discovered in nematodes (Fire, A. et al. Potent and specific genetic interference by double-stranded RNA in *Caenorhabditis elegans*. Nature 391, 806-811, 1998). At present, it is observed not only in nematodes, but also in various organisms such as plants, Nemathelminthes, *Drosophila*, and protozoa (Fire, A. RNA-triggered gene silencing. Trends Genet. 15, 358-363, 1999; Sharp, P. A., RNA interference 2001. Genes Dev. 15, 485-490, 2001; Hammond, S. M., Caudy, A. A. & Hannon, G. J. Post-transcriptional gene silencing by double-stranded RNA. Nature Rev. Genet. 2, 110-119, 2001; Zamore, P. D. RNA interference: listening to the sound of silence. Nat Struct Biol. 8, 746-750, 2001). In these organisms, it was confirmed that target gene expression was actually suppressed by externally introducing a dsRNA. Further, RNAi is now being used as a method for creating knockout organisms.

When RNAi was initially found, only a dsRNA of a certain length (40 bases) or more was thought to be effective. However, Tuschl et al. of Rockefeller University, United States, reported that by introducing a short dsRNA (siRNA) of about 21 base pairs into a cell, an RNAi effect was obtained in a mammalian cell without causing an antiviral reaction by PKR (Tuschl, Nature 411, 494-498, 2001). Thus, RNAi has suddenly attracted attention as a technique applicable to differentiated mammalian cells such as human cells.

The DNAs of the present invention comprise an antisense code DNA encoding an antisense RNA corresponding to any region of a transcript (mRNA) of a target gene, and a sense code DNA encoding a sense RNA corresponding to any region of the mRNA. The above-mentioned antisense RNA and sense RNA can be expressed from the above-mentioned antisense code DNA and sense code DNA. A dsRNA can also be produced from these antisense RNA and sense RNA. A target sequence in the present invention is not particularly limited, as long as the expression of the Vrs1 gene or a mutant thereof is suppressed by introducing into a cell a dsRNA comprising a sequence identical or similar to the target sequence. An example of the target sequence includes a sequence of 3'-untranslated region of the Vrs1 gene or a mutant thereof.

An expression system of dsRNAs of the present invention is maintained as follows in a vector or the like: an antisense RNA and a sense RNA are expressed from the same vector; or an antisense RNA and a sense RNA are expressed from different vectors, respectively. For example, when expressing an antisense RNA and a sense RNA from the same vector, an antisense RNA expression cassette and sense RNA expression cassette are each constructed, in which a promoter like the pol III system that can express a short RNA is connected upstream of the antisense code DNA and sense code DNA, respectively, and these cassettes are then inserted into a vector in the same direction or in the opposite direction.

An expression system can also be constructed in which an antisense code DNA and a sense code DNA are arranged in opposite directions on different strands so that they face each other. This construct can carry one double-stranded DNA (siRNA code DNA) in which an antisense RNA-encoding strand and a sense RNA-encoding strand are paired, and promoters which are oppositely oriented on both sides so that the antisense RNA and the sense RNA can be expressed from each strand. In this case, in order to prevent addition of an excess sequence downstream of the sense RNA and the antisense RNA, a terminator is preferably placed at the 3'-terminus of each strand (the antisense RNA-encoding strand and the sense RNA-encoding strand). A sequence of four or more consecutive A (adenine) bases can be used for this terminator. Moreover, in this palindrome type expression system, the kinds of two promoters are preferably different to each other.

When expressing an antisense RNA and sense RNA from different vectors, for example, the following procedures are performed: An antisense RNA expression cassette and a sense RNA expression cassette are constructed, in each of which a promoter such as the pol III system that can express a short RNA, is connected upstream of the antisense code DNA or the sense code DNA; and then these cassettes are maintained in different vectors.

As for RNAi, an siRNA may be used as a dsRNA. The term "siRNA" means a double-stranded RNA including short strands that exhibit no toxicity within a cell, and is not limited to the full length of 21 to 23 base pairs reported by Tuschl et al. (ibid.); and is not particularly limited, as long as the length is in such a range that it exhibits no toxicity. For example, an siRNA can be 15 to 49 base pairs, preferably 15 to 35 base pairs, and still more preferably 21 to 30 base pairs in length. Alternatively, length of the final double-stranded RNA portion that results from transcription of an siRNA to be expressed, can be 15 to 49 base pairs, preferably 15 to 35 base pairs, and more preferably 21 to 30 base pairs, for example.

As a DNA of the present invention, such a construct that is produced by inserting a suitable sequence (an intron sequence is preferable) between the inverted repeats of a target sequence and yields a double-stranded RNA having a hairpin structure (self-complementary 'hairpin' RNA (hpRNA)) (Smith, N. A., et al., Nature 407, 319, 2000; Wesley; S. V. et al., Plant J. 27, 581, 2001; Piccin, A. et al., Nucleic Acids Res. 29, E55, 2001), can also be used.

Although a DNA used for RNAi is not required to be completely the same as a target gene, it has a sequence identity of at least 70% or more, preferably 80% or more, still more preferably 90% or more (for example, 95%, 96%, 97%, 98%, 99% or more). The sequence identity can be determined by using the above-mentioned procedures.

The double-stranded RNA portions in dsRNAs, in which RNAs are paired, are not necessarily completely paired, but may comprise unpaired portions due to a mismatch (corresponding bases are not complementary), a bulge (there is no corresponding base on one strand) or the like. In the present invention, both bulges and mismatches may be included in double-stranded RNA regions where RNAs are paired with each other in dsRNAs.

The present invention also provides vectors, transformed cells, and transformed barley cells comprising any one of the Vrs1 gene, a mutant Vrs1 gene, and a DNA that suppress the Vrs1 gene expression.

With regard to the above vectors, for example, when the host is *Escherichia coli* (*E. coli*), as long as the vector has an "ori" for amplification in *E. coli*, such that vectors are amplified and prepared in large quantities in *E. coli* (for example, JM109, DH5α, HB101, and XL1 Blue) or such, and further has a selection gene for transformed *E. coli* (for example, a drug resistance gene that allows discrimination using a certain drug (ampicillin, tetracycline, kanamycin, or chloramphenicol)), the vectors are not particularly limited. The vectors include, for example, M13 vectors, pUC vectors, pBR322, pBluescript, and pCR-Script. In addition to the above vectors, for example, pGEM-T, pDIRECT, and pT7 can also be used for the subcloning and excision of cDNAs. When using vectors to produce proteins generated from the Vrs1 gene or a mutant Vrs1 gene, expression vectors are particularly useful. When an expression vector is expressed in *E. coli*, for example, it should have the above characteristics in order to be amplified in *E. coli*. Additionally, when *E. coli* such as JM109, DH5α, HB101, or XL1-Blue are used as the host, the vector must have a promoter that allows efficient expression in *E. coli*, for example, a lacZ promoter (Ward et al., Nature 341, 544-546, 1989; FASEB J. 6, 2422-2427, 1992), araB promoter (Better et al., Science 240, 1041-1043, 1988), or T7 promoter. Other examples of the vectors include pGEX-5X-1 (Pharmacia), "QIAexpress system" (QIAGEN), pEGFP, and pET.

Furthermore, the vector may comprise a signal sequence for polypeptide secretion. When producing polypeptides into the periplasm of *E. coli*, the pelB signal sequence (Lei, S. P. et al., J. Bacteriol. 169, 4379, 1987) may be used as a signal sequence for polypeptide secretion. For example, calcium chloride methods or electroporation methods may be used to introduce the vector into a host cell.

In addition to *E. coli*, expression vectors derived from mammals (e.g., pcDNA3 (Invitrogen), pEGF-BOS (Nucleic Acids Res. 18(17), 5322, 1990), pEF, and pCDM8), insect cells (e.g., "Bac-to-BAC baculovirus expression system" (GIBCO-BRL) and pBacPAK8), plants (e.g., pMH1 and pMH2), animal viruses (e.g., pHSV, pMV, and pAdexLcw), retroviruses (e.g., pZIPneo), yeasts (e.g., "*Pichia* Expression Kit" (Invitrogen), pNV11 and SP-QO1), and *Bacillus subtilis* (e.g., pPL608 and pKTH50) may also be used as vectors for producing proteins generated from the Vrs1 gene or a mutant Vrs1 gene.

For expression in animal cells such as CHO, COS, and NIH3T3 cells, the vector must have a promoter necessary for expression in such cells, for example, an SV40 promoter (Mulligan et al., Nature 277, 108, 1979), MMLV-LTR promoter, EF1α promoter (Mizushima et al., Nucleic Acids Res. 18, 5322, 1990), or CMV promoter. It is even more preferable that the vector comprises a gene for selecting transformants (for example, a drug-resistance gene enabling discrimination by a drug (such as neomycin and G418)). Examples of vectors with such characteristics include pMAM, pDR2, pBK-RSV, pBK-CMV, pOPRSV, and pOP13. Introduction of a DNA of the present invention into a cell can be carried out by a method known to one skilled in the art, for example, by an electroporation method.

Furthermore, the present invention also provides transformed barley plants introduced with the Vrs1 gene, a mutant thereof, or a DNA that suppresses the expression of the Vrs1 gene; transformed barley plants that are progenies or clones of the transformed barley plants; and breeding materials of the transformed barley plants. The present invention also provides methods for producing the transformed barley plants and their breeding materials. Transformed barley plants having the two-row phenotype as a result of introduction of the above-mentioned gene are useful, for example, in brewing beer. Transformed barley plants having the six-row phenotype are useful as feed. Furthermore, transformed barley plants having the two-row or six-row phenotype, or a phenotype intermediate between two-row and six-row types can be used, for example, in floral arrangement and the like, and thus are useful as ornamental plants. The Vrs1 gene, mutants thereof, and DNAs that suppresses the expression of the Vrs1 gene are as described above.

The DNA encoding the Vrs1 gene, a mutant thereof, or a DNA suppressing the Vrs1 gene expression can be introduced into plant cells by the above methods.

In addition, regeneration of barley is also possible using methods known to those skilled in the art (Toki et al., Plant Physiol. 100, 1503-1507, 1995). For example, several techniques for producing transformed plants are already established, and are widely used in the technical field of the present invention. These methods include the method for introducing genes into protoplasts using polyethylene glycol and then regenerating plants (Datta et al., In Gene Transfer To Plants (Potrykus, I. and Spangenberg Eds.) pp. 66-74, 1995), the method for introducing genes into protoplasts using electric pulse and then regenerating plants (Toki et al., Plant Physiol. 100, 1503-1507, 1992), the method for directly introducing genes into cells using the particle gun method and then regenerating plants (Christou et al., Bio/technology 9, 957-962, 1991), and the method for introducing genes via an *Agrobacterium*, and then regenerating plants (Hiei et al., Plant J. 6, 271-282, 1994). These methods can be appropriately used in the present invention.

When using the above *Agrobacterium* method, the method of Nagel et al. (Microbiol. Lett. 67, 325, 1990) is used, for example. In this method, a recombinant vector is transformed into an *Agrobacterium*, and subsequently the transformed *Agrobacterium* is introduced into a cell by a known method such as the leaf disk method. The above-mentioned vector comprises an expression promoter so that, for example, the Vrs1 gene of the present invention, a mutant thereof, or a DNA suppressing the Vrs1 gene expression is expressed in a plant after introduction into the plant. Generally, the Vrs1 gene of the present invention, a mutant thereof, or a DNA suppressing the Vrs1 gene expression is located downstream of the promoter, and a terminator is located further downstream of such a DNA. The recombinant vector used for this purpose is suitably selected by one skilled in the art, depending on the type of plant or method of introduction. The above-mentioned promoters include, for example, the CaMV35S derived from cauliflower mosaic virus and the ubiquitin promoter from corn (JP-A (Kokai) H02-79983).

Examples of the above-mentioned terminator can be a terminator derived from cauliflower mosaic virus and the terminator from the nopaline synthase gene; however, the promoter and terminator are not limited thereto, as long as they function in a plant.

The barley, into which the Vrs1 gene of the present invention, a mutant thereof, or a DNA suppressing the Vrs1 gene expression is introduced, may be explants, or the DNA may be introduced into the cultured cells prepared from these plants. “Barley cells” in the present invention include, for example, plant cells of a leaf, root, stem, flower (especially pollen microspores), and scutellum in an immature or mature seed; calluses; and suspension-cultured cells.

In order to efficiently select the cells transformed by introducing the Vrs1 gene of the present invention, a mutant thereof, or a DNA suppressing the Vrs1 gene expression, the above-mentioned recombinant vector preferably comprises a suitable selection marker gene or is introduced into the barley cells together with a plasmid vector comprising a selection marker gene. The selection marker genes used for this purpose include, for example, the hygromycin phosphotransferase gene resistant to the antibiotic hygromycin, the neomycin phosphotransferase resistant to kanamycin or gentamycin, and the acetyltransferase gene resistant to the herbicide phosphinothricin.

The cells into which the recombinant vector has been introduced are placed on a known selection medium containing a suitable selection agent depending on the type of introduced selection marker gene, and then cultured. In this way, the transformed plant cultured cells can be obtained.

Next, plants reproduced from the transformed cells are cultured in an acclimation medium. The acclimated, regenerated plants are then grown under usual culture conditions to obtain plants, from which seeds can be obtained once they mature and bear fruit.

The presence of the introduced foreign DNAs in the transformed plants that are regenerated and grown in this manner can be confirmed by the known PCR method or Southern hybridization method, or by analyzing the nucleotide sequences of the DNAs in plants. In this case, extraction of the DNAs from the transformed plants can be carried out according to the known method by J. Sambrook et al. (Molecular Cloning, the 2nd edition, Cold Spring Harbor Laboratory Press, 1989).

When analyzing the foreign genes which are present in the regenerated plants and include the DNAs of the present invention, using the PCR method, an amplification reaction is carried out using as a template the DNAs extracted from the regenerated plants as mentioned above. An amplification reaction can also be performed in a reaction mixture containing as primers synthesized oligonucleotides which comprise nucleotide sequences suitably selected according to the nucleotide sequences of the DNAs of the present invention or the DNAs modified according to the present invention. In the amplification reaction, denaturation, annealing, and extension reactions of DNAs can be repeated several tens of times to obtain amplified products of DNA fragments comprising the DNA sequences of the present invention. By subjecting the reaction mixture comprising the amplified products, for example, to agarose electrophoresis, the various kinds of amplified DNA fragments are fractionated, thereby enabling confirmation of whether a certain DNA fragment corresponds to a DNA of the present invention.

After obtaining a transformed plant in which the Vrs1 gene of the present invention, a mutant thereof, or a DNA suppressing the Vrs1 gene expression has been introduced into the chromosome, progenies can be obtained by sexual or asexual reproduction from the plant. Further, propagation materials (for example, seeds, fruits, panicles, tubers, tuberous roots, stocks, calluses, and protoplasts) can also be obtained from the plant or its progenies or clones, and these materials can be used to mass-produce the plants. The present invention comprises plant cells into which the Vrs1 gene, a mutant thereof, or a DNA suppressing the Vrs1 gene expression has been introduced; plants comprising the cells; progenies and clones of the plants; and propagation materials of the plants and their progenies and clones. Such plant cells, plants comprising the cells, progenies and clones of the plants, and propagation materials of the plants and their progenies and clones, can be used for altering the panicle morphology of plants (for example, barley).

The present invention also provides methods for altering the row type or panicle morphology of barley, which comprise the step of expressing the Vrs1 gene in cells of barley that is not two-rowed. The present invention also provides methods for altering the row type or panicle morphology of barley, which comprise the step of expressing a mutant Vrs1 gene in cells of two-rowed barley. The present invention further provides methods for altering the row type or panicle morphology of barley, which comprise the step of expressing a DNA that suppresses the expression of the Vrs1 gene in cells of two-rowed barley. Barley plants transformed to be two-rowed are useful, for example, in brewing beer. Barley plants transformed to be six-rowed are useful as feed. Barley plants transformed to be two-rowed or six-rowed, or of an intermediate type between two-row and six-row types can be used, for example, in floral arrangement and the like, and thus are useful as ornamental plants. The row type or panicle morphology of barley can be altered by introducing barley cells with a vector carrying in an expressible manner the Vrs1 gene, a mutant thereof, or a DNA that suppresses the expression of the Vrs1 gene, using the methods described above, and regenerating plants from the cells.

Herein, "altering" means, for example, not only altering six-rowed barley to be perfectly two-rowed (or completely altering the panicle morphology of six-rowed barley to that of two-rowed barley), but also partially altering the phenotype of six-rowed barley to that of two-rowed barley (or partially altering the panicle morphology of six-rowed barley to that of two-rowed barley). Furthermore, six-rowed barley that is altered to be two-rowed includes not only barley with the perfect six-rowed phenotype but also barley with a partial six-rowed phenotype. By exchanging the phrase "six-row type" with "two-row type", the above definition of "altering" in the methods of the present invention for altering the row type or panicle morphology is also applied to methods for altering the row type or panicle morphology of barley, which comprise the step of expressing a mutant Vrs1 gene in cells of two-rowed barley, and to methods for altering the row type or panicle morphology of barley, which comprise the step of expressing a DNA that suppresses the expression of the Vrs1 gene in cells of two-rowed barley.

It has been reported that two-rowed barley tends to be more resistant to *Fusarium* head blight as compared to six-rowed barley (K. Takeda. Selection response and parent-offspring correlation of the resistance to *Fusarium* Head Blight in barley. Japanese Journal of Breeding. 40, 91-101, 1990). Thus, the present invention provides methods for conferring barley with resistance to *Fusarium* head blight, which comprise the step of expressing the Vrs1 gene in barley cells. The resistance to *Fusarium* head blight can be conferred to barley by using the above methods to introduce into barley cells a vector carrying the Vrs1 gene in an expressible manner, and regenerating plants from the cells.

The *Fusarium* head blight affects a number of crops of the family of wheat, barley, oats, and such, and occurs predominantly in panicles. When barley is infected with *Fusarium* fungi, all or some of the panicles become brown and salmon-colored mold (conidiospores) grows at the junction of glumes during the period from the heading stage to the milk-ripe stage. When infected with *Fusarium* fungi, grains develop poorly. Multiple infections may decrease the yield by 60% to 70%. Furthermore, damaged grains may cause poisoning symptoms when used as food or feed.

Herein, "*Fusarium* fungi" refers to fungi belonging to the genus *Fusarium*. An example of the most important species is the fungus *Fusarium graminearum*. However, *Fusarium* fungi are not limited to this fungus, and all fungi of the above genus are included in *Fusarium* fungi of the present invention.

The present invention also provides proteins produced from the Vrs1 gene of the present invention or mutants thereof, methods for producing the proteins, and antibodies that bind to the proteins.

Recombinant proteins are typically prepared by inserting DNAs encoding proteins of the present invention into appropriate expression vectors, introducing the vectors into appropriate cells, culturing the transformed cells, and purifying the expressed proteins. Recombinant proteins can be expressed as fusion proteins with other proteins to make purification easier, for example, as fusion proteins with maltose-binding protein using *E. coli* as a host (New England Biolabs, USA, vector pMAL series), as fusion proteins with glutathione S-transferase (GST) (Amersham Pharmacia Biotech, vector pGEX series), or tagged with histidine (Novagen, pET series). The host cells are not particularly limited, so long as the cell is suitable for expressing the recombinant proteins. It is possible to use, for example, yeast, various plant or animal cells, insect cells or such in addition to the above-described *E. coli*. Vectors can be introduced into host cells by a variety of methods known to those skilled in the art. For example, introduction methods using calcium ions can be used for introduction into *E. coli* (Mandel, M. & Higa, A., Journal of Molecular Biology 53, 158-162, 1970; Hanahan, D., Journal of Molecular Biology 166, 557-580, 1983). Recombinant proteins expressed in the host cells can be purified and recovered from the host cells or the culture supernatant thereof by known methods in the art. When recombinant proteins are expressed as fusion proteins with the aforementioned maltose-binding protein or such, affinity purification can be carried out easily.

The obtained recombinant proteins can be used to prepare antibodies which bind to the proteins. Polyclonal antibodies can be obtained as follows, for example: Small animals such as rabbits are immunized with the Vrs1 protein (a protein produced from the Vrs1 gene), a protein produced from the mutant Vrs1 gene, or a recombinant protein expressed as a fusion protein with GST in microorganisms such as *E. coli*., or their partial peptides to obtain sera. The antibodies are prepared by purifying the sera using, for example, ammonium sulfate precipitation, a protein A or protein G column, DEAE ion exchange chromatography, or an affinity column coupled with the Vrs1 protein, a protein produced from a mutant Vrs1 gene, or a synthetic peptide. Monoclonal antibodies can be prepared as follows: Small animals such as mice are immunized with the Vrs1 protein, a protein produced from a mutant Vrs1 gene, or their partial peptide; the spleen is harvested from the mice and ground to separate cells; the cells and mouse myeloma cells are fused using a reagent such as polyethylene glycol; and from among the fused cells (hybridomas) thus obtained, clones which produce antibodies binding to the Vrs1 protein or a protein produced from a Vrs1 mutant gene are selected. Subsequently, the obtained hybridomas are transplanted into the abdominal cavity of mice, ascites are collected from the mice to prepare monoclonal antibodies, for example, by purifying using ammonium sulfate precipitation, a protein A or protein G column, DEAE ion exchange chromatography, an affinity column coupled with the Vrs1 protein, a protein produced from a mutant Vrs1 gene, or a synthetic peptide. The antibodies thus obtained can be used for purification, detection and the like of the proteins of the present invention. The present invention comprises antibodies which bind to the proteins of the present invention.

Furthermore, the present invention also provides uses of the Vrs1 gene and vectors carrying the gene. Specifically, the present invention relates to agents for enhancing the resistance of barley to *Fusarium* head blight, which comprises as an active ingredient any one of the Vrs1 gene and a vector carrying the gene. The present invention also relates to uses of the Vrs1 gene and vectors carrying the gene in producing agents for enhancing the resistance of barley to *Fusarium* head blight.

The agents of the present invention for enhancing the resistance of barley to *Fusarium* head blight may comprise, in addition to the oligonucleotides as active ingredients, for example, sterilized water, physiological saline, vegetable oil, surfactants, lipids, solubilizing agents, buffers, and preservatives, if needed.

The present invention also provides molecular markers linked to the Vrs1 gene or a mutant thereof. Herein, the "molecular marker" refers to a DNA region genetically linked to the Vrs1 gene or a mutant thereof, and is distinguishable from other DNA regions.

In general, if the map distance between a gene and its molecular marker in cM unit is shorter, the molecular marker is located closer to the gene. Such a molecular marker is highly useful because it will be inherited together with the gene. Specifically, the primer set of the present invention include markers comprising the whole or a portion of the nucleotide sequences of SEQ ID NOs: 4 to 29. Molecular markers of the present invention include STS (Sequence Tagged Site) markers, AFLP markers, RFLP markers, SNP markers, and SSR markers.

The "STS marker" refers to a DNA region which can be used to determine the presence or absence of polymorphism of a sequence-tagged site (STS) on a DNA, and the "STS" refers to a specific sequence site at a particular position of a DNA. The polymorphism of STS can be detected as the presence or absence of bands or the difference in band positions, by amplifying a DNA region comprising the specific sequence site with a nucleic acid amplification method such as the PCR method, and then subjecting the amplification products to agarose or polyacrylamide gel electrophoresis. The AFLP method refers to a method in which differences in the length of DNA fragments obtained by digestion with restriction enzymes are detected through selective amplification by PCR. "RFLP markers" refers to DNA regions that can be used to determine the presence or absence of RFLPs in chromosomal DNA sequences. "RFLPs" refers to genetic mutations (such as substitution, insertion, and deletion) that can be detected using differences in the length of DNA fragments obtained by treatment with restriction enzymes. Such mutations can be confirmed by using agarose gel electrophoresis to separate DNA fragments based on fragment length, and detecting the difference in electrophoresis mobility using Southern blotting. SSR is an abbreviation for Simple Sequence Repeats, and SSR marker is synonymous with microsatellite marker. The SSR marker is a DNA marker of DNA polymorphism based on the difference of the number of repeats in several to several hundreds of sequence repeats which are in units of two or three nucleotides in a nucleotide sequence. The nucleotide sequences in a repeating region are amplified by PCR, and the resulting amplification products are analyzed by agarose gel electrophoresis or DNA sequencer. DNA polymorphisms are detected as differences in band position or number of nucleotide sequences. Alternatively, SNP is a DNA polymorphism that occurs as a result of a single nucleotide substitution in a nucleotide sequence of DNA. A DNA marker based on this polymorphism is an SNP marker. The polymorphism can be detected by amplifying the site of single nucleotide polymorphism and the adjacent nucleotide sequences by PCR, and then analyzing the amplification products for the type of nucleotide incorporated at the site of single nucleotide polymorphism using a fluorescence-polarization analyzer.

Those skilled in the art can appropriately design optimal primers by taking into account sequence information on various molecular markers (for example, the above-described markers). Typically, the above-described primers are a primer set comprising a pair of primers designed to sandwich a barley-specific nucleotide sequence linked to the Vrs1 gene or a mutant thereof.

Specifically, primer sets of the present invention include, for example:

(a) a DNA comprising the nucleotide sequence of SEQ ID NO: 30 and a DNA comprising the nucleotide sequence of SEQ ID NO: 31 (primer set for detecting markers comprising the entire or a portion of the nucleotide sequence of SEQ ID NO: 4);

(b) a DNA comprising the nucleotide sequence of SEQ ID NO: 32 and a DNA comprising the nucleotide sequence of SEQ ID NO: 33 (primer set for detecting markers comprising the entire or a portion of the nucleotide sequence of SEQ ID NO: 5);

(c) a DNA comprising the nucleotide sequence of SEQ ID NO: 34 and a DNA comprising the nucleotide sequence of SEQ ID NO: 35 (primer set for detecting markers comprising the entire or a portion of the nucleotide sequence of SEQ ID NO: 6);

(d) a DNA comprising the nucleotide sequence of SEQ ID NO: 36 and a DNA comprising the nucleotide sequence of SEQ ID NO: 37 (primer set for detecting markers comprising the entire or a portion of the nucleotide sequence of SEQ ID NO: 7);

(e) a DNA comprising the nucleotide sequence of SEQ ID NO: 38 and a DNA comprising the nucleotide sequence of SEQ ID NO: 39 (primer set for detecting markers comprising the entire or a portion of the nucleotide sequence of SEQ ID NO: 8);

(f) a DNA comprising the nucleotide sequence of SEQ ID NO: 40 and a DNA comprising the nucleotide sequence of SEQ ID NO: 41 (primer set for detecting markers comprising the entire or a portion of the nucleotide sequence of SEQ ID NO: 9);

(g) a DNA comprising the nucleotide sequence of SEQ ID NO: 42 and a DNA comprising the nucleotide sequence of SEQ ID NO: 43 (primer set for detecting markers comprising the entire or a portion of the nucleotide sequence of SEQ ID NO: 10);

(h) a DNA comprising the nucleotide sequence of SEQ ID NO: 44 and a DNA comprising the nucleotide sequence of SEQ ID NO: 45 (primer set for detecting markers comprising the entire or a portion of the nucleotide sequence of SEQ ID NO: 11);

(i) a DNA comprising the nucleotide sequence of SEQ ID NO: 46 and a DNA comprising the nucleotide sequence of SEQ ID NO: 47 (primer set for detecting markers comprising the entire or a portion of the nucleotide sequence of SEQ ID NO: 12);

(j) a DNA comprising the nucleotide sequence of SEQ ID NO: 48 and a DNA comprising the nucleotide sequence of SEQ ID NO: 49 (primer set for detecting markers comprising the entire or a portion of the nucleotide sequence of SEQ ID NO: 13);

(k) a DNA comprising the nucleotide sequence of SEQ ID NO: 50 and a DNA comprising the nucleotide sequence of SEQ ID NO: 51 (primer set for detecting markers comprising the entire or a portion of the nucleotide sequences of SEQ ID NOs: 14 to 18);

(l) a DNA comprising the nucleotide sequence of SEQ ID NO: 52 and a DNA comprising the nucleotide sequence of SEQ ID NO: 53 (primer set for detecting markers comprising the entire or a portion of the nucleotide sequences of SEQ ID NOs: 19 to 23);

(m) a DNA comprising the nucleotide sequence of SEQ ID NO: 54 and a DNA comprising the nucleotide sequence of SEQ ID NO: 55 (primer set for detecting markers comprising the entire or a portion of the nucleotide sequences of SEQ ID NO: 24);

(n) a DNA comprising the nucleotide sequence of SEQ ID NO: 56 and a DNA comprising the nucleotide sequence of SEQ ID NO: 57 (primer set for detecting markers comprising the entire or a portion of the nucleotide sequences of SEQ ID NO: 25);

(o) a DNA comprising the nucleotide sequence of SEQ ID NO: 58 and a DNA comprising the nucleotide sequence of SEQ ID NO: 59 (primer set for detecting markers comprising the entire or a portion of the nucleotide sequences of SEQ ID NO: 26);

(p) a DNA comprising the nucleotide sequence of SEQ ID NO: 60 and a DNA comprising the nucleotide sequence of SEQ ID NO: 61 (primer set for detecting markers comprising the entire or a portion of the nucleotide sequences of SEQ ID NO: 27);

(q) a DNA comprising the nucleotide sequence of SEQ ID NO: 62 and a DNA comprising the nucleotide sequence of SEQ ID NO: 63 (primer set for detecting markers comprising the entire or a portion of the nucleotide sequences of SEQ ID NO: 28); and (r) a DNA comprising the nucleotide sequence of SEQ ID NO: 64 and a DNA comprising the nucleotide sequence of SEQ ID NO: 65 (primer set for detecting markers comprising the entire or a portion of the nucleotide sequences of SEQ ID NO: 29).

Whether the barley to be tested is two-rowed or six-rowed can be determined by comparing the information on DNA sequences amplified by these primer sets with the molecular markers of the present invention.

In addition to the above primers, those skilled in the art can prepare primer sets that have similar functions by using the nucleotide sequence of SEQ ID NO: 1 or 2, or barley-derived DNAs that hybridize under stringent conditions to a DNA comprising the nucleotide sequence of SEQ ID NO: 1 or 2. The primers of the present invention also include such primers.

One skilled in the art can produce PCR primers of the present invention using, for example, an automatic oligonucleotide synthesizer. One skilled in the art can also perform the methods of the present invention by using a known polymorphism detection method such as the below-mentioned PCR-SSCP method using the above PCR primers, or the like.

When molecular markers of the present invention are located in exons of a genomic DNA, it is also possible to utilize RT-PCR using mRNAs as a template. By using the Taqman (a quantitative PCR detection) system (Roche), the presence or absence of amplification products can be detected by fluorescence. Since this system does not need electrophoresis, it enables one to carry out the identification methods of the present invention in a short time.

The present invention also provides oligonucleotides that comprise at least 15 nucleotides, and complementary to a DNA comprising the Vrs1 gene or a mutant thereof, or a complementary strand thereof.

A “complementary strand” herein refers to one strand relative to the other strand in a double-stranded nucleic acid comprising base pairs of A:T (U for RNA) and G:C. The term “complementary” means not only that a sequence is completely complementary in a region of at least 15 consecutive nucleotides, but also that a sequence has a homology of at least 70%, preferably at least 80%, more preferably 90%, still more preferably 95% or more in the nucleotide sequence. Any algorithm known to one skilled in the art may be used for determining homology.

The oligonucleotides of the present invention can be used as probes or primers for detection and amplification of DNAs comprising the nucleotide sequence of SEQ ID NO: 1 or 2, or barley-derived DNAs that hybridize under stringent conditions to a DNA comprising the nucleotide sequence of SEQ ID NO: 1 or 2. Moreover, the oligonucleotides of the present invention can be used in the form of a DNA array substrate.

When such an oligonucleotide is used as a primer, the length is usually 15 bp to 100 bp, and preferably 17 bp to 30 bp. The primer is not particularly limited, as long as it can amplify at least a portion of a DNA of the present invention or its complementary strand. When used as a primer, its 3' side region is made to be complementary, and a restriction enzyme recognition sequence, a tag or the like can be added to its 5' side.

When the above-mentioned oligonucleotide is used as a probe, any oligonucleotide may be used without particular limitation, as long as it can specifically hybridize at least a portion of a DNA comprising the nucleotide sequence of SEQ ID NO: 1 or 2, a barley-derived DNAs that hybridize under stringent conditions to a DNA comprising the nucleotide sequence of SEQ ID NO: 1 or 2, or a complementary strand thereof. The probe may be a synthetic oligonucleotide, and usually has a length of at least 15 bp or more.

When an oligonucleotide of the present invention is used as a probe, it is preferably labeled as appropriate. Labeling methods include the following, for example: a method in which the 5' end of an oligonucleotide is phosphorylated by $^{32}P$ using T4 polynucleotide kinase; and a method (the random primed method or the like) in which substrate bases labeled with an isotope such as $^{32}P$, a fluorescent dye, or biotin are incorporated into an oligonucleotide, using a DNA polymerase such as Klenow enzyme and using random hexamer oligonucleotides and the like as a primer.

The oligonucleotides of the present invention can be produced, for example, with a commercially available oligonucleotide synthesizer. The probes can also be produced as double-stranded DNA fragments obtained by restriction enzyme treatment or the like.

Furthermore, the present invention also provides methods that determine barley is two-rowed when the molecular weight or nucleotide sequence is consistent with that of the Vrs1 gene or a two row-type mutant Vrs1 gene, wherein the methods comprise the steps of:

(a) preparing a DNA sample from barley;

(b) amplifying the region of the Vrs1 gene or a mutant Vrs1 gene from the DNA sample; and (c) comparing the molecular weight or nucleotide sequence of the amplified DNA fragment with that of the Vrs1 gene or two row-type mutant Vrs1 gene.

One skilled in the art can prepare (extract) the above-mentioned DNA samples of the present invention by known methods. Preferable preparation methods include, for example, a method for extracting DNAs using the CTAB method.

The DNA samples used in the determination methods of the present invention are not particularly limited; however, genomic DNAs extracted from a test plant, barley, are usually used. The source for the genomic DNA extraction is not particularly limited, and the DNAs can be extracted from any tissue of barley. They can be extracted, for example, from a panicle, leaf, root, stem, seed, endosperm portion, bran, or embryo.

In the present invention, then, nucleic acid amplification (for example, PCR method) is carried out using the prepared DNA as a template, and primer DNAs. The amplified DNA fragments are digested with restriction enzymes. The sizes of DNA fragments obtained by the digestion are compared between the barley to be tested and two-rowed barley by electrophoresis or such. When the molecular weights or nucleotide sequences are consistent with each other, the barley to be tested is determined to be two-rowed. The two-rowed barley includes those listed in Table 1, but is not limited thereto.

The electrophoretic analysis can be conducted using conventional methods. For example, electrophoresis is carried out by applying voltage in an agarose or polyacrylamide gel, and the pattern of fractionated DNAs is analyzed. As described above, the Vrs1 gene is not limited to DNAs comprising the nucleotide sequence of SEQ ID NO: 1 or 2 in the determination methods of the present invention. Even when a DNA comprising the nucleotide sequence of SEQ ID NO: 1 or 2 has mutations, it is included in the Vrs1 gene of the present invention as long as the gene-carrying barley has the two-row phenotype.

Furthermore, the present invention also provides methods that determine barley is six-rowed when the molecular weight or nucleotide sequence is consistent with that of a six row-type mutant Vrs1 gene, wherein the methods comprise the steps of:

(a) preparing a DNA sample from barley;
(b) amplifying the region of the Vrs1 gene or a mutant Vrs1 gene from the DNA sample; and
(c) comparing the molecular weight or nucleotide sequence of the amplified DNA fragment with that of the six row-type mutant Vrs1 gene.

Furthermore, the present invention also provides methods that determine barley is an intermediate type between the two-row and six-row types when the molecular weight or nucleotide sequence is consistent with that of an intermediate-type mutant Vrs1 gene, wherein the methods comprise the steps of:

(a) preparing a DNA sample from barley;
(b) amplifying the region of the Vrs1 gene or a mutant Vrs1 gene from the DNA sample; and
(c) comparing the molecular weight or nucleotide sequence of the amplified DNA fragment with that of the mutant Vrs1 gene which is of an intermediate type between the two-row and six-row types.

The six-row type and intermediate type between two-row and six-row types in the methods of the present invention are described above. In the methods of the present invention, the amplified DNA fragments are digested with restriction enzymes. The sizes of DNA fragments obtained by the digestion are compared between the barley to be tested and six-rowed barley by electrophoresis or such. When the molecular weights or nucleotide sequences are consistent with each other, the barley to be tested is determined to be six-rowed. Alternatively, the amplified DNA fragments are digested with restriction enzymes. The sizes of DNA fragments obtained by the digestion are compared between the barley to be tested and the intermediate-type barley between the two-row and six-row types by electrophoresis or such. When the molecular weights or nucleotide sequences are consistent with each other, the barley to be tested is determined to be of an intermediate type between the two-row and six-row types.

Furthermore, the present invention also provides methods that determine barley is two-rowed when the gel mobility of its DNA is consistent with that of the Vrs1 gene or a two row-type mutant Vrs1 gene, wherein the methods comprise the steps of:

(a) preparing a DNA sample from barley;
(b) amplifying the region of the Vrs1 gene or a mutant Vrs1 gene from the DNA sample;
(c) fractionating the amplified double-stranded DNAs on a non-denaturing gel; and
(d) comparing the mobility of the fractionated double-stranded DNAs on the gel with that of the Vrs1 gene or two row-type mutant Vrs1 gene.

Furthermore, the present invention also provides methods that determine barley is six-rowed when the gel mobility is consistent with that of a six row-type mutant Vrs1 gene, wherein the methods comprise the steps of:

(a) preparing a DNA sample from barley;
(b) amplifying the region of the Vrs1 gene or a mutant Vrs1 gene from the DNA sample;
(c) fractionating the amplified double-stranded DNAs on a non-denaturing gel; and
(d) comparing the mobility of the fractionated double-stranded DNAs on the gel with that of the six row-type mutant Vrs1 gene.

Furthermore, the present invention also provides methods that determine barley is an intermediate type between the two-row and six-row types when the gel mobility is consistent with that of a mutant Vrs1 gene which is of an intermediate type between the two-row and six-row types, wherein the methods comprise the steps of:

(a) preparing a DNA sample from barley;
(b) amplifying the region of the Vrs1 gene or a mutant Vrs1 gene from the DNA sample;
(c) fractionating the amplified double-stranded DNAs on a non-denaturing gel; and
(d) comparing the mobility of the fractionated double-stranded DNAs on the gel with that of the mutant Vrs1 gene which is of an intermediate type between the two-row and six-row types.

Furthermore, the present invention also provides methods that determine barley is two-rowed when the gel mobility of its DNA is consistent with that of the Vrs1 gene or a two row-type mutant Vrs1 gene, wherein the methods comprise the steps of:

(a) preparing a DNA sample from barley;
(b) amplifying the region of the Vrs1 gene or a mutant Vrs1 gene from the DNA sample;
(c) dissociating the amplified DNAs into single-stranded DNAs;
(d) fractionating the dissociated single-stranded DNAs on a non-denaturing gel; and
(e) comparing the mobility of the dissociated single-stranded DNAs on the gel with that of the Vrs1 gene or two row-type mutant Vrs1 gene.

Furthermore, the present invention also provides methods that determine barley is six-rowed when the gel mobility is consistent with that of a six row-type mutant Vrs1 gene wherein the methods comprise the steps of:

(a) preparing a DNA sample from barley;

(b) amplifying the region of the Vrs1 gene or a mutant Vrs1 gene from the DNA sample;

(c) dissociating the amplified DNAs into single-stranded DNAs;

(d) fractionating the dissociated single-stranded DNAs on a non-denaturing gel; and (e) comparing the mobility of the dissociated single-stranded DNAs on the gel with that of the six row-type mutant Vrs1 gene.

Furthermore, the present invention also provides methods that determine barley is an intermediate type between the two-row and six-row types when the gel mobility is consistent with that of a mutant Vrs1 gene which is of an intermediate type between the two-row and six-row types, wherein the methods comprise the steps of:

(a) preparing a DNA sample from barley;

(b) amplifying the region of the Vrs1 gene or a mutant Vrs1 gene from the DNA sample;

(c) dissociating the amplified DNAs into single-stranded DNAs;

(d) fractionating the dissociated single-stranded DNAs on a non-denaturing gel; and (e) comparing the mobility of the dissociated single-stranded DNAs on the gel with that of the mutant Vrs1 gene which is of an intermediate type between the two-row and six-row types.

The above methods include the PCR-SSCP (single-strand conformation polymorphism) method ("Cloning and polymerase chain reaction-single-strand conformation polymorphism analysis of anonymous Alu repeats on chromosome 11." Genomics 12(1), 139-146, Jan. 1 1992; "Detection of p53 gene mutations in human brain tumors by single-strand conformation polymorphism analysis of polymerase chain reaction products." Oncogene 6(8), 1313-1318, Aug. 1 1991; "Multiple fluorescence-based PCR-SSCP analysis with postlabeling." PCR Methods Appl. 4(5), 275-282, Apr. 1 1995). This method is particularly preferable for screening many DNA samples, since it has advantages such as comparative simplicity of operation and a small amount of required test sample. The principle of the method is as follows. A single-stranded DNA dissociated from a double-stranded DNA fragment forms a unique higher conformation, depending on the respective nucleotide sequence. After electrophoresis on a polyacrylamide gel without a denaturant, complementary single-stranded DNAs having the same chain length shift to different positions in accordance with the difference of the respective higher conformations. The conformation of a single-stranded DNA changes even by a substitution of one base, which results in a different mobility on polyacrylamide gel electrophoresis. Accordingly, the presence of a mutation in a DNA fragment due to a point mutation, deletion, insertion and such can be detected by detecting the change in mobility.

More specifically, a region comprising a target site of the Vrs1 gene or a mutant Vrs1 gene is first amplified by the PCR method or the like. Preferably, a region to be amplified is about 100 bp to 600 bp in length. In amplifying gene fragments by PCR, DNA fragments to be synthesized can be labeled by using primers labeled with an isotope such as $^{32}P$, a fluorescent dye, biotin and so on, or by adding substrate nucleotides labeled with an isotope such as $^{32}P$, a fluorescent dye, biotin and so on, to the PCR reaction solution. Alternatively, the synthesized DNA fragments can be labeled after the PCR reaction by adding substrate nucleotides labeled with an isotope such as $^{32}P$, a fluorescent dye, biotin and so on using the Klenow enzyme and such. The DNA fragments thus obtained are electrophoresed in the form of a double strand on a polyacrylamide gel without a denaturant such as urea. Alternatively, such DNA fragments may be denatured by heating and the like, and then subjected to electrophoresis on a polyacrylamide gel without a denaturant such as urea. The conditions for separating DNA fragments can be ameliorated by adding appropriate amounts (about 5% to 10%) of glycerol to the polyacrylamide gel. Further, although the electrophoresis conditions vary depending on the properties of respective DNA fragments, it is usually carried out at room temperature (20° C. to 25° C.). When a preferable separation cannot be achieved, a temperature to achieve the optimal mobility is selected from temperatures between 4° C. and 30° C. After the electrophoresis, the mobility of the DNA fragments is detected by autoradiography using X-ray films, a scanner for detecting fluorescence and the like, to analyze the result. When bands with different mobility are detected, the presence of a mutation can be confirmed by directly excising the bands from the gel, amplifying them again by PCR, and directly sequencing the amplified fragments. Even when labeled DNAs are not used, the bands can also be detected by staining the gel after electrophoresis with ethidium bromide, silver and such.

The present invention further provides methods that determine barley is two-rowed when the sizes of the detected DNA fragments are consistent with those of the Vrs1 gene or a two row-type mutant Vrs1 gene, wherein the methods comprise the steps of:

(a) preparing a DNA sample from barley;

(b) amplifying the region of the Vrs1 gene or a mutant Vrs1 gene from the DNA sample;

(c) digesting the prepared DNA sample with restriction enzymes;

(d) fractionating the DNA fragments according to their sizes; and (e) comparing the sizes of the detected DNA fragments with those of the Vrs1 gene or two row-type mutant Vrs1 gene.

Furthermore, the present invention also provides methods that determine barley is six-rowed when the sizes of the detected DNA fragments are consistent with those of a six row-type mutant Vrs1 gene, wherein the methods comprise the steps of:

(a) preparing a DNA sample from barley;

(b) amplifying the region of the Vrs1 gene or a mutant Vrs1 gene from the DNA sample;

(c) digesting the prepared DNA sample with restriction enzymes;

(d) fractionating the DNA fragments according to their sizes; and (e) comparing the sizes of the detected DNA fragments with those of the six row-type mutant Vrs1 gene.

Furthermore, the present invention also provides methods that determine barley is of an intermediate type between the two-row and six-row types when the sizes of the detected DNA fragments are consistent with those of a mutant Vrs1 gene which is of an intermediate type between the two-row and six-row types, wherein the methods comprise the steps of:

(a) preparing a DNA sample from barley;

(b) amplifying the region of the Vrs1 gene or a mutant Vrs1 gene from the DNA sample;

(c) digesting the prepared DNA sample with restriction enzymes;

(d) fractionating the DNA fragments according to their sizes; and (e) comparing the sizes of the detected DNA fragments with those of the mutant Vrs1 gene which is of an intermediate type between the two-row and six-row types.

The above methods include the RFLP method using Restriction Fragment Length Polymorphism (RFLP) and the PCR-RFLP method. Restriction enzymes are generally used as enzymes to cleave DNAs. Specifically, when a nucleotide addition or deletion exists in the recognition site of a restriction enzyme, or when a nucleotide insertion or deletion exists in a DNA fragment generated by a restriction enzyme treatment, the sizes of the fragments generated after the restriction enzyme treatment differ among the Vrs1 gene, two row-type mutant Vrs1 genes, six row-type mutant Vrs1 genes, and mutant Vrs1 genes which are of an intermediate type between the two-row and six-row types. The portion comprising such a mutation site is amplified by the PCR method, and then treated with each restriction enzyme to detect the polymorphic site as a difference in the mobility of bands by electrophoresis. Alternatively, a polymorphic site can be detected by treating chromosomal DNAs with such a restriction enzyme, subjecting the fragments to electrophoresis, and then carrying out Southern blotting with a probe DNA. The restriction enzymes to be used can be appropriately selected in accordance with respective mutation sites. In this method, Southern blotting can be performed not only on genomic DNAs but also on cDNAs which are synthesized by a reverse transcriptase from RNAs prepared from the barley to be tested and then directly cleaved with restriction enzymes. Alternatively, a part or whole of the Vrs1 gene or a mutant Vrs1 gene can be amplified by PCR using such cDNAs as a template, and cleaved with restriction enzymes, and then the difference in mobility can be examined.

The present invention provides methods that determine barley is two-rowed when the gel mobility of its DNA is consistent with that of the Vrs1 gene or a two row-type mutant Vrs1 gene, wherein the methods comprise the steps of:

(a) preparing a DNA sample from barley;

(b) amplifying the region of the Vrs1 gene or a mutant Vrs1 gene from the DNA sample;

(c) fractionating the amplified DNAs on a gel with a gradually increasing concentration of a DNA denaturant; and (d) comparing the mobility of the fractionated DNAs on the gel with that of the Vrs1 gene or two row-type mutant Vrs1 gene.

The present invention provides methods that determine barley is six-rowed when the gel mobility is consistent with that of a six row-type mutant Vrs1 gene, wherein the methods comprise the steps of:

(a) preparing a DNA sample from barley;

(b) amplifying the region of the Vrs1 gene or a mutant Vrs1 gene from the DNA sample;

(c) fractionating the amplified DNAs on a gel with a gradually increasing concentration of a DNA denaturant; and (d) comparing the mobility of the fractionated DNAs on the gel with that of the six row-type mutant Vrs1 gene.

The present invention provides methods that determine barley is an intermediate type between the two-row and six-row types when the gel mobility is consistent with that of a mutant Vrs1 gene which is of an intermediate type between the two-row and six-row types, wherein the methods comprise the steps of:

(a) preparing a DNA sample from barley;

(b) amplifying the region of the Vrs1 gene or a mutant Vrs1 gene from the DNA sample;

(c) fractionating the amplified DNAs on a gel with a gradually increasing concentration of a DNA denaturant; and (d) comparing the mobility of the fractionated DNAs on the gel with that of the mutant Vrs1 gene which is of an intermediate type between the two-row and six-row types.

The denaturant gradient gel electrophoresis method (DGGE method) can be exemplified as one of such methods. A region comprising a target site of the Vrs1 gene, a two row-type mutant Vrs1 gene, a six row-type mutant Vrs1 gene, or a mutant Vrs1 gene which is of an intermediate type between the two-row and six-row types is amplified by the PCR method and the like using primers of the present invention and such; the resulting products are electrophoresed on a polyacrylamide gel with a gradually increasing concentration of a denaturant such as urea; and the result is compared with that of a healthy subject. A polymorphism can be identified by detecting the difference in mobility of the DNA fragments, since the mobility rate of fragments with mutations decreases drastically as the DNA fragments become single-stranded DNAs at lower denaturant concentration points.

In addition to the above-mentioned methods, the Allele Specific Oligonucleotide (ASO) hybridization method can be used. An oligonucleotide comprising a nucleotide sequence where a polymorphism is predicted to exist, is prepared, and is subjected to hybridization with a DNA sample. When a polymorphic nucleotide different from the oligonucleotide exists in the sample DNA used for hybridization, the efficiency of hybridization is reduced. The reduction of the hybridization efficiency can be detected by the Southern blotting method; methods which utilize specific fluorescent reagents that have a characteristic to quench by intercalation into a gap of a hybrid; and the like.

Furthermore, the detection may be conducted by the ribonuclease A mismatch truncation method. Specifically, a region comprising a target site of the Vrs1 gene, a two row-type mutant Vrs1 gene, a six row-type mutant Vrs1 gene, or a mutant Vrs1 gene which is of an intermediate type between the two-row and six-row types is amplified by the PCR method and the like, and the amplified products are hybridized with labeled RNAs which are prepared from healthy-type cDNAs and such incorporated into a plasmid vector and the like. Since the hybrid forms a single strand conformation in a portion comprising a nucleotide different from the healthy-type, a polymorphism can be detected by cleaving this portion with ribonuclease A and then performing autoradiography and the like.

Barley of the two-row, six-row type, or an intermediate type between the two-row and six-row types can be selected at early stages by using the determination methods of the present invention. Specifically, the present invention also provides methods for selecting two-rowed barley, which comprise the steps of:

(a) producing a variety by crossing two-rowed barley with barley that is not two-rowed or whose row type is unknown; and (b) determining whether the barley produced in step (a) is two-rowed by the methods described herein.

Furthermore, the present invention also provides methods for selecting six-rowed barley, which comprise the steps of:

(a) producing a variety by crossing six-rowed barley with barley that is not six-rowed or whose row type is unknown; and (b) determining whether the barley produced in step (a) is six-rowed, using the methods described herein.

Furthermore, the present invention also provides methods for selecting barley of an intermediate type between the two-row and six-row types, which comprise the steps of:

(a) producing a variety by crossing barley of an intermediate type between the two-row and six-row types with barley that is not of an intermediate type between the two-row and six-row types or whose row type is unknown; and
(b) determining whether the barley produced in step (a) is of an intermediate type between the two-row and six-row types.

The two-row, six-row, and intermediate types in the selection methods are as described above. Meanwhile, "being not two-rowed" means being six-rowed or being of an intermediate type; "being not six-rowed" means being two-rowed or being of an intermediate type; and "being not of an intermediate type" means being two-rowed or six-rowed.

As described above, the present invention provides methods for selecting barley identified as being two-rowed, six-rowed, or of an intermediate type between the two-row and six-row types at an early stage. Herein, "early stage" refers to the state before heading of barley, preferably the state immediately after germination. Since double fertilization may occur in barley, genotyping can be carried out using DNAs extracted from portions excised from endosperms before seeding. Whether the barley is two-rowed, six-rowed, or of an intermediate type between the two-row and six-row types can be determined by the methods described above. Use of the selection methods of the present invention enables one to breed varieties with the two-row or six-row phenotype, or a phenotype intermediate between two-row and six-row types in a shorter period than before.

The present invention also relates to methods of screening for a test compound.

The first embodiment of the screening methods of the present invention includes methods of screening for a test compound, which comprise the steps of:
(a) contacting a test compound with the transcript of the Vrs1 gene or a mutant Vrs1 gene;
(b) detecting the binding between a test compound and the transcript of the Vrs1 gene or mutant Vrs1 gene; and
(c) selecting a test compound that binds to the transcript of the Vrs1 gene or mutant Vrs1 gene.

In the first embodiment, first, a test compound is contacted with the transcript of the Vrs1 gene or a mutant Vrs1 gene. The "transcript of the Vrs1 gene or a mutant Vrs1 gene" in the screening methods of the present invention includes not only the transcript of the Vrs1 gene or a mutant Vrs1 gene but also translation products resulting from translation of the transcript. The mutant Vrs1 gene includes two row-type mutant Vrs1 genes, six row-type mutant Vrs1 genes, and mutant Vrs1 genes of an intermediate type between the two-row and six-row types.

The "test compound" in the methods of the present invention is not particularly limited, and includes, for example, single compounds such as natural compounds, organic compounds, inorganic compounds, proteins, and peptides; as well as compound libraries, expression products of gene libraries, cell extracts, cell culture supernatants, products of fermentation microorganisms, marine organism extracts, plant extracts, prokaryotic cell extracts, unicellular eukaryote extracts, and animal cell extracts. If needed, the above test compounds can be appropriately labeled before use. Labels include, for example, radiolabels and fluorescent labels.

In the present invention, "contacting" is carried out as follows. For example, when the transcript of the Vrs1 gene or a mutant thereof is in a purified state, the contact can be achieved by adding a test compound to the purified sample. Alternatively, when the transcript is expressed in cells or a cell extract, the contact can be achieved by adding a test compound to the cell culture or to the cell extract. The cells in the present invention are not particularly limited, but cells derived from plants including barley are preferable. When the test compounds are proteins, the contact can also be achieved, for example, by introducing vectors carrying DNAs encoding the proteins into cells expressing the Vrs1 gene or a mutant thereof, or by adding the vectors to a cell extract in which the Vrs1 gene or a mutant thereof is expressed. Alternatively, for example, two-hybrid methods using yeast, animal cells, or the like can also be used.

In the first embodiment, the binding between the test compound and the transcript of the Vrs1 gene or a mutant thereof is subsequently detected. Detection or measurement of the binding between proteins can be carried out by using, for example, labels attached to the proteins. The types of labels include, fluorescent labels and radiolabels, for example. The binding can also be measured by known methods such as the yeast two hybrid methods and the methods using BIACORE. In the present methods, the test compound bound to the transcript of the Vrs1 gene or a mutant thereof are then selected. The selected test compounds include compounds that alter the panicle morphology of barley. For example, test compounds that bind to the transcript of the Vrs1 gene or a two row-type mutant Vrs1 gene are thought to be useful in altering the row type or panicle morphology of two-rowed barley. Alternatively, test compounds that bind to the transcript of a mutant Vrs1 gene which is of the six-row type or of an intermediate type between the two-row and six-row types are thought to be useful for altering the panicle morphology of barley that is six-rowed or of an intermediate type between the two-row and six-row types, and enhancing its resistance to *Fusarium* head blight. Since barley in which the row type or panicle morphology has been altered can be used, for example, in floral arrangement, it is useful in the field of ornamental plants. Alternatively, the selected test compounds may also be used as test compounds in the screening described below.

Furthermore, the second embodiment of the screening methods of the present invention provides methods of screening for a test compound, which comprise the steps of:
(a) contacting a test compound with cells collected from barley;
(b) determining the expression level of a transcript of the Vrs1 gene or a mutant Vrs1 gene; and
(c) selecting a test compound that alters the expression level of the transcript as compared to when the test compound is not contacted with the cells.

In the second embodiment, a test compound is first contacted with cells collected from barley. Herein, the "cells collected from barley" are any barley cells that undoubtedly comprise the Vrs1 gene or a mutant thereof. The "test compound" and "contacting" are as described above.

In the second embodiment, the expression level of transcript of the Vrs1 gene or a mutant thereof is subsequently measured. The expression level of transcript of the Vrs1 gene or a mutant thereof can be measured by methods known to one skilled in the art. For example, mRNA encoding a transcript of the Vrs1 gene or a mutant thereof is extracted according to a conventional method, and the transcription level of the gene can be measured by performing the Northern hybridization method or the RT-PCR method using this mRNA as a template. Further, the expression level of transcript of the Vrs1 gene or a mutant thereof can be measured using DNA array techniques.

The translation level of the gene can also be measured by collecting fractions comprising transcripts of the Vrs1 gene or a mutant thereof in accordance with a standard method, and detecting its expression by electrophoresis such as SDS- PAGE. The translation level of the gene can also be measured by performing the Western blotting method using an antibody against transcripts of the Vrs1 gene or a mutant thereof to detect its expression.

Antibodies used for detecting transcripts of the Vrs1 gene or mutant Vrs1 genes are not particularly limited, as long as they allow the detection. For example, both monoclonal and polyclonal antibodies can be used. Such antibodies can be prepared by methods known to those skilled in the art, as described above.

In the second embodiment, then, test compounds are selected as compounds that alter the panicle morphology of barley when the expression level of transcript of the Vrs1 gene or a mutant Vrs1 gene alters as compared to when the test compounds are not contacted. Specifically, when the test compounds increase the expression level of the Vrs1 gene or a two row-type mutant Vrs1 gene, the test compounds are expected to be useful for stronger suppression of the development of lateral spikelets. Alternatively, when the compounds reduce the expression level of the Vrs1 gene or a two-row type mutant Vrs1 gene, the test compounds are expected to be useful for stronger enhancement of the development of lateral spikelets. Since barley with altered row type or panicle morphology can be used, for example, in floral arrangement, it is useful in the field of ornamental plants.

The third embodiment of the screening methods of the present invention provides methods of screening for a test compound, which comprise the steps of:

(a) providing cells or a cell extract comprising DNAs in which a reporter gene is operably linked downstream of the promoter region of the Vrs1 gene or a mutant Vrs1 gene;
(b) contacting a test compound with the cells or cell extract;
(c) determining the expression level of the reporter gene in the cells or cell extract; and
(d) selecting a test compound that alters the expression level of the reporter gene as compared to when the test compound is not contacted.

In the third embodiment, cells or cell extracts comprising DNAs in which a reporter gene is operably linked downstream of the promoter region of the Vrs1 gene or a mutant Vrs1 gene, are first provided.

In the third embodiment, "operably linked" means that the reporter gene is linked to the promoter region of the Vrs1 gene or a mutant Vrs1 gene so that the expression of the reporter gene is induced by binding of transcription factors to the promoter region of the Vrs1 gene or the mutant Vrs1 gene. Accordingly, the meaning "operably linked" also includes cases where the expression of a fusion protein is induced by binding of transcription factors to the region of the Vrs1 gene or a mutant Vrs1 gene, even when the reporter gene is linked to another gene and thus forms a fusion protein with the gene product.

The reporter gene is not particularly limited, so long as its expression can be detected. For example, reporter genes generally used by those skilled in the art include the CAT gene, lacZ gene, luciferase gene, β-glucuronidase gene (GUS), and GFP gene.

In the third embodiment, the above-mentioned cells or cell extracts are subsequently contacted with the test compound. Then, the expression level of the reporter gene in the cells or the cell extracts is measured. The terms "test compound" and "contacting" refer to the same as mentioned above.

The expression level of the reporter gene can be determined using methods known to those skilled in the art, according to the type of reporter gene. For example, when using the CAT gene as the reporter gene, the CAT gene expression level can be determined by measuring the acetylation of chloramphenicol, caused by the CAT gene product. When the lacZ gene is used as the reporter gene, its expression level can be determined by analyzing the coloring of a dye compound due to the catalytic action of the gene expression product. The expression level of the luciferase gene as a reporter can be determined by measuring the fluorescence of a fluorescent compound, caused by the catalytic action of the luciferase gene expression product. The expression level of the β-glucuronidase (GUS) gene can be determined by analyzing the coloring of 5-bromo-4-chloro-3-indolyl-β-glucuronide (X-Gluc) or the luminescence of Glucuron (ICN), caused by the catalytic action of the GUS gene expression product. The expression level of the GFP gene can be determined by measuring fluorescence due to the GFP protein.

In the third embodiment, test compounds that alter the expression level of the reporter gene, as compared to when the test compounds are not contacted, are selected. Specifically, when the test compounds increase the expression level of the reporter gene linked downstream of the promoter region of the Vrs1 gene or a two row-type Vrs1 gene, they are expected to be useful for stronger suppression of the development of lateral spikelets. Alternatively, when the test compounds reduce the expression level of the reporter gene linked downstream of the promoter region of the Vrs1 gene or a two row-type Vrs1 gene, they are expected to be useful for stronger enhancement of the development of lateral spikelets. Since barley with altered row type or panicle morphology can be used, for example, in floral arrangement, it is useful in the field of ornamental plants.

The present invention also provides methods for determining whether a test genomic fragment has a target sequence in a protein encoded by the Vrs1 gene or a mutant Vrs1 gene, in which an arbitrary test genomic fragment is determined to have a target sequence in a protein encoded by the Vrs1 gene or a mutant Vrs1 gene when the protein encoded by the Vrs1 gene or mutant Vrs1 gene allows expression of a reporter gene operably linked to the arbitrary test genomic fragment, wherein the methods comprise the steps of:

(a) contacting a protein encoded by the Vrs1 gene or a mutant Vrs1 gene with a DNA comprising a reporter gene operably linked to an arbitrary genomic fragment in cells or a cell extract; and
(b) determining whether the reporter gene is expressed.

In the methods of the present invention for screening genomic fragments, first, a protein encoded by the Vrs1 gene or a mutant Vrs1 gene is contacted with a DNA comprising a reporter gene operably linked to an arbitrary genomic fragment in cells or a cell extract. Herein, "operably linked" is as described above. The nucleotide sequence and length of the genomic fragments are not limited. Herein, when the transcript of the Vrs1 gene or a mutant Vrs1 gene is in a purified state, the "contact" can be achieved, for example, by mixing the purified sample with a DNA comprising a reporter gene operably linked to an arbitrary genomic fragment in a cell extract. Alternatively, when the transcript of the Vrs1 gene or a mutant Vrs1 gene is expressed in cells or contained in a cell extract, the "contact" can be achieved by mixing it with a DNA comprising a reporter gene operably linked to an arbitrary genomic fragment. Herein, the DNA comprising a reporter gene operably linked to an arbitrary genomic fragment may be carried by a vector in an expressible manner.

In these methods, whether the reporter is expressed is then determined. Expression of the reporter gene can also be assayed by the methods described above, according to the type of reporter gene.

In these methods, when the protein encoded by the Vrs1 gene or a mutant Vrs1 gene allows expression of the reporter gene operably linked to an arbitrary genomic fragment is expressed, the arbitrary genomic fragment is determined to have a target sequence (which includes, but is not limited to, promoter sequence and enhancer sequence) in a protein encoded by the Vrs1 gene or mutant Vrs1 gene.

Furthermore, the present invention also provides methods for determining whether a test genomic fragment comprises a gene that is regulated by a protein encoded by the Vrs1 gene or a mutant Vrs1 gene, in which an arbitrary test genomic fragment is determined to comprise a gene that is regulated by the protein encoded by the Vrs1 gene or mutant Vrs1 gene when the protein encoded by the Vrs1 gene or mutant Vrs1 gene allows expression of the gene comprised in the arbitrary test genomic fragment, wherein the methods comprise the steps of:

(a) contacting the protein encoded by the Vrs1 gene or a mutant Vrs1 gene with a DNA comprising an arbitrary genomic fragment in cells or a cell extract; and (b) determining whether a gene comprised in the arbitrary genomic fragment is expressed.

In the gene screening methods of the present invention, first, a protein encoded by the Vrs1 gene or a mutant Vrs1 gene is contacted with a DNA comprising an arbitrary genomic fragment in cells or a cell extract. Herein, "contacting" is as described above.

In the gene screening methods of the present invention, whether a gene comprised in an arbitrary genomic fragment is expressed is then determined. The expression can appropriately assayed by the methods described above. An expressed gene comprised in the genomic fragment is regulated by a protein encoded by the Vrs1 gene or a mutant Vrs1 gene.

The present invention also relates to kits for use in the screening methods described above. Such kits can comprise materials to be used in the detection and assay steps in the screening methods described above. For example, such materials include the Vrs1 gene or a mutant thereof, and probes, primers, antibodies, staining solutions, and the like, which are necessary for determining the expression levels of arbitrary genomic fragments. In addition, distilled water, salts, buffers, protein stabilizers, preservatives, and the like may be contained in the kits.

All prior art documents cited herein are incorporated herein by reference.

EXAMPLES

Hereinafter, the present invention will be specifically described with reference to Examples, but it is not construed as being limited thereto.

Example 1

Creation of Linkage Map of the Row-Type Gene Vrs1

An F2 population consisting of 464 plants was produced by crossing the two-rowed barley variety "DebreZeit29" with the six-rowed mutant "New GoldenM13", and a linkage map was created based on it. Then, another F2 population consisting of 1,106 plants was produced by crossing the two-rowed barley variety "Golden Promise" with the six-rowed barley variety "Azumamugi", and another linkage map was created based on it (Komatsuda, T., Tanno, K., Comparative high resolution map of the six-rowed spike locus 1 (vrs1) in several populations of barley, *Hordeum vulgare* L. Hereditas 141, 68-73, 2004). Furthermore, another F2 population consisting of 1,781 plants, which was produced by crossing the two-rowed barley variety "Golden Promise" with the six-rowed barley variety "Azumamugi", was also used in the analysis to create a highly precise linkage map.

Example 2

Preparation of Aligned BAC 2.1 Materials and Methods 2.1.1 PCR screening of BAC library PCR screening was carried out using DNAs in a BAC library prepared using the barley variety Morex. The screening began with a total of eight hundred and sixteen 384-well plates (containing 313,344 BAC clones). First, cells cultured in each plate were collected and combined together. Pooled BAC DNAs were prepared by extraction using a standard alkaline lysis method. Then, a total of 82 super-pool DNAs were prepared, each of which was obtained by combining pooled DNAs from ten plates.

As a first step, the superpool DNAs were screened using PCR markers linked to the gene of interest. Specifically, only ten pooled DNAs corresponding to each of the super-pool DNAs with which DNAs as PCR markers had been amplified were screened. The screening was carried out by PCR directly using as templates the respective *E. coli* clones of 384-well plates which correspond to the pooled DNAs with which DNAs as PCR markers had been amplified. The *E. coli* clones whose DNAs as PCR markers had been found to be amplified were cultured at 37° C. in LB medium containing 12.5 μg/ml chloramphenicol.

PCR mixture (10 μl) contained 0.25 units of ExTaq polymerase (Takara, Tokyo, Japan), 0.3 μM of each primer, 200 μM of each dNTPs, 1 to 4 mM $MgCl_2$, and 1×PCR buffer (Takara 1×: 25 mM TAPS (pH 9.3, 25° C.), 50 mM KCl, and 1 mM 2-mercaptoethanol). The PCR condition was as follows: pre-heating at 94° C. for three minutes, followed by 30 cycles of denaturation at 94° C. for 30 seconds; annealing for 30 seconds at a temperature of 50° C. to 68.5° C. (the temperature depended on the type of marker); and extension at 72° C. for 0.5 to 2 minutes (the period depended on the type of marker); and the final incubation at 72° C. for seven minutes. The amplified DNAs were fractionated on a 1% to 1.5% agarose gel (Agarose ME; Iwai Kagaku, Tokyo, Japan) in 0.5×TBE buffer (1×TBE: 89 mM Tris-borate, 2 mM EDTA (pH 8.0)) and stained with ethidium bromide for observation.

2.1.2 Contig Alignment

Multiple BAC DNAs selected with a single PCR marker were aligned by fingerprinting, which involved HindIII digestion of the DNAs and electrophoresis on a 1% agarose gel. To verify the alignment, the presence of amplified DNAs was confirmed using PCR markers prepared based on the nucleotide sequence of BAC. The PCR markers used were previously mapped on chromosome 2 using a barley-wheat chromosome addition line and high-density linkage map analysis.

2.2 Results and Discussion

Barley chromosome walking was carried out to prepare a BAC alignment covering the row-type gene region. The chromosome walking was initiated simultaneously from both PCR markers, AFLP1 and AFLP2. AFLP2 does not undergo recombination with the row-type gene vrs1, while AFLP1 is a marker for only single-plant vrs1 recombination. With AFLP1, the BAC clone M102J11 (hereinafter IDs are indicated in the same way) was isolated. Hereinafter, even when multiple BAC clones have been obtained by screening with a single PCR marker, only the minimal numbers of BAC clones required for the BAC alignment are described. With AFLP2, M111L1 and M351N10 were isolated. An STS marker (351N10-T7) was prepared by determining the T7-terminal nucleotide sequence of BAC M351N10. PCR amplification was also carried out using DNAs of other BAC clones. Amplification was commonly observed in M102J1 and M111L15, demonstrating that they partially overlap with each other. At the same time, comparison with the linkage map revealed that M102J 11 was located towards the centromere side while M111L15 was located towards the distal side of the chromosome. Thus, vrs1 was found to initiate at M102J11 at the distal side. Then, chromosome walking was continued from M111L15 towards the chromosomal end.

M669N11 was isolated by PCR screening using a HindIII fragment of M111 L15 (111 L15-f1-F) as an STS marker. M045M08 and M572D24 were isolated by PCR screening using an STS marker prepared based on the T7-terminal nucleotide sequence of M669N11 (M669N11-T7). M185K11 was isolated by PCR screening using a HindIII fragment of M572D24 (M572D24-fC-R) as an STS marker. The full-length DNA nucleotide sequence of M185K11 was determined, and an STS marker was prepared based on the sequence (E18). M053F18 was isolated by PCR screening using the marker. An STS marker was prepared based on the T7-terminal nucleotide sequence of MO53F8 (M053F18-T7). This marker underwent recombination with vrs1 in six plants and was mapped towards the distal side on the chromosome, opposite to AFLP1. These findings suggested that the row-type gene vrs1 is presentinany one of M102J11, M111L15, M045M08, M185K11, and M053F18. The length of contig formed by the five BAC clones was estimated to be 453 kb. In this contig, the distance between AFLP1 and E18 was 353 kb and only one plant was observed to undergo recombination in this region. By contrast, six plants were observed to undergo recombination between E18 and M053F18-T7, although the distance was only 86 kb. This suggested that the recombination frequency was not uniform. Specifically, it was suggested that the row-type gene vrs1 was likely to be linked to markers located between AFLP1 and M053F18-T7 (FIG. 3).

Example 3

Nucleotide Sequence Analysis of BAC Contig 3.1 Materials and Methods 3.1.1 Determination of BAC nucleotide sequence BAC DNAs were extracted from each BAC clone using the QIAGEN Large-Construct kit (QIAGEN GmbH; Hilden, Germany). The DNAs were fragmented at random by sonication and size-fractionated by electrophoresis. The DNAs were ligated to a pUC18 vector. Cells of the *E. coli* strain DH10B were transformed with the plasmids to prepare two types of shotgun libraries with their average insert size being 2 kb and 5 kb. One thousand clones in each library were sequenced at both ends by the Dye-terminator method using a capillary sequencer. After base calling, a total of 4,000 shotgun sequences were assembled using the Phred/phrap program (available on the internet at www.phrap.org/phred-phrapconsed.html). The assembled nucleotide sequences were aligned in order using the nucleotide sequence of the cloning site in BAC and both of the terminal nucleotide sequences of bridge clones. Gaps were filled by full nucleotide sequencing of the bridge clones using primer walking or transposon-mediated sequencing.

3.1.2Nucleotide Sequence Analysis

The obtained DNA nucleotide sequences were analyzed using “GrainGenes Blast against Triticeae repeat database” (available on the internet at wheat.pw.usda.gov/GG2/blast-.shtml). After removing regions of repetitive sequences, the DNA nucleotide sequences were analyzed using “TIGR plant repeat and checked against Grameneae repeat database” (available on the internet at tigrblast.tigr.org/euk-blast/index.cgi?project=plant.repeats). Regions that do not contain known repetitive sequences in the above sequence analyses were analyzed using NCBI nucleotide-nucleotide blast (blastn) against the EST database (available on the internet at www.ncbi.nlm.nih.gov/blast/).

Meanwhile, the obtained 406-kb DNA was analyzed by RiceGAAS (available on the internet at ricegaas.dna.affrc.go.jp/) and GeneMark.hmm (available on the internet at opal.biology.gatech.edu/GeneMark/eukhmm.cgi) to predict genes within its nucleotide sequence. In RiceGAAS, a BLASTX search is simultaneously performed with gene predictions that use multiple programs such as GENSCAN, RiceHMM, and MZEF. ORFs of some eukaryotes including barley can be predicted by using GeneMark.hmm. The amino acid sequences of the predicted proteins were searched for homology using Blastp.

3.2 Results and Discussion 3.2.1 Determination of BAC Nucleotide Sequences

A 406,323-bp virtual genome contig was obtained from four BAC clones (M102J11, M111L15, M045M08, and M185K11) by removing overlapping regions from their whole nucleotide sequences. The small gap of 102J11 was not filled, because the marker analysis described below revealed that vrs1 was located not in this gap but within the 406,323-bp virtual genome contig. Within the overlapping regions, there were only five portions that showed inconsistency in the nucleotide sequences between two clones. Specifically, the five portions are: three single-nucleotide substitutions, one insertion/deletion (29 bases), and a difference in the number of repeats in a TA repetitive sequence. There was no such inconsistency in the candidate region for the vrs1 gene described below.

3.2.2 Identification of Vrs1 Gene Candidate

A Blastn analysis revealed that the 406,323-bp sequence exhibited similarity to the nucleotide sequences of 19 cereal ESTs. Of these, four ESTs were found to be repetitive within the 406,323-bp sequence. Of the remaining 15 ESTs, twelve were revealed to be repetitive sequences by barley-wheat chromosome addition line analysis. The remaining three ESTs (E18, E30, and E42) were unique sequences and thus used as genetic markers. Specifically, 44 genes were predicted by searches for E18, E30, and E42 using GeneMark.hmm. Of these, most were highly repetitive genomic sequences, and only a homeobox gene (which was temporarily named by the present inventors) was suggested to be clearly involved in morphogenesis (the gene is located within the region of positions 164217 to 165109).

Example 4

Mutant Analysis 4.1 Materials and Methods 4.1.1 Mutant Lines of Two-Rowed Varieties Forty-one lines of hexastichon (hex-v) mutants and 16 lines of Intermedium spike-d (Int-d) mutants induced from the two-rowed varieties, “Bonus”, “Foma”, and “Kristina” were used. The hex-v mutants have well-developed lateral spikelets and extended awns in their panicles, and thus their morphologies are very similar to panicles of normal six-rowed varieties. In the Int-d mutants, the degree of development of lateral spikelets in panicles is intermediate between those of the two-row and six-row types, and the awn length varies among the mutant lines and is also influenced by the environment. Both hex-v and Int-d are alleles of vrs1.

4.1.2 Searching for Lines Having a Deletion in the Region of a Gene Governing the Row Type by Marker Analysis of Mutant Lines Genomic DNAs were extracted from original varieties and their mutants by the SDS method. PCR analysis was carried out using 16 types of molecular markers closely linked to the vrs1 gene to find deletions of the row type-governing gene.

4.1.3 Analysis of Mutations in the DNA Nucleotide Sequence of the Row Type-Governing Gene in Mutant Lines The gene governing the row type was amplified from genomic DNAs of original varieties and the mutants using the oligonucleotide primers: M111L15F84204 (5'-GAAAGATGATTGCCAACTACC-3') (SEQ ID NO: 66) and Ml L15R86329 (5'-GTCATAACTCGGCAAACATAG-3') (SEQ ID NO: 67). The nucleotide sequences of plus and minus strands of the amplified fragments were determined using an ABI3130 automated DNA sequencer and the following oligonucleotide primers:

```
M111L15F84204
(5'- GAAAGATGATTGCCAACTACC -3');    (SEQ ID NO: 68)

M111L15R84648
(5'- ATAGGGCTTCAAGATCGGCAG -3');    (SEQ ID NO: 69)

M111L15F84603
(5'- ATAGAGGCGACTTTTCCGGAG -3');    (SEQ ID NO: 70)

M111L15R85203
(5'- ACAAGAACAAGACGCTCGAGG -3');    (SEQ ID NO: 71)

M111L15F85106
(5'- CCAGTGTGAGTGTATGCGAGC -3');    (SEQ ID NO: 72)

M111L15R85696
(5'- TCACGATCCCTTCTTTCCCTC -3');    (SEQ ID NO: 73)

M111L15F85545
(5'- CCGGTGAAACTGAAGCTACTG -3');    (SEQ ID NO: 74)

M111L15R86124
(5'- TCCGAATGAAATGAACTCTGC -3');    (SEQ ID NO: 75)

M111L15F86010
(5'- CCACATTAGCATTGACCTGAG -3');    (SEQ ID NO: 76)
and

M111L15R86329
(5'- GTCATAACTCGGCAAACATAG -3').    (SEQ ID NO: 77)
```

4.2 Results and Discussion 4.2.1 Narrowing the Gene Based on Partial Genomic Deletions Found in Mutants Unambiguous partial genomic deletions were found in six lines of hex-v mutants (hex-v.3, hex-v.10, hex-v.11, hex-v.18, hex-v.35, and hex-v.41) while there was no detectable deletion in the original varieties (FIG. 3). These deletions were considered to cause the phenotypic alterations in the mutants. The shared deletion spans at most the 253-kb region (from position 8998 to 262406) between E30 and 669N11-T7. This region contains the above-described homeobox gene. Furthermore, in a deletion mutant (hex-v.33), the deletion at most spans the 81-kb region (from position 83226 to 164320) between 351N10-T7 (from 203 to 392) and E42. This region contains the 3'-untranslated region of the homeobox gene.

The above result strongly suggests that the homeobox gene is a causative gene located at the row type-determining locus. All the deletion mutants described above were induced by neutron, X ray, or gamma ray. Meanwhile, according to the result of PCR analysis, there were not deletion mutants found among the Int-d mutants. Their phenotypes and modes of inheritance suggest that the Int-d mutants are not completely defective in function but retain their function to some extent. The obtained experimental result agrees well with the previous findings.

4.2.2 Mutations in the DNA Nucleotide Sequence of the Row Type-Governing Gene in Mutant Lines The genomic nucleotide sequences comprising the homeobox gene were compared with those of the original varieties and mutants (FIG. 4-1 to 4-11). No mutation was found in the nucleotide sequence of the homeobox gene in the original three varieties. In contrast, aside from the deletion of the homeobox gene in the above-described six deletion lines (hex-v.3, hex-v. 10, hex-v.11, hex-v. 18, hex-v.35, and hex-v.41), nucleotide substitutions that resulted in a non-synonymous amino acid substitution or stop codon formation were most frequently found in the mutants, and the next most frequent mutation was deletions of a small number of nucleotides that resulted in a shift of the reading frame. In addition, nucleotide substitutions thought to modify mRNA splicing were also detected. The above finding demonstrates that the homeobox gene is a causative gene located at the row type-determining locus.

Example 5

Analysis of Gene Expression 5.1 Materials and Methods

Under a stereoscopic microscope, leaf blades and young panicles (1 to 50 mm) were excised from barley about five months after seeding in the open air. RNAs were extracted using the Trizol method (Invitrogen). The first strand cDNAs were synthesized using the Superscript II kit (Invitrogen). DNAs amplified by RT-PCR were observed by agarose gel electrophoresis.

5.2 Results and Discussion

Figure 5:
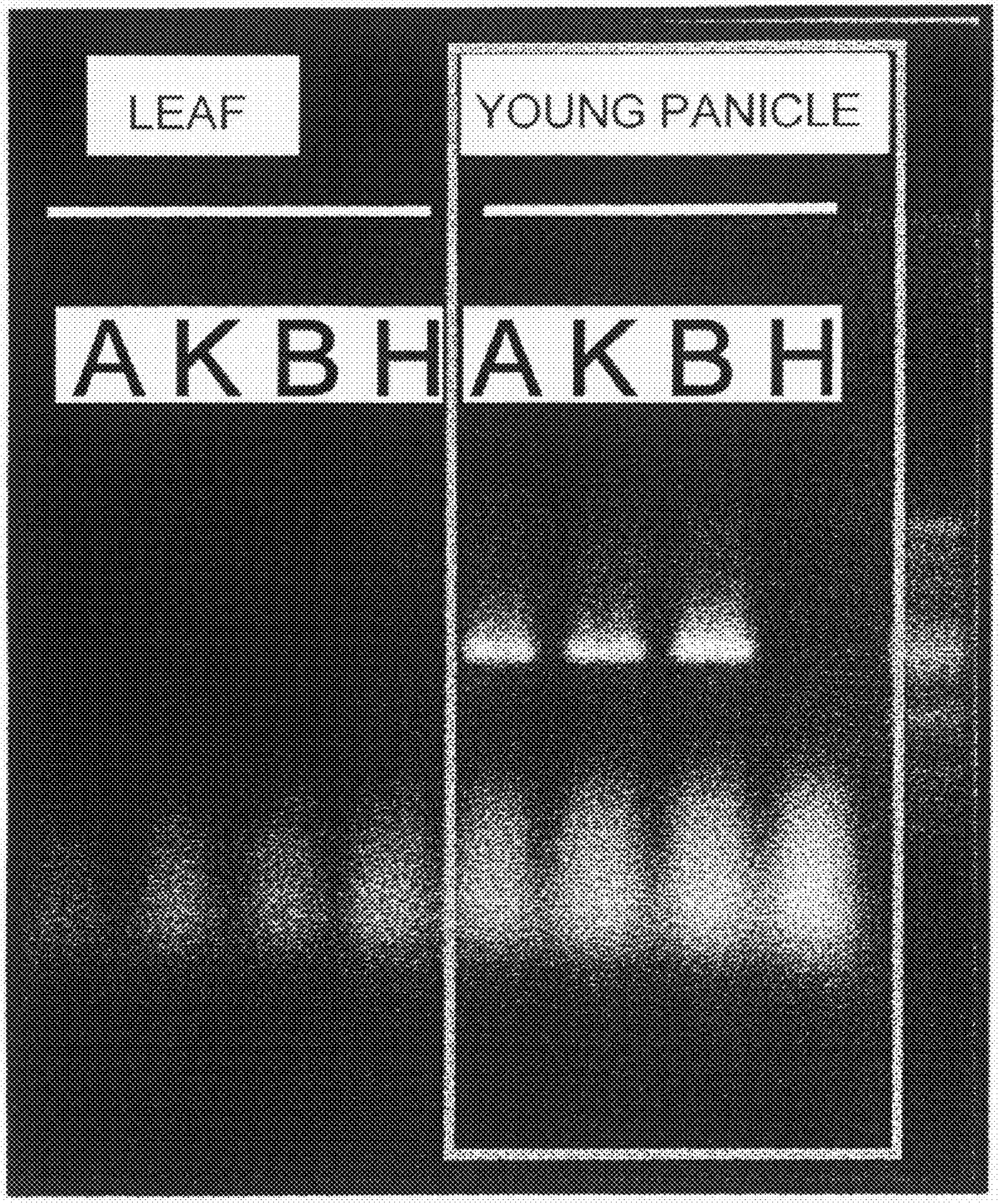

Expression of the homeobox gene was detected in young panicle tissues but not in leaf blades (FIG. 5). In young panicles, active expression was found, in particular, from the double ridge stage to awn primordium stage where the panicle length was 1 to 5 mm, and the expression level decreased as the developmental stage proceeded. The expression level of the actin gene, which was used as a control, was observed to be constant regardless of the type of tissue and developmental stage. The homeobox gene was indeed active in transcription and expressed in panicles prior to determination of the row type in barley, as described above. Thus, the homeobox gene was proven to be the causative gene that serves as a row type gene vrs1.

INDUSTRIAL APPLICABILITY

It is known that there are two-rowed and six-rowed varieties in barley. The row type directly influences the yield, because it has a great impact on determining the number, shape, and size of grains. For example, the number of grains in six-rowed barley is three times as many as that of two-rowed barley, and therefore six-rowed barley promises high yield. Thus, six-rowed barley is useful as feed and such. By contrast, two-rowed barley is characterized by grain size homogeneity, and thus superior in uniform germination in the production of malt. Because of its superior production efficiency, two-rowed barley is mainly useful in beer brewing in Japan and Europe. Thus, there are appropriate applications of six-rowed and two-rowed barley depending on their characteristics, economic significances, availabilities, and so on.

The present invention provides the chromosomal location and structure of the gene involved in the determination of row type and panicle morphology of barley. The row type and panicle morphology of barley may be altered by introducing the Vrs1 gene of the present invention or a mutant thereof into barley and regulating its expression. Specifically, morphologies that meet the purpose can be created by adjusting the balance between the central and lateral spikelets in panicles using the Vrs1 gene of the present invention or a mutant thereof. Furthermore, the present invention found the possibility of enhancing the resistance of barley to *Fusarium* head blight.

Barley is being distributed on the market as plants for floral arrangement. Thus, barley altered to be two-rowed, six-rowed, or of an intermediate type between the two-row and six-row types can be used in floral arrangement, and is useful as ornamental plants. In particular, barley that has been altered to be as intermediate type between the two-row and six-row types is valuable and useful as an atypical variety.

The invention claimed is:

1. An isolated DNA selected from the group consisting of:

(a) a DNA encoding a protein comprising the amino acid sequence of SEQ ID NO: 3; and (b) a DNA comprising the coding region of the nucleotide sequence of SEQ ID NO: 1 or 2.

2. A vector comprising the DNA of claim 1.

3. An isolated transformed cell harboring the DNA of claim 1 in an expressible manner.

4. A transformed barley cell into which the DNA of claim 1 has been introduced.

5. A transformed barley plant comprising the transformed barley cell of claim 4.

6. A transformed barley plant which is a progeny or clone of the transformed barley plant of claim 5 and wherein the progeny comprise said DNA.

7. A breeding material of the transformed barley plant of claim 5.

8. A method for producing the transformed barley plant of claim 5, which comprises the step of introducing a DNA into a barley cell and then regenerating a barley plant from the barley cell, wherein the DNA is selected from the group consisting of (a) a DNA encoding a protein comprising the amino acid sequence of SEQ ID NO: 3, and (b) a DNA comprising the coding region of the nucleotide sequence of SEQ ID NO: 1 or 2.

9. A method for altering the row type or panicle morphology of a barley plant, which comprises the step of expressing the DNA of (a) or (b) of claim 1 in a cell of a barley plant that is not two-rowed.

10. A method for conferring a barley plant with resistance to *Fusarium* head blight, which comprises the step of expressing the DNA of claim 1 in a barley cell.

11. An agent for enhancing resistance of a barley plant to *Fusarium* head blight, which comprises the DNA of claim 1, and a vector comprising said DNA.

12. A breeding material of the transformed barley plant of claim 6.

13. A method for producing the transformed barley plant of claim 6, which comprises the step of introducing a DNA into a barley cell and then regenerating a barley plant from the barley cell, wherein the DNA is selected from the group consisting of:

(a) a DNA encoding a protein comprising the amino acid sequence of SEQ ID NO: 3, and (b) a DNA comprising the coding region of the nucleotide sequence of SEQ ID NO: 1 or 2; and producing a progeny barley plant that comprises said DNA.

14. An isolated DNA selected from the group consisting of (1) to (33) below:

(1) a DNA comprising the coding region of the nucleotide sequence of SEQ ID NO: 1, wherein C at position 701 has been deleted, (2) a DNA comprising the coding region of the nucleotide sequence of SEQ ID NO: 1, wherein G at position 733 has been substituted with A, (3) a DNA comprising the coding region of the nucleotide sequence of SEQ ID NO: 1, wherein A at position 855 has been substituted with C, (4) a DNA comprising the coding region of the nucleotide sequence of SEQ ID NO: 1 wherein C at position 865 has been substituted with T, (5) a DNA comprising the coding region of the nucleotide sequence of SEQ ID NO: 1, wherein G at position 958 has been substituted with T, (6) a DNA comprising the coding region of the nucleotide sequence of SEQ ID NO: 1, wherein T at position 1018 has been substituted with A, (7) a DNA comprising the coding region of the nucleotide sequence of SEQ ID NO: 1, wherein G at position 1049 has been substituted with A, (8) a DNA comprising the coding region of the nucleotide sequence of SEQ ID NO: 1, wherein T at position 1061 has been substituted with A, (9) a DNA comprising the coding region of the nucleotide sequence of SEQ ID NO: 1, wherein C at position 1064 has been substituted with T,

(10) a DNA comprising the coding region of the nucleotide sequence of SEQ ID NO: 1, wherein T at position 1073 has been substituted with A,

(11) a DNA comprising the coding region of the nucleotide sequence of SEQ ID NO: 1, wherein T at position 1079 has been substituted with A,

(12) a DNA comprising the coding region of the nucleotide sequence of SEQ ID NO: 1, wherein T at position 1102 has been substituted with A,

(13) a DNA comprising the coding region of the nucleotide sequence of SEQ ID NO: 1, wherein C at position 1108 has been substituted with T,

(14) a DNA comprising the coding region of the nucleotide sequence of SEQ ID NO: 1, wherein A at position 1111 has been substituted with T,

(15) a DNA comprising the coding region of the nucleotide sequence of SEQ ID NO: 1, wherein G at position 1115 has been substituted with T,

(16) a DNA comprising the coding region of the nucleotide sequence of SEQ ID NO: 1, wherein G at position 1124 has been substituted with A,

(17) a DNA comprising the coding region of the nucleotide sequence of SEQ ID NO: 1, wherein A at position 1135 has been substituted with T,

(18) a DNA comprising the coding region of the nucleotide sequence of SEQ ID NO: 1, wherein A at position 1193 has been substituted with C,

(19) a DNA comprising the coding region of the nucleotide sequence of SEQ ID NO: 1, wherein A at position 1195 has been substituted with T,

(20) a DNA comprising the coding region of the nucleotide sequence of SEQ ID NO: 1, wherein G at position 1213 has been substituted with T,

(21) a DNA comprising the coding region of the nucleotide sequence of SEQ ID NO: 1, wherein G at position 1311 has been substituted with A,

(22) a DNA comprising the coding region of the nucleotide sequence of SEQ ID NO: 1, wherein A at position 1335 has been substituted with T,

(23) a DNA comprising the coding region of the nucleotide sequence of SEQ ID NO: 1, wherein T at position 1476 has been substituted with A,

(24) a DNA comprising the coding region of the nucleotide sequence of SEQ ID NO: 1, wherein C at position 1482 has been substituted with T,

(25) a DNA comprising the coding region of the nucleotide sequence of SEQ ID NO: 1, wherein C at position 1485 has been substituted with T,

(26) a DNA comprising the coding region of the nucleotide sequence of SEQ ID NO: 1, wherein the nucleotide sequence corresponding from the $1504^{th}$ to the $1514^{th}$ position in the nucleotide sequence set forth in SEQ ID NO: 1 has been deleted,

(27) a DNA comprising the coding region of the nucleotide sequence of SEQ ID NO: 1, wherein C at position 1020 has been substituted with G,

(28) a DNA comprising the coding region of the nucleotide sequence of SEQ ID NO: 1, wherein A at position 694 has been substituted with G, T at position 873 has been substituted with G, and G at position 1352 has been deleted,

(29) a DNA comprising the coding region of the nucleotide sequence of SEQ ID NO: 1, wherein A at position 694 has been substituted with G, T at position 873 has been substituted with G, and T at position 915 has been inserted,

(30) a DNA comprising the coding region of the nucleotide sequence of SEQ ID NO: 1, wherein A at position 694 has been substituted with G, and T at position 873 has been substituted with G,

(31) a DNA comprising the coding region of the nucleotide sequence of SEQ ID NO: 1, wherein A at position 694 has been substituted with G, T at position 873 has been substituted with G, and C at position 1097 has been substituted with T,

(32) a DNA comprising the coding region of the nucleotide sequence of SEQ ID NO: 1, wherein A at position 694 has been substituted with G, T at position 873 has been substituted with G, G at position 1386 has been substituted with C, and G at position 1423 has been substituted with A, and

(33) a DNA comprising the coding region of the nucleotide sequence of SEQ ID NO: 1, wherein A at position 694 has been substituted with G, T at position 873 has been substituted with G, and A at position 1446 has been substituted with G.

* * * * *